US012621668B2

(12) United States Patent

Goudge

(10) Patent No.: US 12,621,668 B2
(45) Date of Patent: May 5, 2026

(54) PROVIDING DATA INTEGRITY AND USER PRIVACY IN NEUROMUSCULAR-BASED GESTURE RECOGNITION AT A WEARABLE DEVICE, AND SYSTEMS AND METHODS OF USE THEREOF

(71) Applicant: Meta Platforms Technologies, LLC, Menlo Park, CA (US)

(72) Inventor: Charles Liam Goudge, Menlo Park, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 255 days.

(21) Appl. No.: 18/363,659

(22) Filed: Aug. 1, 2023

(65) Prior Publication Data

US 2024/0284179 A1 Aug. 22, 2024

Related U.S. Application Data

(60) Provisional application No. 63/486,448, filed on Feb. 22, 2023.

(51) Int. Cl.
| | |
|---|---|
| *H04W 12/106* | (2021.01) |
| *G06F 3/01* | (2006.01) |
| *G16H 40/67* | (2018.01) |
| *H04W 12/037* | (2021.01) |

(52) U.S. Cl.
CPC .......... *H04W 12/106* (2021.01); *G06F 3/015* (2013.01); *G16H 40/67* (2018.01); *H04W 12/037* (2021.01)

(58) Field of Classification Search
CPC .................................................. H04W 12/106
USPC .......................................................... 713/153
See application file for complete search history.

(56) References Cited

U.S. PATENT DOCUMENTS

| | | | |
|---|---|---|---|
| 2018/0341347 A1* | 11/2018 | Yousefpor | G06F 3/043 |
| 2019/0384901 A1* | 12/2019 | Osborn | G06N 3/08 |
| 2021/0064132 A1* | 3/2021 | Rubin | G06F 3/017 |
| 2021/0169417 A1* | 6/2021 | Burton | A61B 5/4857 |
| 2023/0057294 A1* | 2/2023 | Park | A61H 3/00 |
| 2024/0048539 A1* | 2/2024 | Nguyen | H04L 9/14 |
| 2024/0168567 A1* | 5/2024 | Barachant | G06F 1/163 |

* cited by examiner

*Primary Examiner* — Lan Dai T Truong
(74) *Attorney, Agent, or Firm* — Morgan, Lewis & Bockius LLP

(57) ABSTRACT

A method of providing data integrity to a system that includes a neuromuscular-signal-sensing component of a wearable device is described. The operations of the method can be performed at a neuromuscular-signal-sensing component of a wearable device. The method includes detecting a neuromuscular signal via one or more electrodes. The method further includes generating a digital signal by converting the neuromuscular signal. The method further includes generating an encrypted signal to a controller component of the wearable device, the controller component being distinct from the neuromuscular-signal-sensing component.

20 Claims, 23 Drawing Sheets

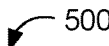

500

502 At a neuromuscular-signal-sensing component of a wearable device:

> 504 Detect a neuromuscular signal via one or more electrodes.

> 506 Generate a digital signal by converting the neuromuscular signal.

> 508 Generate an encrypted signal by encrypting the digital signal.

> 510 Transmit the encrypted signal to a controller component of the wearable device, the controller component being distinct from the neuromuscular-sensing component.

512 At the controller component:

> 514 Receive the encrypted signal from the neuromuscular-signal-sensing component.

> 516 Generate a decrypted signal by decrypting the encrypted signal.

> 518 Validate the neuromuscular-signal-sensing component based on the decrypted signal.

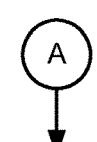

520 In accordance with the neuromuscular-signal-sensing component not being validated, generating a notification for a user of the wearable device.

522 In accordance with the neuromuscular-signal-sensing component being validated, adjusting a machine-learning model based on one or more capabilities of the neuromuscular-signal-sensing component.

524 After adjusting the machine-learning model, send the machine-learning model to the neuromuscular-signal-sensing component.

526 Receive a signal from an additional neuromuscular-signal-sensing component.

528 Validate the additional neuromuscular-signal-sensing component based on the received signal.

530 In accordance with the additional neuromuscular-signal-sensing component being validated, activate an operating mode of the wearable device.

Figure 5B

AR system 5000c 5002       7010

8000

6000

AR system 5000c

AR system 5000d

9000

AR system 5000d

AR system 7000

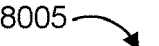
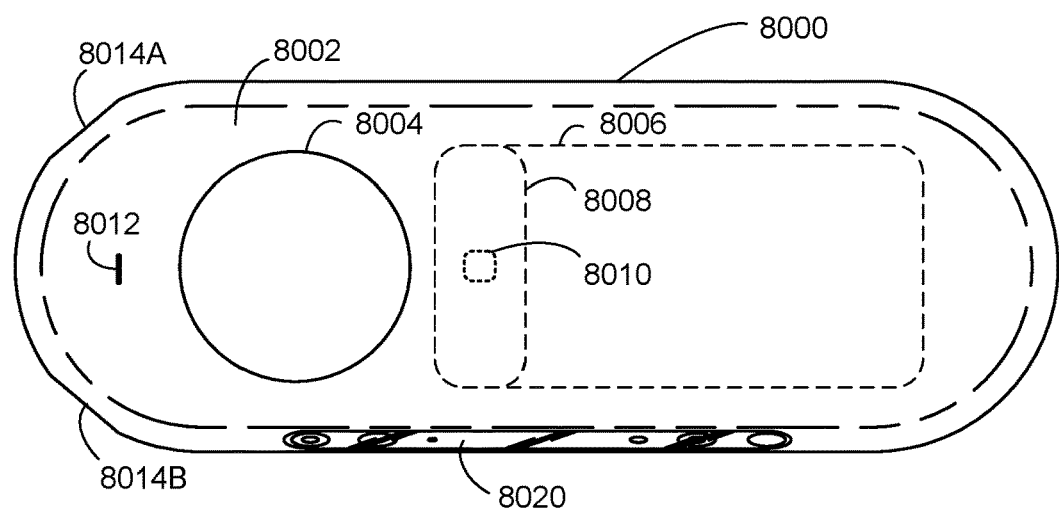
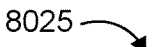
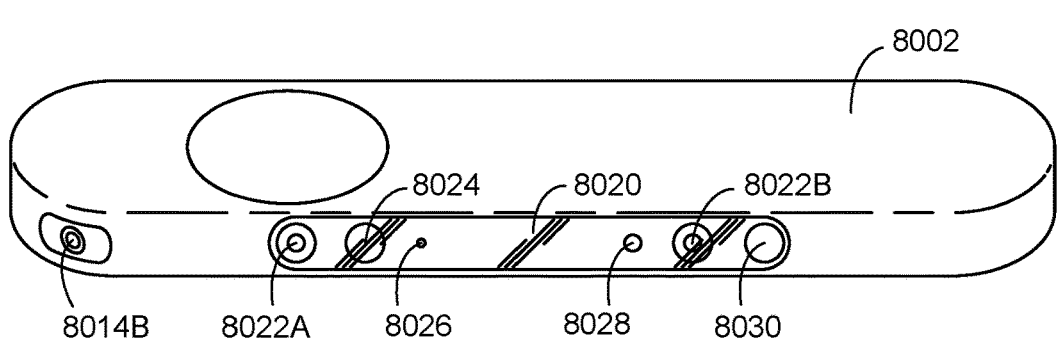
Figure 9A

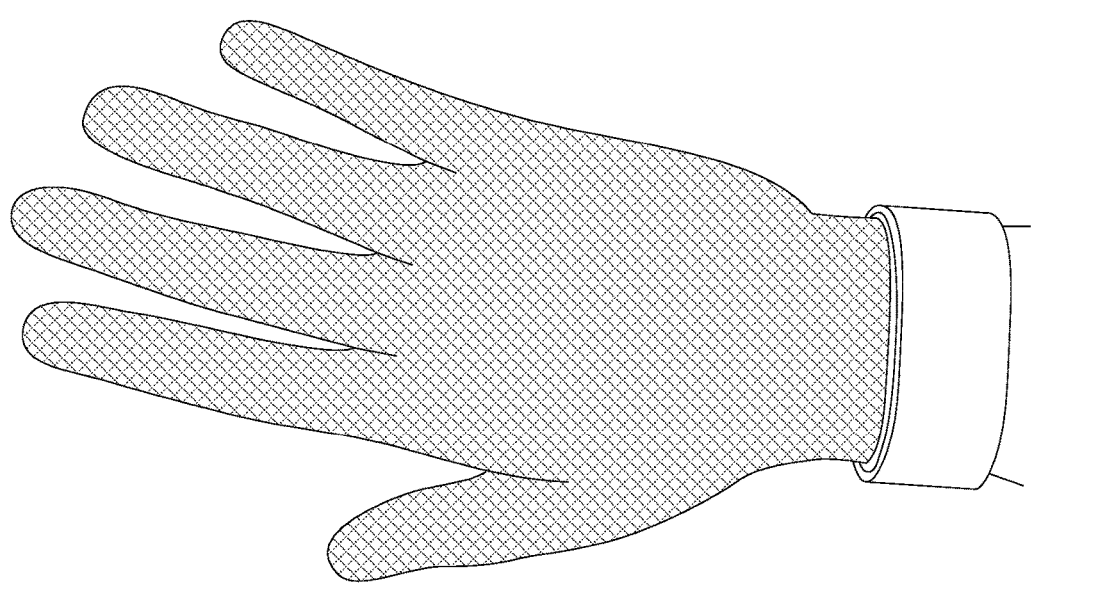
Figure 10B
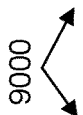
9000
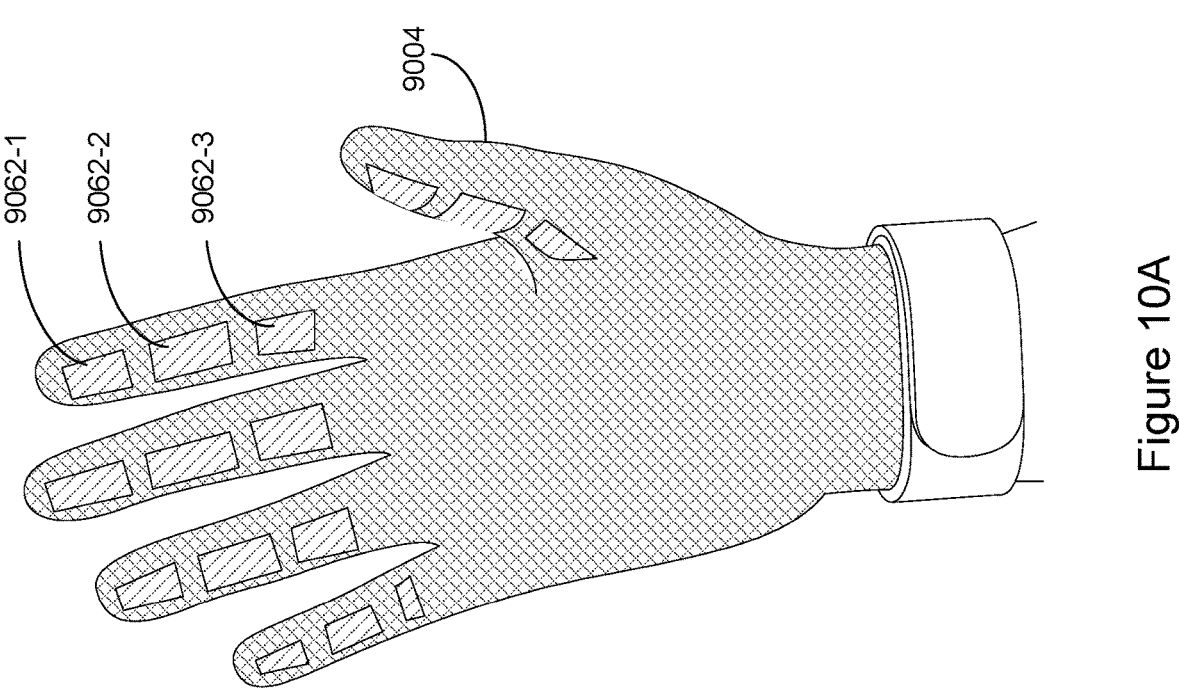
Figure 10A

PROVIDING DATA INTEGRITY AND USER PRIVACY IN NEUROMUSCULAR-BASED GESTURE RECOGNITION AT A WEARABLE DEVICE, AND SYSTEMS AND METHODS OF USE THEREOF

CROSS-REFERENCE TO RELATED APPLICATIONS

This application claims priority to U.S. Prov. App. No. 63/486,448, filed on Feb. 22, 2023, and entitled "Providing Data Integrity and User Privacy in Neuromuscular-Based Gesture Recognition at a Wearable Device, and Systems and Methods of Use Thereof," which is hereby incorporated by reference in its entirety.

TECHNICAL FIELD

The present disclosure relates generally to biopotential-signal-sensing devices, systems, and methods, including but not limited to techniques for providing data integrity for wearable biopotential-signal-sensing devices (e.g., validation of encrypted signals provided to a controller component from a neuromuscular-signal sensor of a wearable device).

BACKGROUND

Biopotential-signal-sensing applications, such as electromyography (EMG) and electrocardiography (ECG), detect and interpret small electrical signals in the body (e.g., neuromuscular signals). For example, users of wearable devices can perform gestures that are detected by neuromuscular-signal-sensing components (e.g., biopotential-signal sensors that include neuromuscular-signal-sensing electrodes) and interpreted to provide a man-machine interface. As another example, the biopotential signals can be used to monitor a user's vitals (e.g., while the user is working out). Each of these biopotential signals may be more personal to users than other signals and/or computer inputs (e.g., keyboard/mouse activity). Therefore, it is important to protect the biopotential signals and/or data generated from the biopotential signals.

SUMMARY

As described herein, protecting the biopotential signals can include preventing a malicious actor from obtaining the signals and/or generated data, as well as inserting fake biopotential signals to confuse/manipulate the man-machine interface. Additionally, providing security between sensors and a compute core (e.g., a central processing unit (CPU) configured to receive data from sensors of a wearable device) can prevent insertion of invalid components that lack the capabilities of valid components and can therefore cause system failures.

For example, encrypting data obtained by and/or translated from biopotential-signal sensors allows for such data to be protected from nefarious actors. A validation process based on such encryption also provides source identification when components related to biopotential-signal sensing are replaced on and/or added to a wearable device. Additionally, once a common encryption scheme is established for biopotential-signal sensing at a wearable device (e.g., via a secret, key, seed, and/or token), more sophisticated functionality (e.g., trained artificial intelligence and/or machine-learning models) can be provided directly to sensors and other constituent components that have more limited computing functionality without sacrificing data protection goals. Such localization techniques can also reduce overhead time and/or bandwidth for certain computational tasks by reducing the amount of communication between separate hardware components of the wearable device.

The methods, systems, and devices described herein allow users and manufacturers of wearable devices that include biopotential-signal sensors, and constituent components thereof, to ensure that data is protected and/or meets performance criteria (e.g., with respect to encryption, durability, sensing capability, and/or data integrity) via decryption and validation of the biopotential signals by a controller component of the wearable device.

One example of a method for providing data integrity at a wearable device is provided. Operations of this example method are performed at a neuromuscular-signal-sensing component of the wearable device. The example method includes detecting a neuromuscular signal via one or more electrodes. The example method includes generating a digital signal by converting the neuromuscular signal. The example method includes generating an encrypted signal by encrypting the digital signal. And the example method includes transmitting the encrypted signal to a controller component of the wearable device, the controller component being distinct from the neuromuscular-signal-sensing component. Several examples that can be actuated so as to cause the operations described above to be performed are shown in the sequences of FIGS. 1A-3B.

In some embodiments, a computing device (e.g., a wrist-wearable device or a head-mounted device, or an intermediary device, such as a smartphone or desktop or laptop computer) includes one or more processors, memory, a display (in some embodiments, the display can be optional, such as for certain example intermediary devices that can coordinate operations at the wrist-wearable device and the head-mounted device, and thus have ample processing and power resources, but need not have its own display), and one or more programs stored in the memory. The programs are configured for execution by the one or more processors. The one or more programs include instructions for performing (or causing performance of) any of the methods described herein.

In some embodiments, a non-transitory computer-readable storage medium stores one or more programs configured for execution by a computing device (e.g., a wrist-wearable device or a head-mounted device, or an intermediary device, such as a smartphone or desktop or laptop computer that can be configured to coordinate operations at the wrist-wearable device and the head-mounted device) having one or more processors and memory. The one or more programs include instructions for performing (or causing performance of) any of the methods described herein.

Thus, methods, systems, and computer-readable storage media are disclosed for providing biosensing. Such methods and systems may complement or replace conventional methods for providing biosensing.

The features and advantages described in the specification are not necessarily all inclusive and, in particular, certain additional features and advantages will be apparent to one of ordinary skill in the art in view of the drawings, specification, and claims. Moreover, it should be noted that the language used in the specification has been principally selected for readability and instructional purposes.

Having summarized the above example aspects, a brief description of the drawings will now be presented.

BRIEF DESCRIPTION OF THE DRAWINGS

For a better understanding of the various described embodiments, reference should be made to the Detailed Description below, in conjunction with the following drawings in which like reference numerals refer to corresponding parts throughout the figures.

FIGS. 5A-5B show a flow chart for an example method of providing data integrity for neuromuscular signals detected by a neuromuscular-signal sensor of a wearable device in accordance with some embodiments.

FIGS. 9A-9B illustrate an example handheld device in accordance with some embodiments.

FIGS. 10A-10C illustrate example wearable gloves in accordance with some embodiments.

Figure 1A:
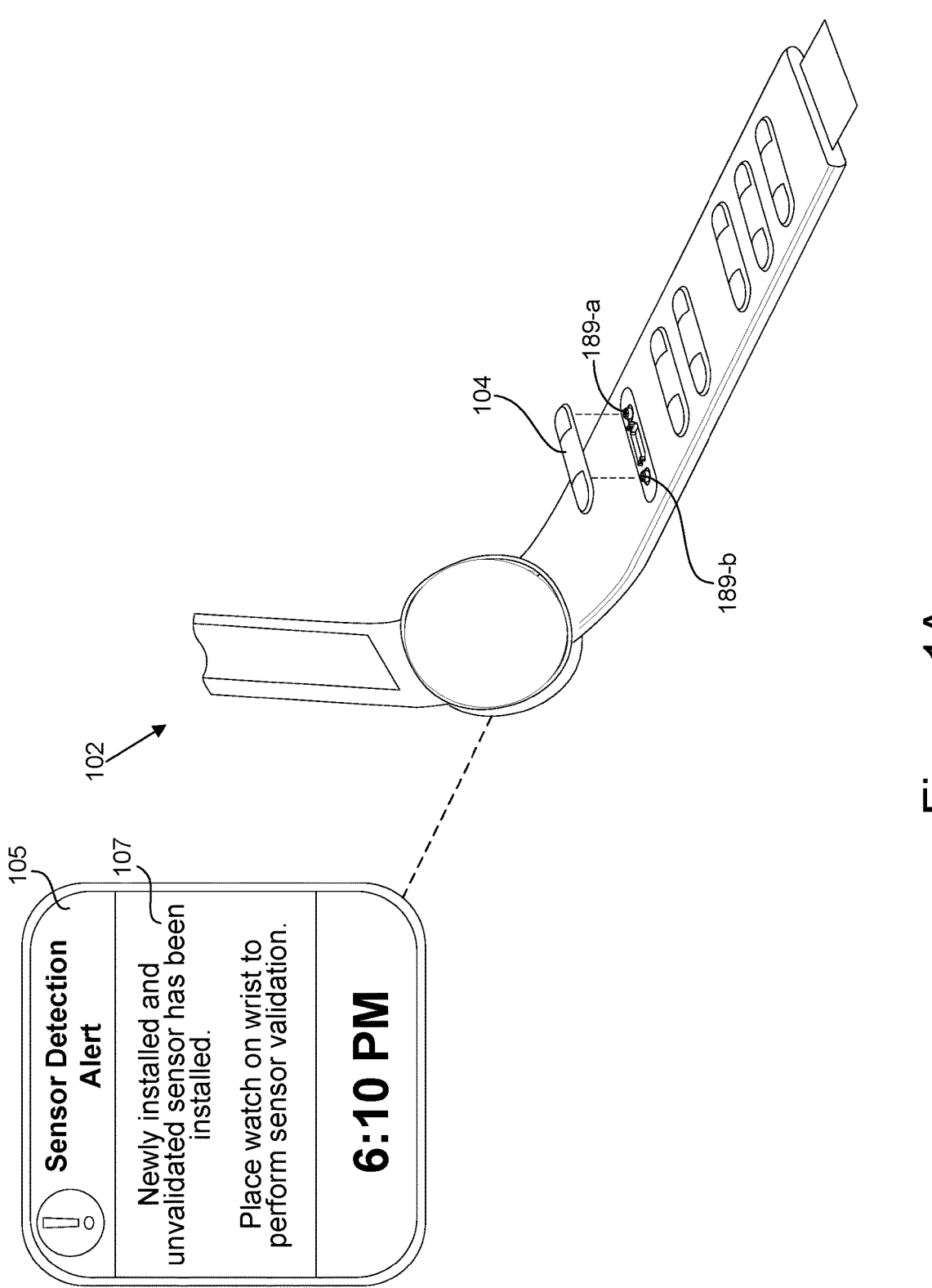
FIGS. 1A-1G show example scenarios of a wrist-wearable device validating a neuromuscular-signal sensor of the wrist-wearable device in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method, or device. Finally, similar reference numerals may be used to denote like features throughout the specification and figures.

DETAILED DESCRIPTION

Numerous details are described herein to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not necessarily been described in exhaustive detail so as to avoid obscuring pertinent aspects of the embodiments described herein.

Embodiments of the present disclosure include biopotential-signal-sensing devices, including neuromuscular-signal-sensing components, such as neuromuscular-signal sensors that include one or more electrodes for detecting neuromuscular activity of a human body. As described herein, a biopotential-signal-sensing device can include one or more individual biopotential-signal sensors, including neuromuscular-signal sensors, such as EMG sensors. An individual biopotential-signal sensor, such as a neuromuscular-signal sensor, can be associated with a plurality of electrodes located at a plurality of different locations on one or more wearable devices. For example, a particular neuromuscular-signal sensor can include two individual EMG electrodes located on a pill-shaped structure, the two EMG electrodes separated by an insulating structure of a carrier component of the sensor.

The present disclosure describes providing encryption between biopotential-signal sensor components and a compute core. The encryption can be implemented using a shared secret or key that is provided by a manufacturer or retailer. The encryption can also be used to validate the components and ascertain their capabilities. For example, a first shared secret can be used for a first type of sensor (e.g., having a first set of capabilities) and a second shared secret can be used for a second type of sensor (e.g., having a second set of capabilities). In this way, identifying the secret used for the encryption also identifies the type of sensor and/or capabilities. Providing encryption between the sensor components and the compute core prevents man-in-the-middle attacks as well as insertion of imitation components that lack required capabilities.

In some embodiments, a wearable device has sensor-receiving structures configured to receive one or more biopotential-signal-sensing devices. In some embodiments, the sensor-receiving structures are configured to provide signals received by the one or more biopotential-signal-sensing devices (e.g., corresponding to one or more sensor-skin interfaces) to a compute core of the wearable device.

Embodiments of this disclosure can include or be implemented in conjunction with various types or embodiments of artificial-reality (AR) systems. Artificial reality, as described herein, is any superimposed functionality and or sensory-detectable presentation provided by an AR system within a user's physical surroundings. AR can include and/or represent virtual reality (VR), augmented reality, mixed artificial reality (MAR), or some combination and/or variation one of these. For example, a user can perform a swiping in-air hand gesture to cause a song to be skipped by a song-providing application programming interface (API) providing playback at, for example, a home speaker. In some embodiments of an AR system, ambient light (e.g., a live feed of the surrounding environment that a user would normally see) can be passed through a display element of a respective head-wearable device presenting aspects of the AR system. In some embodiments, ambient light can be passed through a respective aspect of the AR system. For example, a visual user interface element (e.g., a notification user interface element) can be presented at the head-wearable device, and an amount of ambient light (e.g., 15%-50% of the ambient light) can be passed through the user interface element, such that the user can distinguish at least a portion of the physical environment over which the user interface element is being displayed.

AR content can include completely generated content or generated content combined with captured (e.g., real-world) content. The AR content can include video, audio, haptic events, or some combination thereof, any of which can be presented in a single channel or in multiple channels (such as stereo video that produces a three-dimensional effect to a viewer). Additionally, in some embodiments, AR content can also be associated with applications, products, accessories, services, or some combination thereof, which are used, for example, to create content in an AR environment and/or are otherwise used in (e.g., to perform activities in) an AR environment.

Turning now to the drawings, FIGS. 1A-1G show an example sequence of a wrist-wearable device 102 validating a neuromuscular-signal sensor of the wrist-wearable device 102 in accordance with some embodiments. The wrist-wearable device 102 includes a plurality of neuromuscular-signal-sensing components (e.g., a neuromuscular-signal-sensing component 104 shown in FIG. 1A), and a controller component arranged to be in communication with one or more of the plurality of neuromuscular-signal-sensing components. In some embodiments, the neuromuscular-signal-sensing components are arranged on another type of wearable device (e.g., an AR system 1400 and/or a VR system 1450 as described in more detail in FIGS. 7A-7B). In some embodiments, the wrist-wearable device 102 may include any or all of the components described with respect to FIGS. 3A-3B.

FIG. 1A shows a wrist-wearable device 102 that includes a plurality of neuromuscular-signal-sensing components (e.g., biopotential-signal sensors), and a neuromuscular-signal-sensing component 104 is being placed onto the wrist-wearable device 102 (e.g., via electronically active socket connectors). A user may be placing the neuromuscular-signal-sensing component 104 into the wrist-wearable device to replace another neuromuscular-signal-sensing component that was broken, lost, or otherwise displaced from the wrist-wearable device 102. As another example, the user may be placing the neuromuscular-signal-sensing component 104 to upgrade one or more sensing capabilities with regard to a previously connected sensing component.

A display 105 of the wrist-wearable device 102 is displaying a notification 107 in FIG. 1A. The notification 107 indicates that a new sensor has been installed, e.g., in accordance with the neuromuscular-signal-sensing component 104 being placed onto the wrist-wearable device 102. The notification 107 also indicates that the newly installed sensor is unvalidated and prompts the user to don the wrist-wearable device to perform sensor validation techniques (the notification 107 stating: "Newly installed and unvalidated sensor has been installed. Place watch on wrist to perform sensor validation."). In some embodiments, the notification 107 is displayed in response to a user powering on the wrist-wearable device 102. In some embodiments, the notification 107 is displayed in response to the user coupling the neuromuscular-signal-sensing component 104 to the wrist-wearable device 102.

In some embodiments, the wrist-wearable device 102 includes a plurality of sensor-receiving structures (e.g., sensor-receiving structures 189-a and 189-b). In some embodiments, respective sensor-receiving structures of the wrist-wearable device 102 are replaceable similar to the neuromuscular-signal-sensing component 104. The techniques described herein can be performed with respect to sensor-receiving structures of the wrist-wearable device, based on a detection that a new sensor-receiving structure has been installed at the wrist-wearable device 102. That is, a newly-installed sensor-receiving structure of a wearable electronic device can be configured to provide an encrypted signal to a controller component of the wearable device, and the controller component can apply a decryption technique to the encrypted signal to determine if the encrypted signal from the sensor-receiving structure is encrypted using a particular key associated with a particular manufacturer.

Figure 1C:
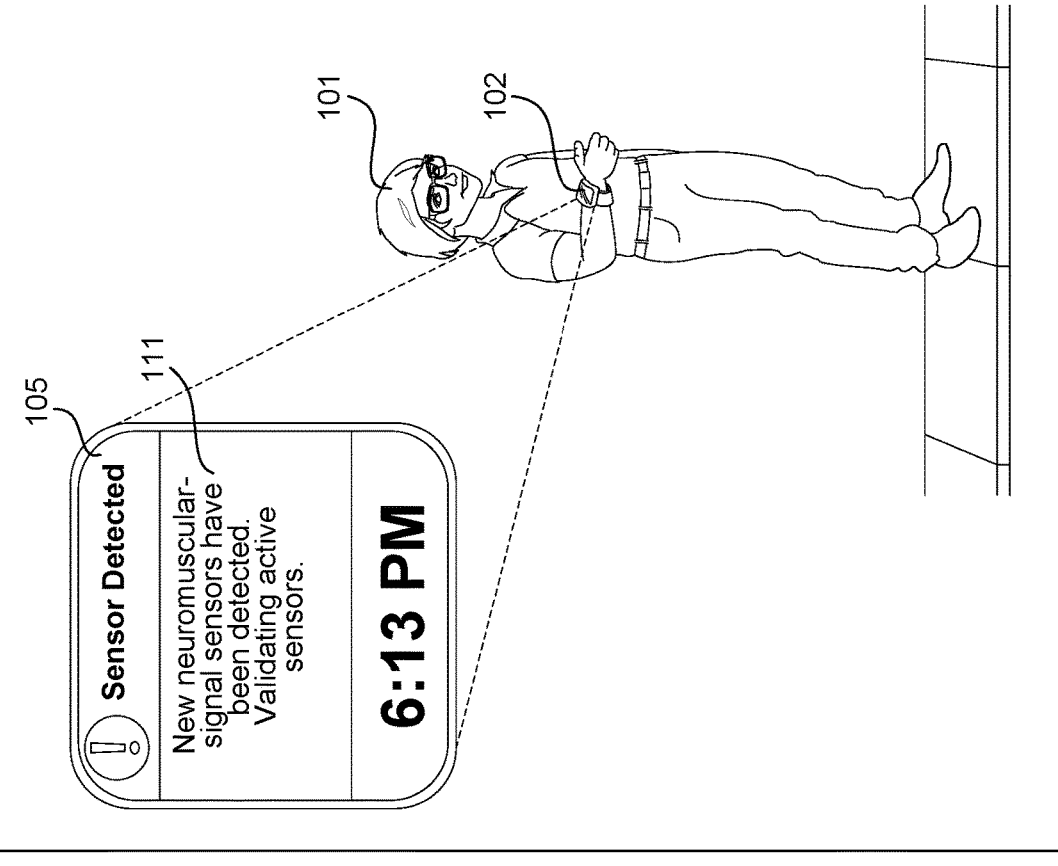
Figure 1B:
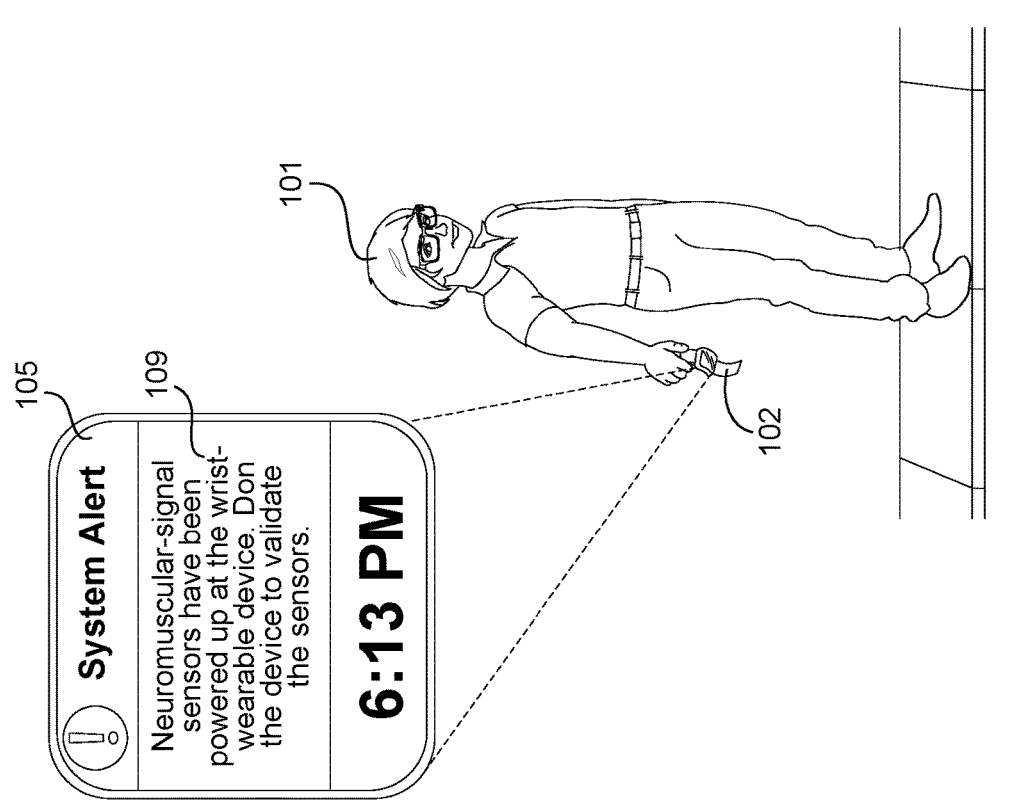

FIG. 1B shows the user 101 holding the wrist-wearable device 102. The display 105 of the wrist-wearable device 102 is displaying a notification 109 indicating that the neuromuscular-signal-sensing components (e.g., the neuromuscular-signal-sensing component 104 shown in FIG. 1A) of the wrist-wearable device 102 are powered on and capable of detecting neuromuscular signals required for sensor validation to be performed (the notification 109 stating: "Neuromuscular-signal sensors have been powered up at the wrist-wearable device. Don the device to validate the sensors."). In some embodiments, the notification 109 is displayed in response to a user powering on the wrist-wearable device 102.

FIG. 1C shows the user 101 wearing the wrist-wearable device 102, and the display of the wrist-wearable device 102 is displaying a notification 111 indicating that the wrist-wearable device is validating active neuromuscular-signal-sensing components of the wrist-wearable device 102 (e.g., the neuromuscular-signal-sensing component 104 shown in FIG. 1A). In some embodiments, a threshold level of impedance must be present at each of the neuromuscular-signal-sensing components that require validation, which can be based on an amount of surface contact with a sensor-skin interface of the user's body (e.g., a portion of the wrist of the user 101 onto which the wrist-wearable device 102 is donned). In some embodiments, the neuromuscular-signal-sensing components are validated based on an encryption used for biopotential data obtained from the user 101. In some embodiments, the neuromuscular-signal-sensing components are validated without the wrist-wearable device 102 being worn (e.g., the neuromuscular-signal-sensing components send an encrypted signal that does not include biopotential data).

Figure 1E:
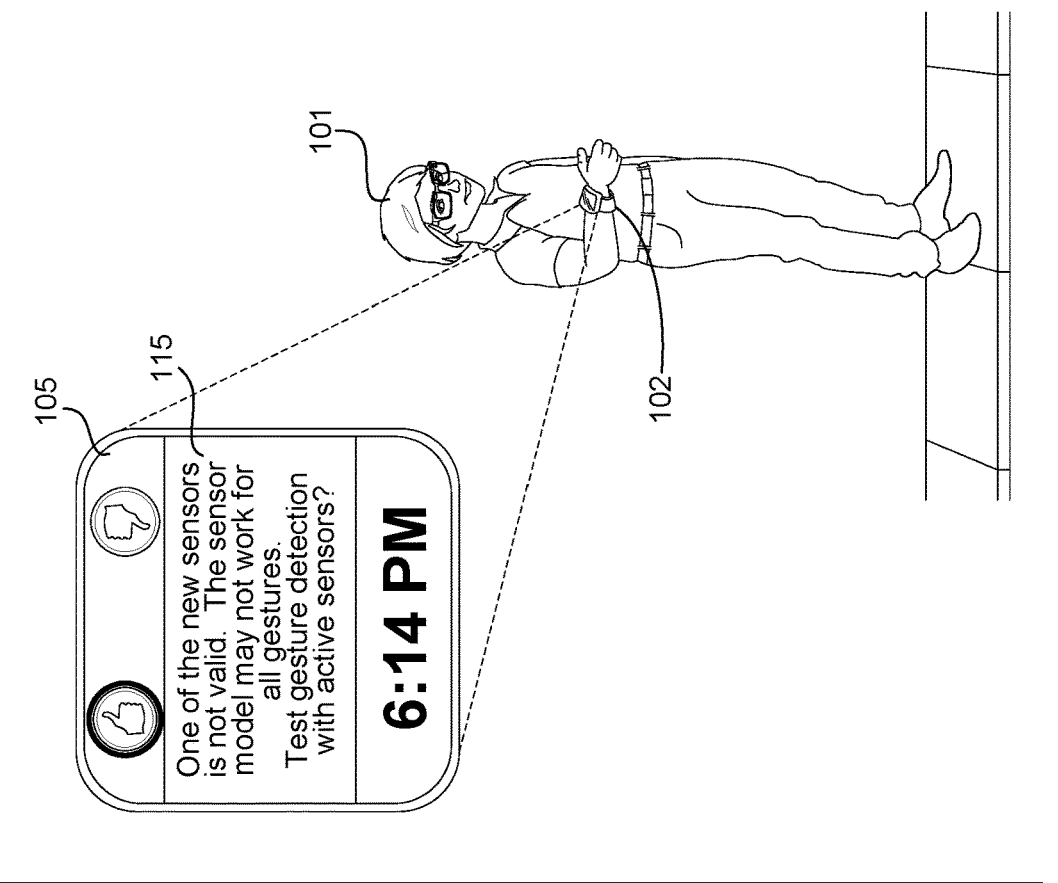
Figure 1D:
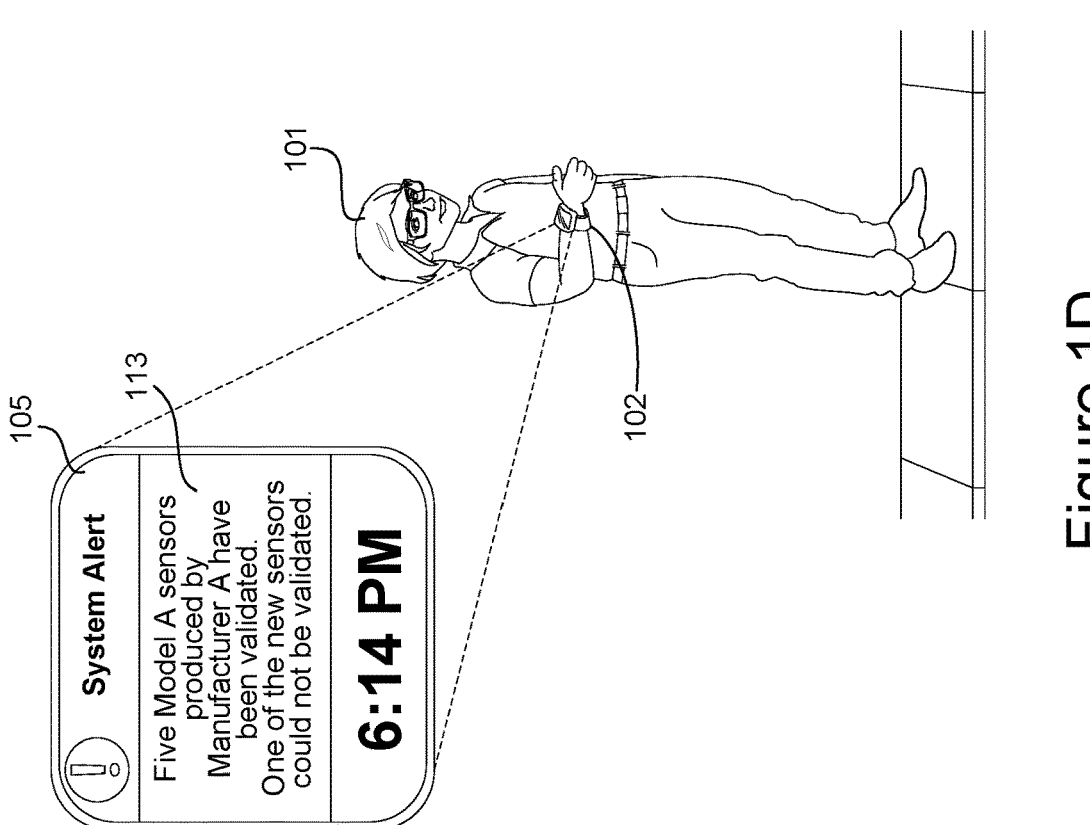

FIG. 1D shows the user 101 wearing the wrist-wearable device 102 after sensor validation has been performed at the wrist-wearable device (e.g., at a time subsequent to FIG. 1C). In some embodiments, signal preprocessing is performed at respective analog frontends (AFEs) of the neuromuscular-signal-sensing components of the wrist-wearable device 102 before validation occurs at another component of the wrist-wearable device 102 (e.g., a controller component as described in more detail with respect to FIGS. 3A-3B). The display 105 of the wrist-wearable device 102 is displaying a notification 113 in FIG. 1D that indicates the results of the validation performed at the wrist-wearable device 102. The notification 113 indicates that five sensors manufactured by a particular manufacturer (e.g., Manufacturer A) are present and validated, and that one of the neuromuscular-signal-sensing components (e.g., the neuromuscular-signal-sensing component 104 shown in FIG. 1A) could not be validated. In some embodiments, during validation of the neuromuscular-signal-sensing components, the wrist-wearable device 102 identifies one or more capabilities of the active neuromuscular-signal-sensing components of the wrist-wearable device 102. For example, capabilities of the neuromuscular-signal-sensing component are identified based on the make and/or model of the component. In some embodiments, the capabilities are identified based on encryption of the encrypted signal (e.g., the secret used to encrypt the signal corresponds to a particular type, make, and/or model of component).

In some embodiments, a notification may be generated for the user in accordance with one or more neuromuscular-signal-sensing components of the wrist-wearable device not being validated (e.g., the notification 113 displayed in FIG. 1D). In some embodiments, the notification includes a privacy warning for the user. In some embodiments, the notification includes identification of the neuromuscular-signal-sensing component (e.g., with an associated warning).

FIG. 1E shows the user 101 wearing the wrist-wearable device 102 after sensor validation has been performed (e.g., at a time subsequent to FIG. 1C). The display 105 of the wrist-wearable device 102 in FIG. 1E is displaying a notification 115 indicating that the sensor model used by the wrist-wearable device 102 may not work for all gestures in accordance with one of the neuromuscular-signal-sensing components not being validated by the wrist-wearable device 102 (the notification stating: "One of the new sensors is not valid. The sensor model may not work for all gestures. Test gesture detection with active sensors?"). In some embodiments, in accordance with one or more neuromuscular-signal-sensing components of the wrist-wearable device 102 being validated and/or not validated, the wrist-wearable device causes an adjustment to a machine-learning model based on one or more capabilities of the active neuromuscular-signal-sensing components of the wrist-wearable device 102. In some embodiments, the model is adjusted based on sensed characteristics of the user, e.g., skin tone, hair coverage, and the like. In some embodiments, the machine-learning model is adjusted based on a number and type of neuromuscular-signal-sensing components that are coupled to the controller component (e.g., the neuromuscular-signal-sensing component 104 shown in FIG. 1A). In some embodiments, a mode is selected/adjusted based on capabilities associated with each sensing component. For example, if each sensor has capabilities required for a first (e.g., complex) model, then the first model is selected. If one sensor does not have sufficient capabilities, then a second (e.g., simpler) model is selected. In this example, using the second model (as opposed to the first model) may limit which gestures can be detected. The particular model used may also affect power consumption and/or processing time for detecting gestures.

Figure 1G:
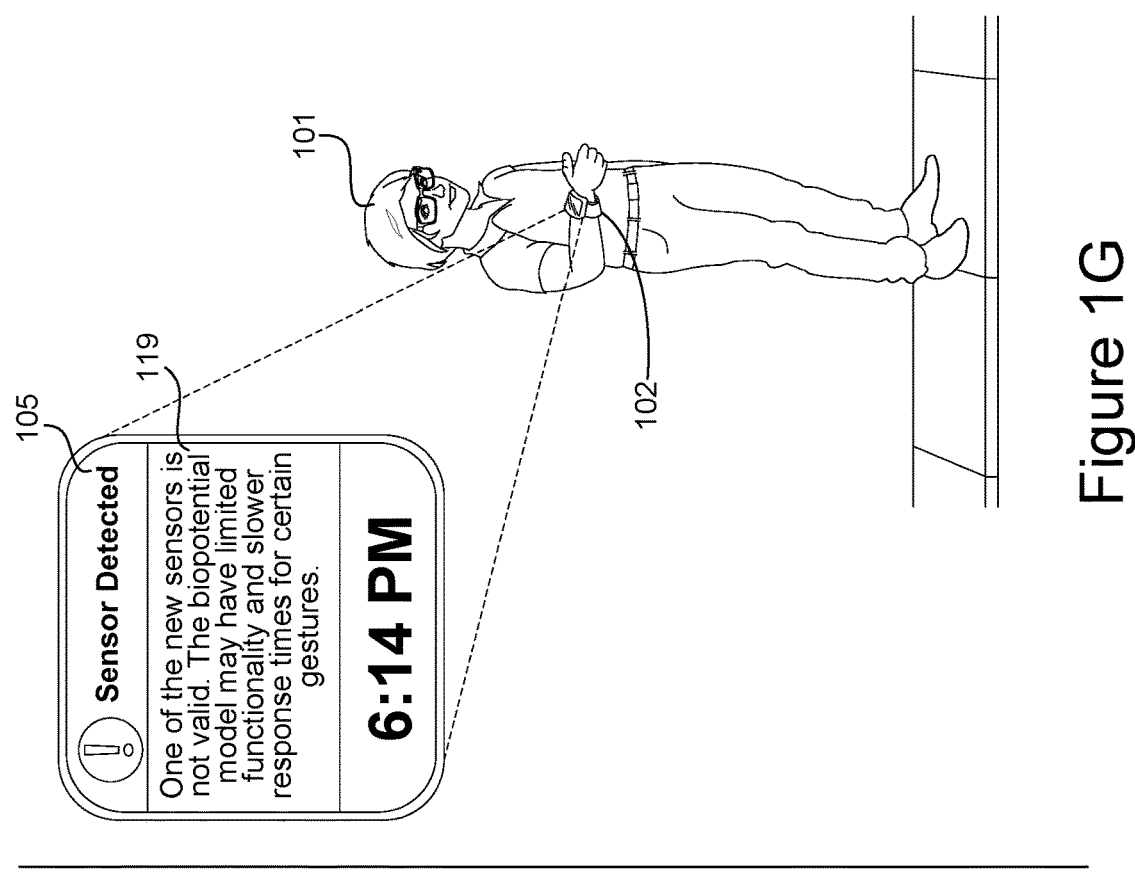
Figure 1F:
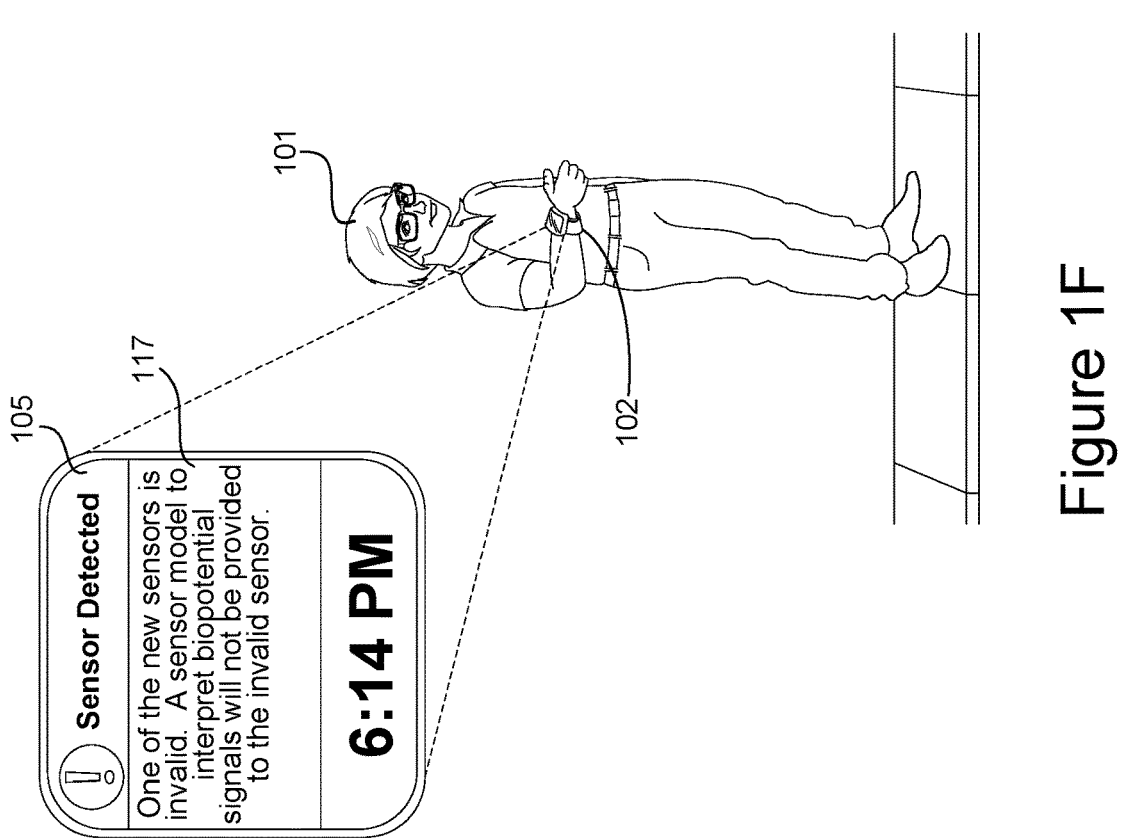

FIG. 1F shows the user 101 wearing the wrist-wearable device 102 after sensor validation has been performed (e.g., at a time subsequent to FIG. 1C). The display 105 of the wrist-wearable device 102 in FIG. 1F is displaying a notification 117 indicating that no sensor model will be provided in accordance with one of the neuromuscular-signal-sensing components of the wrist-wearable device 102 not being validated (stating: "One of the new sensors is invalid. A sensor model to interpret biopotential signals will not be provided to the invalid sensor."). In some embodiments, when each of the neuromuscular-signal-sensing components of the wrist-wearable device 102 is validated, a trained model (e.g., a machine-learning model) is provided to the neuromuscular-signal-sensing components of the wrist-wearable device 102 to allow for more efficient computation and/or processing of neuromuscular signals. In some embodiments, when one of the neuromuscular-signal-sensing components of the wrist-wearable device 102 is not validated, a trained model is not provided to the neuromuscular-signal-sensing components of the wrist-wearable device 102 (e.g., so the model is not susceptible to security risks associated with the unvalidated component).

In some embodiments, an operating mode of the wrist-wearable device 102 is activated based on the neuromuscular-signal-sensing components of the wrist-wearable device being validated. In some embodiments, the wrist-wearable device 102 forgoes activating the operating mode of the wrist-wearable device 102 in accordance with one or more neuromuscular-signal-sensing components (e.g., the neuromuscular-signal-sensing component 104 shown in FIG. 1A)

not being validated. In some embodiments, the wrist-wearable device 102 is disabled in accordance with a neuromuscular-signal-sensing component not being valid. In some embodiments, functionality of the wearable device is limited/restricted in accordance with a neuromuscular-signal-sensing component not being valid. For example, functionality requiring signals from the invalid component is disabled. As another example, functionality requiring capabilities not available with the invalid component is disabled.

FIG. 1G shows the user 101 wearing the wrist-wearable device 102 after sensor validation has been performed (e.g., at a time subsequent to FIG. 1C). The display 105 of the wrist-wearable device 102 is displaying a notification 119 in FIG. 1G indicating that a biopotential model of the wrist-wearable device 102 may have limited functionality and slower response times for particular gestures that the user 101 may perform, in accordance with one of the neuromuscular-signal-sensing components not being validated by the wrist-wearable device 102. In some embodiments, the wrist-wearable device forgoes activating an operating mode (e.g., use of a machine-learning model) based on one or more of the neuromuscular-signal-sensing components of the wrist-wearable device 102 not being validated. In some embodiments, a first model is used when all components are validated and a second model is used when one of the components is not validated.

As discussed previously, FIGS. 1E-1G illustrate example notifications provided to a user in accordance with a sensor component failing to validate (e.g., being invalid). In some embodiments, the user is provided with options for using an invalid component. For example, the options may include disabling the device until the invalid component is removed, accepting the security risks associated with using the invalid components, and/or limiting functionality of the device while the invalid component is installed. In some embodiments, an option is selected for the user based on one or more user preferences (e.g., from a user profile of the user). In some embodiments, the type of notification presented and/or operating state of the device is determined based on one or more user preferences.

Figures 2A, 2B:
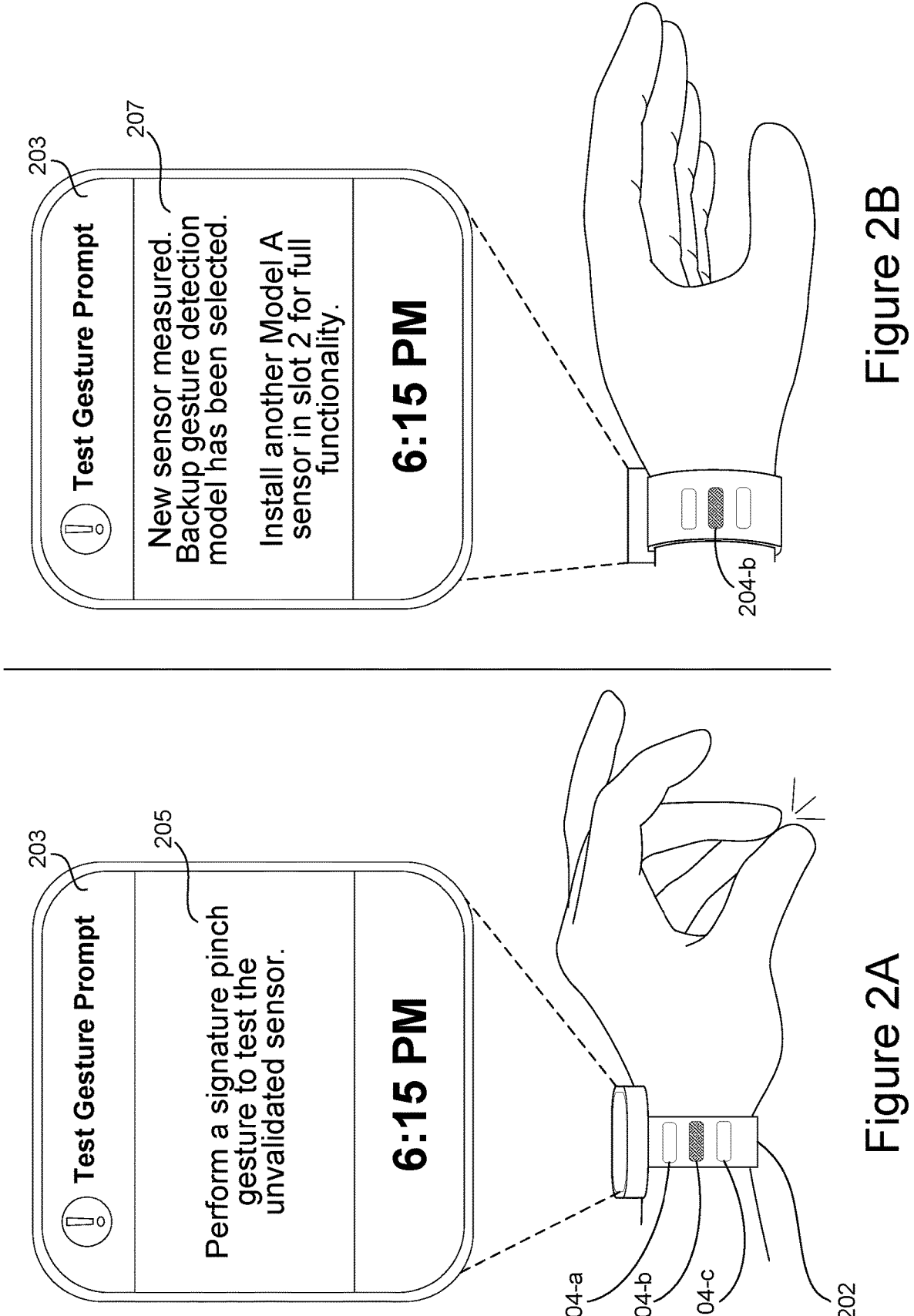
FIGS. 2A-2B show an example sequence of a wrist-wearable device detecting a gesture while an unvalidated neuromuscular-signal sensor is on the wrist-wearable device in accordance with some embodiments.

FIGS. 2A-2B show an example sequence of a wrist-wearable device detecting a gesture while an unvalidated neuromuscular-signal sensor is on the wrist-wearable device in accordance with some embodiments (e.g., subsequent to the user selecting an accept option in FIG. 1E). The example in FIGS. 2A-2B includes a user wearing a wrist-wearable device 202 (e.g., including some or all of the components of the wrist-wearable device 102 shown in FIGS. 1A-1G). The wrist-wearable device 202 in FIGS. 2A-2B includes a display 203 and a plurality of neuromuscular-signal-sensing components, including neuromuscular-signal-sensing components 204-a through 204-c. The plurality of neuromuscular-signal-sensing components include an unvalidated neuromuscular-signal-sensing component 204-b (e.g., not validated by a controller component of the wrist-wearable device 202).

In FIG. 2A, the user is performing a stacked pinch gesture that includes contact between the user's thumb and two of the user's fingers. The display 203 of the wrist-wearable device 202 shows an instruction 205 to perform a particular pinch gesture to test the unvalidated neuromuscular-signal-sensing component 204-b (stating: "Perform a signature pinch gesture to test the unvalidated sensor."). In some embodiments, the gesture used to test an unvalidated neuromuscular-signal-sensing component (e.g., a biopotential-signal sensor) can be selected based on a particular sensor-skin interface that the neuromuscular-signal-sensing component is associated with (e.g., located on or with a threshold proximity of).

In FIG. 2B, the user has released the pinch gesture, and the display 203 of the wrist-wearable device 202 is display- ing a notification 207 indicating to the user that a backup gesture model has been selected based on the result of the stacked pinched gesture (e.g., the quality of the detected biopotential signals). The notification 207 at the display 203 of the wrist-wearable device 202 states: "New sensor mea- sured. Backup gesture detection model has been selected. Install another Model A sensor in slot 2 for full functional- ity." That is, the wrist-wearable device 202 is caused to provide an indication to the user that replacing an unvali- dated neuromuscular-signal-sensing component would cause the wrist-wearable device 202 to have increased functionality (e.g., use a more functional gesture model). In some embodiments, the device prompts the user to replace the invalid component to have full functionality. In some embodiments, the device notifies the user that gesture- sensing functionality is disabled (or limited) while an invalid component is installed.

Figure 3A:
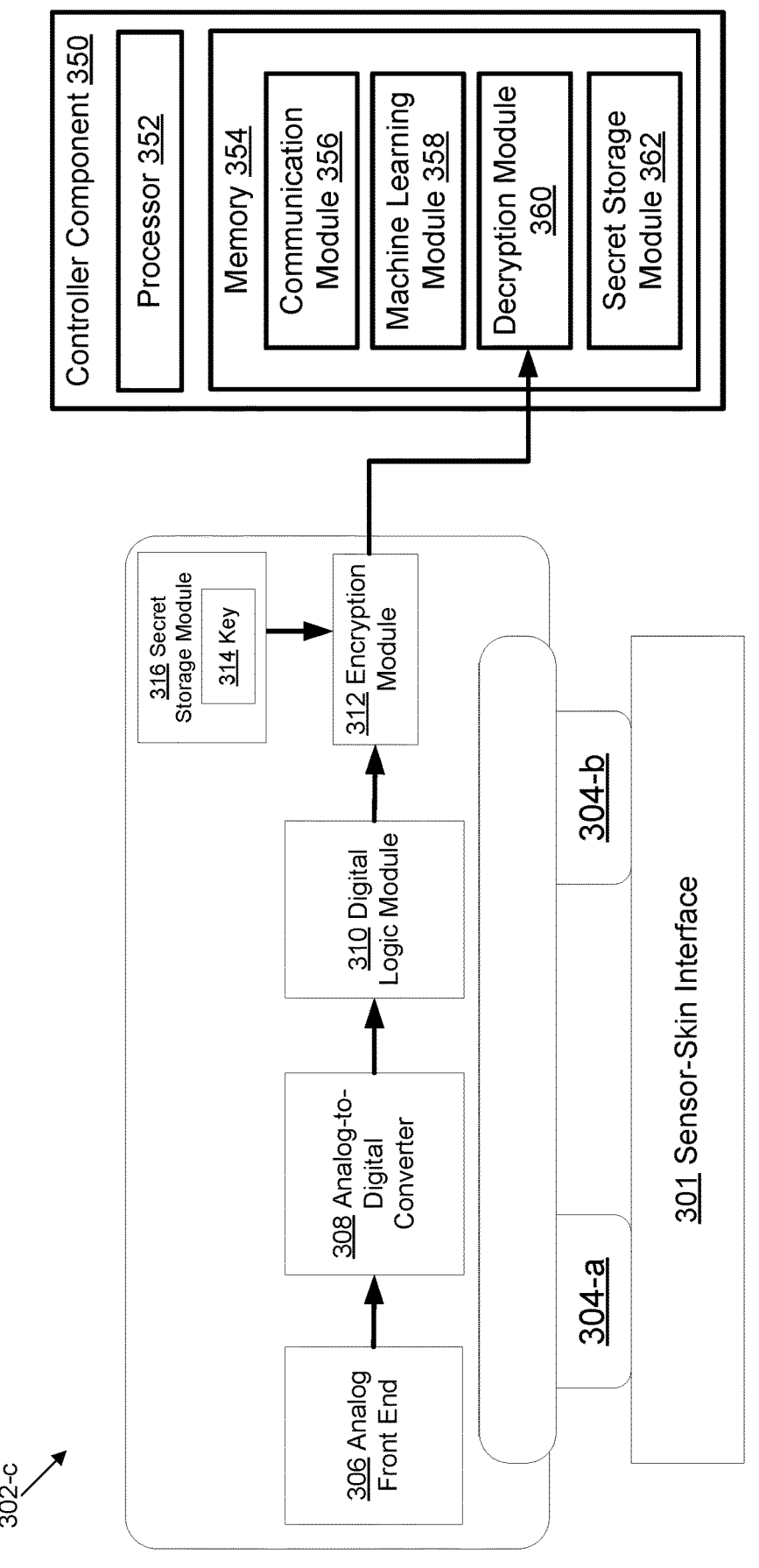
FIGS. 3A-3B show example components of a wearable device that includes neuromuscular-signal sensors in accordance with some embodiments.
Figure 3B:
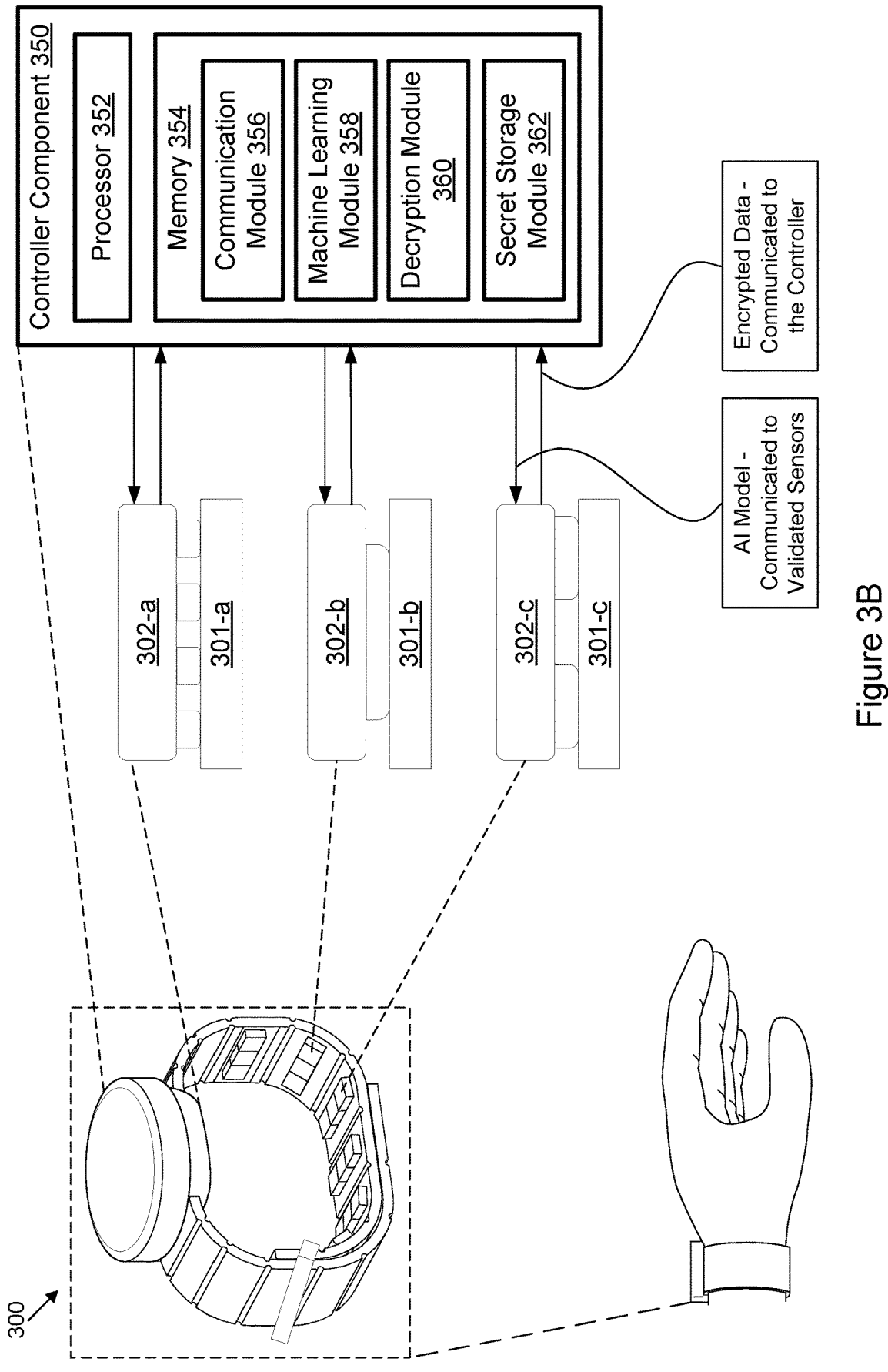

FIGS. 3A-3B show example components of a wearable device that includes neuromuscular-signal sensors in accor- dance with some embodiments. FIG. 3A shows a neuromus- cular-signal-sensing component 302-c, which may be the same or similar to one of the neuromuscular-signal-sensing components of the wrist-wearable device 102 shown in FIGS. 1A-1G and/or one of the neuromuscular-signal-sens- ing components of the wrist-wearable device 202 shown in FIGS. 2A-2B. The neuromuscular-signal-sensing compo- nent 302-c includes electrodes 304-a and 304-b (e.g., bio- potential-signal-sensing electrodes, such as EMG needle electrodes), which are configured to contact a sensor-skin interface 301. In some embodiments, the neuromuscular- signal-sensing component 302-c is specifically configured for a particular sensor-skin interface (e.g., a particular loca- tion of a bottom portion of a user's wrist, which may correspond to a specific muscle group of the user). In some embodiments, the sensor-skin interface 301 is skin/flesh of the user. In some embodiments, the sensor-skin interface 301 includes circuitry and/or components in the user's skin or flesh (e.g., a sensor tattoo). In some embodiments, the neuromuscular-signal-sensing component 302-c and the controller component 350 are components of the wrist- wearable device 300 shown in FIG. 3B.

The neuromuscular-signal-sensing component 302-c includes an AFE 306. The AFE 306 is configured to receive and process biopotential signals sensed by the electrodes 304-a and 304-b. In some embodiments, the analog frontend includes one or more analog amplifiers configured to amplify the biopotential signals sensed by the electrodes 304-a and 304-b. In some embodiments, the AFE 306 amplifies, buffers, and/or filters the biopotential signals sensed by the electrodes 304-a and 304-b. In some embodi- ments, the AFE 306 is configured for monopolar, pseudo- monopolar, and/or differential signal sensing.

The neuromuscular-signal-sensing component 302-c includes an analog-to-digital converter (ADC) 308 that is configured to receive analog information about the detected biopotential signals from the AFE 306 and convert the analog information to digital information. In some embodi- ments, the analog information is received via an electronic communication between the AFE 306 and the ADC 308.

In some embodiments, the neuromuscular-signal-sensing component 302-c includes a digital logic module 310 that is configured to receive digital information from the ADC 308 via an electronic communication. The digital logic module 310 is configured to process the digital information from the ADC 308 prior to sending the data to a controller component 350. In some embodiments, the digital logic module 310 is configured to discard portions of the biopotential data not associated with a particular gesture. In some embodiments, the digital logic module 310 includes a pre-processing model. In some embodiments, the pre-processing model is configured to detect potential gestures and send the data corresponding to the potential gestures to the controller component 350 (e.g., discarding data that does not corre- spond to a potential gesture). In this way, less data needs to be encrypted, transmitted, and decrypted as compared to a system with no pre-processing. For example, in some embodiments, the digital logic module 310 is configured to simplify (e.g., flatten) aspects of the digital information to minimize the processing time required to encrypt the digital information.

The neuromuscular-signal-sensing component 302-c includes an encryption module 312 that is configured to receive and encrypt digital information associated with the biopotential signals detected by the electrodes 304-a and 304-b. In some embodiments, the encryption module 312 receives digital information from the digital logic module 310. In some embodiments, the encryption module 312 receives digital information from the ADC 308, without the digital information being further processed (e.g., by a digital logic module). In some embodiments, the encryption mod- ule 312 is specific to a particular manufacturer and/or a model manufactured by a particular manufacturer. The encryption module 312 is also configured to receive infor- mation about a key 314 (e.g., a shared secret), which may be provided to the neuromuscular-signal-sensing component 302-c by a manufacturer or retailer. In some embodiments, the encryption module 312 is further configured to decrypt information received from the controller component 350 (e.g., models and configuration data).

In some embodiments, the key 314 is received from the controller component 350 (e.g., updated by the controller component after initial validation of the sensing compo- nent). In some embodiments, the key 314 is stored at a secret storage module 316 for use in conjunction with subsequent encryption operations. In some embodiments, the secret storage module 316 is a submodule of the encryption module 312. In some embodiments, the key 314 is used by the controller component 350 to determine sensor capabili- ties of the neuromuscular-signal-sensing component 302-c. In some embodiments, the key 314 is embedded in the neuromuscular-signal-sensing component 302-c silicon.

In some embodiments, some, or all of the components of the neuromuscular-signal-sensing component 302-c (e.g., the electrodes 304-a and 304-b, the AFE 306, the ADC 308, the digital logic module 310, and the encryption module 312) are included on an electrode silicon, which may be enclosed in a housing (e.g., a carrier component). In some embodiments, the neuromuscular-signal-sensing component 302-c includes a carrier component that may be machined after electrodes are coupled with the carrier component, such that electrodes and the carrier component form a smooth outer profile. In some embodiments, the shape profile of the carrier component is selected from a group consisting of a stadium shape, a discorectangle shape, a sausage shape, a pill shape, a squectangle, and an obround. In some embodi- ments, one or more secrets and/or keys are embedded into the electrode silicon and/or the carrier component of the neuromuscular-signal-sensing component 302-c.

In some embodiments, the carrier component is configured to hold two or more neuromuscular-signal contact points (e.g., the electrodes 304-a and 304-b). The carrier component is configured to electrically separate the two neuromuscular-signal contact points from one another. In some embodiments, each of the two neuromuscular-signal contact points extend above a skin-facing portion of the wearable device (e.g., a wrist-facing portion of the wrist-wearable device 102), such that when the wearable device is worn, each of the two neuromuscular-signal contact points impinges the outer surface of a user's skin by a predetermined skin depression depth. In some embodiments, the opposite side of the carrier component includes coupling mechanisms (e.g., snap fittings) that are configured to couple the carrier component to a particular wearable device.

In some embodiments, coupling the carrier component to a wearable device causes the carrier component to become communicatively coupled to the controller component 350 of the wearable device. In some embodiments, when the controller component 350 and/or the neuromuscular-signal-sensing component 302-c boots up, the wearable device detects whether any sensors of the wrist-wearable device require validation. In some embodiments, this causes an encrypted signal to be transmitted from the neuromuscular-signal-sensing component to the controller component based on (e.g., in response to) the carrier component being coupled with the wearable device.

The controller component 350 can be part of the same wearable device and/or wearable structure that includes the neuromuscular-signal-sensing component 302-c. The controller component may include one or more processors 352 and memory 354. The memory 354 may be configured to include instructions, which, when executed by the controller component 350, cause the controller component 350 to perform one or more operations related to detecting, processing, analyzing, interpreting, and/or responding to neuromuscular signals.

In some embodiments, the memory 354 includes a communication module 356 configured to allow the controller component 350 to communicate with a remote server system and/or one or more neuromuscular-signal-sensing components, such as the neuromuscular-signal-sensing component 302-c. In some embodiments, the controller component 350 is configured to receive data from each (or at least a subset of two or more) of a plurality of neuromuscular-signal-sensing components (e.g., the neuromuscular-signal-sensing components 302-a, 302-b, and 302-c shown in FIG. 3B), and process the data from the plurality of sensors to determine whether the user is performing an identifiable gesture (e.g., a gesture that corresponds to a function of the wearable device).

In some embodiments, the controller component 350 includes a machine-learning module 358 that is configured to apply machine learning to data from one or more neuromuscular-signal-sensing components, to obtain an inference related to the data. For example, the machine-learning module 358 may be used to determine if a user is performing an identifiable gesture (e.g., a thumbs-up gesture, a pinch gesture), including a gesture that corresponds to an active state of the device (e.g., a gesture corresponding to a function of a user interface that is currently being displayed). In some embodiments, the machine-learning module 358 is configured to use data from less than all of the neuromuscular-signal-sensing components that the controller component 350 is receiving data from, which may be based on a signal-to-noise ratio that is determined based on values of respective data received from the neuromuscular-signalsensing components. In some embodiments, the controller component 350 is configured to provide (e.g., via the communication module 356) data associated with the machine-learning module 358 to one or more neuromuscular-signal-sensing components that are in electronic communication with the controller component 350. For example, the machine-learning model may provide a trained classifier generated based on historical data associated with a user to newly validated neuromuscular-signal-sensing components of a wearable device, which may provide more accurate sensing and/or gesture recognition with respect to the particular user. Such provisioning of data associated with the machine-learning module can allow for improved efficiency of a man-machine interface, by reducing latency caused by inter-component communication of data related to sensed neuromuscular signals.

In some embodiments, the controller component 350 includes a decryption module 360 that is configured to decrypt and/or validate encrypted data received from one or more neuromuscular-signal-sensing components of a wearable device. In some embodiments, the decryption module 360 includes instructions to determine whether data is encrypted (e.g., before attempting to validate the encryption of the data). In some embodiments, the decryption module 360 compares the encryption to a key and/or secret of a common encryption scheme associated with the decryption module 360 (e.g., after determining that the data is encrypted). For example, the common encryption scheme may be based on a manufacturer-supplied secret key that is used to encrypt data for a plurality of components provided by the manufacture, or all components of a particular model supplied by the manufacturer. In some embodiments, a key and/or secret is stored in a secret storage module 362 in the memory 354 of the controller component 350. In some embodiments, the controller component includes a database and/or other structured data (e.g., a table) that includes a plurality of keys associated with a plurality of sensor manufacturers, and upon receiving encrypted signals from one or more neuromuscular-signal-sensing components of the wrist-wearable device, the controller component checks whether a key used to encrypt the signal data is stored in the database or other structured data. In some embodiments, the controller component 350 communicates (e.g., via the communication module 356) with a remote server to update a register of validated manufacturers and/or shared secrets/keys. In some embodiments, each manufacturer is associated with a single secret and/or key. In some embodiments, each manufacturer is associated with a range of secrets and/or keys. In some embodiments, manufacturers update their associated keys (e.g., on a periodic basis), and provide the updated keys to the controller component 350 via communication with the remote server. In some embodiments, a same key is used by each sensor manufactured by a particular manufacturer, and the data of each sensor is encrypted based on a serial number associated with the sensor. In some embodiments, the controller component 350 is configured to detect a serial number for each sensor that is coupled with the wrist-wearable device 300, and the controller component validates each sensor of the wrist-wearable device 300 by utilizing the database of validated keys in conjunction with a register of serial addresses.

In some embodiments, the decryption module 360 includes an encryption component. In some embodiments, the controller component 350 includes an encryption component that is distinct from the decryption module 360. In some embodiments, the encryption component is configured to encrypt signals sent to the neuromuscular-signal-sensing components. For example, the encryption component is configured to identify a shared secret for a particular sensing component and use the shared secret to encrypt communications to the sensing component. In this way, communications from the controller component 350 to the sensing components are also secured against man-in-the-middle attacks and other malicious actors.

FIG. 3B shows the wrist-wearable device 300 including the plurality of neuromuscular-signal-sensing components 302-a, 302-b, and 302-c, which are located at discrete locations of the wrist-wearable device 300. In some embodiments, each of the neuromuscular-signal-sensing components 302-a, 302-b, and 302-c is specifically designed and/or configured to detect biopotential signals at different sensor-skin interfaces of a user (e.g., sensor-skin interfaces 301-a, 301-b, and 301-c), which may be different locations along a circumference of a user's wrist. In some embodiments, each of the neuromuscular-signal-sensing components has distinct physical components (e.g., different numbers of electrodes configured to contact the respective sensor-skin interface associated with the electrode). In some embodiments, the distinct physical components are based on the features of the part of body where they are configured to be located while sensing neuromuscular signals. In some embodiments, the distinct physical components are based on sensing capabilities provided by the neuromuscular-signal-sensing components. In some embodiments, a different artificial intelligence model is used by each neuromuscular-signal sensor, and/or by subsets of a set of neuromuscular-signal sensors of the wrist-wearable device. In some embodiments, one or more biopotential-signal-sensing components of a wearable device are configured to sense multiple distinct types of biopotential signals (e.g., dual-purpose sensors for detecting EMG and photoplethysmography (PPG) signals).

In some embodiments, each of the neuromuscular-signal-sensing components 302-a through 302-c is configured to communicate with the controller component 350 via a flexible printed circuit (FPC) that is distributed along an inner band portion of the wrist-wearable device 300. In some embodiments, the FPC is configured to provide encrypted signals from each of the neuromuscular-signal-sensing components of the wrist-wearable device 300 to the controller component 350. In some embodiments, the FPC is configured to provide one or more trained artificial intelligence (AI) models (e.g., machine-learning models) and/or constituent components (e.g., data) thereof to one or more respective sensors of the wearable device. For example, a first machine-learning model may be provided to the neuromuscular-signal-sensing component 302-a based on a first determination that the neuromuscular-signal-sensing component 302-a is validated (and/or a determination that the neuromuscular-signal-sensing component 302-a has a particular set of capabilities). In this example, a second machine-learning model may be provided to the neuromuscular-signal-sensing component 302-b based on a second determination that the neuromuscular-signal-sensing component 302-b is validated (and/or has a second set of capabilities). In some embodiments, one or more of the neuromuscular-signal-sensing components 302-a through 302-c is communicatively coupled to the controller component 350 via an FPC, bus, or other wired connection.

Figure 4:
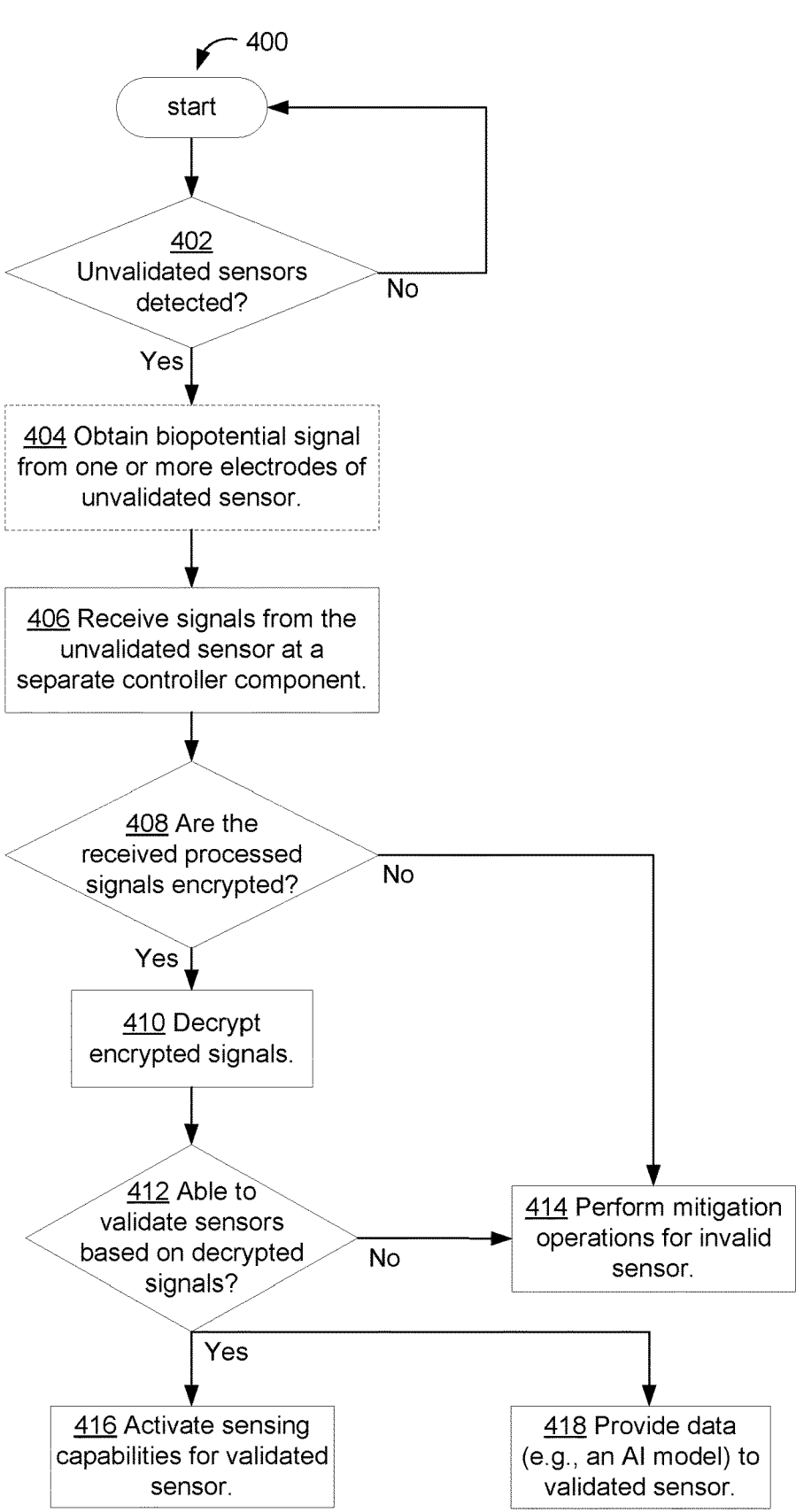
FIG. 4 shows a logical flow diagram of an example method for providing data integrity for neuromuscular signals detected by a neuromuscular-signal sensor of a wearable device in accordance with some embodiments.

FIG. 4 shows an example logical flow diagram of a method 400 for providing data integrity for biopotential signals detected by a biopotential-signal sensor of a device in accordance with some embodiments. In some embodiments, the device is a wearable device such as the wrist-wearable devices 102, 202 and 300. In some embodiments, the device is a stationary or mobile device configured to detect biopotential signals from a user. In some embodiments, the biopotential-signal sensor is a neuromuscular-signal sensor (e.g., an EMG sensor). In some embodiments, the method 400 is performed by a controller component (e.g., the controller component 350) of the device.

Performance of the method 400 includes detecting (402) whether there are any unvalidated sensors communicatively coupled to the device. In some embodiments, the device is configured to determine if there are unvalidated sensors based on detecting a sensor being coupled to the wearable device (e.g., a new sensor being coupled to the device for the first time). For example, respective slots (or other interface features) of the device may be configured to receive neuromuscular-signal-sensing components and to trigger detection by the device in response to a new neuromuscular-signal-sensing component being attached or otherwise communicatively coupled with the device. For example, the display 105 of the wrist-wearable device 102 displays a notification 107 in FIG. 1A indicating that a new sensor has been installed at the wrist-wearable device 102. In some embodiments, a controller component of the device (e.g., the controller component 350 in FIG. 3A) detects whether there are unvalidated sensors during a bootup process (e.g., when the controller component 350 is powered on and/or activated). In some embodiments, the method 400 is continually performed by the device while it is powered on, and the device continues (402, No) to detect whether there are any unvalidated sensors. In some embodiments, the device is configured to periodically or intermittently determine whether any unvalidated sensors are communicatively coupled. In some embodiments, the device is configured to determine whether any unvalidated sensors are communicatively coupled in response to particular events (e.g., a power-on event, a sensor coupling event, and/or an activation event).

In some embodiments, in accordance with detecting (402, Yes) an unvalidated sensor (e.g., the neuromuscular-signal-sensing component 104 shown in FIG. 1A) communicatively coupled to the device, the method 400 includes obtaining (404) a biopotential signal from one or more electrodes of the unvalidated sensor. For example, the wrist-wearable device 102 is displaying the notification 111 in FIG. 1C indicating that neuromuscular-signal sensors have been detected and that the active sensors are being validated based on the biopotential signals detected by the sensors of the wearable electronic device.

The method 400 includes receiving (406), at a controller component (e.g., the controller component 350), signals from the unvalidated sensor. In some embodiments, the signals from the unvalidated sensor include one or more processed biopotential signals associated with biopotential signals detected by the electrode(s) of the unvalidated sensor. For example, the unvalidated sensor amplifies, filters, and/or converts the detected biopotential signals to generate processed biopotential signals and sends the processed biopotential signals to the controller component. In some embodiments, in accordance with detecting an unvalidated sensor communicatively coupled to the device, the method includes receiving, at the controller component, a non-biopotential signal from the unvalidated sensor (e.g., a handshake, control, or test signal). For example, the device may be configured to validate the unvalidated sensor before receiving any biopotential information from the unvalidated sensor. In some embodiments, signals from the unvalidated sensor are received via a communication module (e.g., the communication module 356) of the controller component.

The method 400 includes determining (408) whether the received signals from the unvalidated sensor are encrypted. For example, when data associated with the neuromuscular-signal sensors are received from the neuromuscular-signal-sensing component 302-*c* by the controller component 350 in FIG. 3A, the controller component 350 may first determine whether the received data is encrypted before decrypting/validating the received data (e.g., using the decryption module 360). In some embodiments, a sensor sending unencrypted signals is determined to be invalid based on the lack of encryption. For example, to protect user privacy and enhance security, sensors communicating with the controller component of the device are required to encrypt data.

In accordance with a determination (408, Yes) that the received signals are encrypted, the method 400 includes decrypting (410) the encrypted signals (e.g., via the decryption module 360 shown in FIGS. 3A-3B).

After decrypting the received signals, the method 400 includes determining (412) whether the device (e.g., a controller component of the device) is able to validate the unvalidated sensor based on the decrypted signals. For example, the wrist-wearable device 102 is displaying a notification in FIG. 1D indicating that five sensors of the wrist-wearable device 102 are validated as being Model A sensors manufactured by the Manufacturer A, and that one of the sensors of the wrist-wearable device 102 is not validated (e.g., the controller component does not include information related to a secret and/or key used to encrypt the data provided to the unvalidated sensor). In some embodiments, the validation process includes identifying a shared secret used by the sensor to encrypt the data. In some embodiments, the validation process includes identifying a serial number of the sensor in the decrypted data, and validating the sensor based on the serial number.

In accordance with validating the unvalidated sensor (412, Yes) the method includes one or more of (i) activating (416) sensing/processing capabilities for the validated sensor, and (ii) providing (418) data (e.g., an AI model and/or configuration settings) to the validated sensor. In some embodiments, the data is provided to the validated sensor via an FPC of the wearable device. For example, the AI model is provided to the neuromuscular-signal-sensing component 302-*c* in FIG. 3B in accordance with the neuromuscular-signal-sensing component 302-*c* being validated by the controller component 350. In accordance with validating the unvalidated sensor (412, Yes) the method includes designating the unvalidated sensor as a valid sensor (e.g., and then setting up and/or configuring the sensor accordingly).

In accordance with either (i) a determination that the received signals are not encrypted (408, No), or (ii) the device being unable to validate the decrypted signals (412, No), the device performs (414) one or more mitigation operations for the invalid sensor. For example, as shown in FIGS. 2A-2B, the device can prompt a user to perform test gestures (e.g., the stacked pinch gesture shown in FIG. 2A) to determine whether the test gestures can be properly detected using the invalid sensor. In accordance with either (i) a determination that the received signals are not encrypted (408, No), or (ii) the device being unable to validate the decrypted signals (412, No), the unvalidated sensor is designated as an invalid sensor (e.g., and then disabling or configuring the sensor accordingly).

In some embodiments, the one or more mitigation operations include providing a notification to a user of the device that one or more sensors of the device are not validated. For example, each of the notifications at the display 105 of the wrist-wearable device 102 in FIGS. 1E-1G indicates to the user that one of the neuromuscular-signal-sensing components (e.g., the neuromuscular-signal-sensing component 104) could not be validated by the controller component of the wrist-wearable device 102 (e.g., the neuromuscular-signal-sensing component is designated as invalid).

In some embodiments, a mitigation operation includes prompting a user to perform test gestures to determine whether the device is able to detect some, or all, gestures performed by the user. For example, FIG. 1E shows the wrist-wearable device 102 displaying a notification 115 indicating that the user 101 can perform test gestures (such as the test gesture shown in FIG. 2A) to determine whether the active sensors can properly detect a particular gesture.

Other mitigation operations are illustrated by FIGS. 1F-1G. For example, as shown by FIG. 1F, no sensor models may be generated, used, and/or distributed based on one of the neuromuscular-signal-sensing components being invalid. For example, EMG functionality of the device may be disabled or restricted based on any of the neuromuscular-signal-sensing components of the wearable electronic device being unvalidated. FIG. 1G illustrates another example where the wearable electronic device may generate, use, and/or distribute a model having limited functionality and/or slower response times based on one or more of the neuromuscular-signal-sensing components being unvalidated. For example, a model, such as a machine-learning model, may be provided to each of the validated neuromuscular-signal-sensing components. Using the model allows the neuromuscular-signal-sensing components to analyze (e.g., pre-process) at least some of the biopotential signals locally (e.g., without needing to communicate with the controller component). For example, use of the model may allow the sensing components to perform at least some gesture recognition locally.

In some embodiments, the mitigation operations include restricting communications with the sensor from including any personally identifiable information. In some embodiments, the mitigation operations include disabling the invalid sensor (e.g., forgo providing power to the invalid sensors) and/or disabling communications with the invalid sensor. In some embodiments, the mitigation operations include performing gesture recognition without using biopotential information from the invalid sensor. For example, a gesture recognition model that does not use the biopotential information from the invalid sensor is selected and used for subsequent gesture recognition.

Example Embodiments

FIGS. 5A-5B show a method 500 for providing data integrity for neuromuscular signals detected by a neuromuscular-signal sensor of a wearable device in accordance with some embodiments. The method 500 is performed (502) at least in part by a neuromuscular-signal-sensing component (e.g., the neuromuscular-signal-sensing component 104 shown in FIG. 1A) of a wearable device (e.g., the wrist-wearable device 102). In some embodiments, some or all of the operations of the method 500 are performed (e.g., concurrently) at each of a plurality of neuromuscular-signal-sensing components communicatively coupled to the wearable device (e.g., each of the neuromuscular-signal-sensing components 302-*a*, 302-*b*, and 302-*c* shown in FIG. 3B).

(A1) The method 500 includes detecting (504) a neuromuscular signal via one or more electrodes (e.g., electrodes of any of the neuromuscular-signal-sensing components 302-*a*-302-*c* shown in FIG. 3B). In some embodiments, an analog frontend of the neuromuscular sensing component (e.g., the AFE 306 in FIG. 3A) obtains, processes, and/or stores the neuromuscular signal from the one or more electrodes. In some embodiments, the AFE amplifies and/or filters the neuromuscular signal. In some embodiments, the AFE performs monopolar, pseudo-monopolar, and/or differential sensing on the neuromuscular signal. The method 500 includes generating (506) a digital signal by converting the neuromuscular signal (e.g., via the ADC 308 in FIG. 3A). The method 500 includes generating (508) an encrypted signal by encrypting the digital signal. For example, the encryption module 312 of the neuromuscular-signal-sensing component 302-*c* shown in FIG. 3A is configured to encrypt signals from the ADC 308. The method 500 includes transmitting (510) the encrypted signal to a controller component of the wearable device, the controller component being distinct from the neuromuscular-signal-sensing component. For example, FIGS. 3A-3B illustrate encrypted signals being sent from each respective neuromuscular-signal-sensing component 302-*a*, 302-*b*, and 302-*c* to the controller component 350. In some embodiments, the encrypted signals are transmitted via an FPC that is configured to electronically couple each of the neuromuscular-signal-sensing components to the controller component 350. Although the method 500 describes neuromuscular signals and neuromuscular-signal sensors, one of ordinary skill in the art will recognize that the operations of the method 500 are applicable to other types of biopotential signals.

In some embodiments, the neuromuscular-signal-sensing component (or other biopotential-signal-sensing component) is configured to transmit an encrypted signal that does not include biopotential information such as a control signal, a handshake signal, or a test signal. In some embodiments, the neuromuscular-signal-sensing component (or other biopotential-signal-sensing component) is configured to transmit a device identifier (e.g., a serial number) via the encrypted signal.

In some embodiments, the neuromuscular-signal-sensing component does not detect/process neuromuscular signals until validated and/or enabled by the controller component. In some embodiments, the neuromuscular-signal-sensing component is configured to transmit the encrypted signal in response to an activation event (e.g., a power-on event, a bootup event, or an enablement event). In some embodiments, the neuromuscular-signal-sensing component (or other biopotential-signal-sensing component) is configured to transmit the encrypted signal in response to a signal from the controller component (e.g., as part of a validation process and/or handshake process).

(A2) In some embodiments of A1, the neuromuscular-signal-sensing component and the controller component are arranged on a same wrist-wearable device (e.g., the wrist-wearable device 102, which may include some or all of the components of the other wearable devices described herein). In some embodiments, the neuromuscular-signal-sensing component and the controller component are communicatively coupled via a wired connection (e.g., a flexible printed circuit board).

(A3) In some embodiments of any of A1-A2, the wearable device includes one or more additional neuromuscular-signal-sensing components, and each additional neuromuscular-signal-sensing component includes a respective encryption component. For example, FIG. 3B shows the wrist-wearable device 300 including the neuromuscular-signal-sensing components 302-*a*, 302-*b*, and 302-*c*. In some embodiments, each neuromuscular-signal-sensing component is arranged on the wearable device so as to measure separate motor units of a user. In some embodiments, the wearable device includes a plurality of biopotential-signal sensors arranged to contact distinct portions of the user's body. In some embodiments, the wearable device recognizes user gestures by aggregating biopotential data (e.g., neuromuscular data) from multiple biopotential-signal-sensing components. In some embodiments, each biopotential-signal-sensing component stores an associated secret or key and encrypts communications using the stored secret or key.

(A4) In some embodiments of any of A1-A3, the neuromuscular-signal-sensing component comprises the one or more electrodes, an AFE, an ADC, and encryption logic. For example, neuromuscular-signal-sensing component 302-*c* shown in FIG. 3A includes the electrodes 304-*a* and 304-*b*, the analog frontend 306, the ADC 308, and the encryption module 312. In some embodiments, the neuromuscular-signal-sensing component includes a digital logic module (e.g., the digital logic module 310).

In some embodiments, the digital logic module is configured to analyze (e.g., pre-process) neuromuscular data (e.g., the digital signals from the ADC). In some embodiments, the digital logic module is configured to reduce data provided by the analog-to-digital converter so that the data can be encrypted by the encryption module more quickly and efficiently. In some embodiments, the digital logic module is configured to identify neuromuscular signals that correspond to recognized gestures and/or potential gestures and discard neuromuscular signals that do not correspond to recognized gestures and/or potential gestures. In some embodiments, the digital logic module provides the neuromuscular signals that correspond to recognized gestures and/or potential gestures to the encryption module and does not provide neuromuscular signals that do not correspond to recognized gestures and/or potential gestures to the encryption module.

(A5) In some embodiments of A4, the analog frontend, the analog-to-digital converter, and the encryption logic are arranged on electrode silicon coupled to the one or more electrodes, and the electrode silicon is enclosed in a housing. For example, the neuromuscular-signal-sensing component 302-*c* can be part of an electrode pill that includes the analog frontend 306, the ADC 308, and the encryption module 312, each arranged on a same electrode silicon layer enclosed within a housing (e.g., a carrier component), and the electrode silicon layer can be coupled to the electrodes 304-*a* and 304-*b*. In some embodiments, the electrode pill is configured to be removably inserted in (or otherwise connected to) the wearable device. In some embodiments, the wearable device is configured to allow removal/replacement of electrode pills by the user. The use of replaceable (modular) electrode pills allows the user to replace faulty or broken electrode pills and/or replace existing electrode pills with ones that have increased functionality and/or improved operational characteristics.

(A6) In some embodiments of any of A1-A5, the method 500 further includes operations performed at (512) the controller component (e.g., the controller component 350) of the wearable device. The method 500 further includes receiving (514) the encrypted signal from the neuromuscular-signal-sensing component. The method 500 further includes generating (516) a decrypted signal by decrypting the encrypted signal. The method 500 further includes validating (518) the neuromuscular-signal-sensing component based on the decrypted signal. In some embodiments, the controller component does not validate the neuromuscular-signal-sensing component in accordance with the decryption operation failing. In some embodiments, the controller component does not validate the neuromuscular-signal-sensing component in accordance with an incoming signal not being encrypted. For example, the memory 354 of the controller component 350 in FIG. 3A can include one or more programs (e.g., as part of the communication module 356) that are configured to communicate with the neuromuscular-signal-sensing component 302-c, and collect encrypted data associated with neuromuscular signals. In some embodiments, the controller component is arranged in a capsule or watch body (e.g., the watch body 654 described below with respect to FIG. 6A). In some embodiments, the neuromuscular-signal-sensing component is arranged on a watch band (e.g., the watch band 662 described below with respect to FIG. 6A).

(A7) In some embodiments of A6, validating the neuromuscular-signal-sensing component includes identifying one or more capabilities of the neuromuscular-signal-sensing component (e.g., a manufacturer and/or model of the neuromuscular-signal-sensing component as illustrated by FIG. 1D). In some embodiments, the capabilities of the neuromuscular-signal-sensing component are identified based on an identifier of the neuromuscular-signal-sensing component (e.g., the identifier received from the neuromuscular-signal-sensing component). In some embodiments, the capabilities of the neuromuscular-signal-sensing component are identified based on the shared secret used by the neuromuscular-signal-sensing component. For example, a particular key is only used for sensors having a particular set of capabilities (e.g., a particular model of sensors) and thus the set of capabilities can be identified via use of the key.

(A8) In some embodiments of any of A6-A7, the method 500 further includes, in accordance with the neuromuscular-signal-sensing component not being validated, generating (520) a notification for a user of the wearable device (e.g., any of the notifications 113, 115, 117, and 119 shown in FIGS. 1D-1G, which may be part of the mitigation operations described with respect to the mitigation operations in step 414 of FIG. 4). In some embodiments, the notification includes indication of the security and/or privacy risks associated with use of an invalid sensor component.

(A9) In some embodiments of A6-A8, the method 500 further includes, in accordance with the neuromuscular-signal-sensing component being validated, adjusting (522) a machine-learning model based on one or more capabilities of the neuromuscular-signal-sensing component. In some embodiments, adjusting the machine-learning model includes modifying the model (or inputs to the model) so as to not use biopotential information from the invalid sensing component. In some embodiments, a model that does not use biopotential information from the invalid sensing component is selected for use in accordance with the neuromuscular-signal-sensing component being validated.

In some embodiments, the method 500 further includes, after adjusting the machine-learning model, sending (524) the machine-learning model to the neuromuscular-signal-sensing component. For example, the controller component 350 in FIG. 3B provides one or more artificial intelligence models to each of the neuromuscular-signal-sensing components 302-a, 302-b, and 302-c, after validating the respective neuromuscular-signal-sensing components using the decryption module 360. In some embodiments, different models are provided to different neuromuscular-signal-sensing components (e.g., based on whether the individual components are validated and/or the capabilities of the individual components).

(A10) In some embodiments of A6-A9, the method 500 further includes receiving (526) a signal from an additional neuromuscular-signal-sensing component. For example, the controller component 350 shown in FIG. 3B is receiving signals from each of the neuromuscular-signal-sensing components 302-a, 302-b, and 302-c. In some embodiments, the additional neuromuscular-signal-sensing component includes a different set of subcomponents/modules than the neuromuscular-signal-sensing component (e.g., has a different number of electrodes, different digital logic, and/or different encryption components). In some embodiments, the additional neuromuscular-signal-sensing component is configured to detect biopotential signals at a different sensor-skin interface than the neuromuscular-signal-sensing component (e.g., corresponding to a different motor unit of the user).

In some embodiments, the method 500 further includes validating (528) the additional neuromuscular-signal-sensing component based on the received signal. For example, the decryption module 360 of the controller component 350 in FIG. 3A decrypts the signal provided from the encryption module 312. In some embodiments, the additional neuromuscular-signal-sensing signal-sensing component uses a different secret/key and/or different encryption methodology than the neuromuscular-signal-sensing component.

In some embodiments, the method 500 further includes, in accordance with the additional neuromuscular-signal-sensing component being validated, activating (530) an operating mode of the wearable device. In some embodiments, the operating mode of the wearable device is selected based on capabilities of the neuromuscular-signal-sensing components. In some embodiments, the operating mode of the wearable device is selected based on whether some or all of the neuromuscular-signal-sensing components are validated. For example, the notification at the display 203 of the wrist-wearable device 202 in FIG. 3B indicates that the user can install another neuromuscular-signal-sensing component into a particular slot of the wrist-wearable device 202 to cause a different gesture detection model to be activated at the wrist-wearable device 202. In some embodiments, the operating mode of the wearable device comprises a neuromuscular-gesture-detection mode.

In some embodiments, the method 500 further includes, in accordance with the additional neuromuscular-signal-sensing component not being validated, forgoing activating the operating mode of the wearable device. For example, in FIG. 1E, the display of the wrist-wearable device 102 is displaying an indication to the user 101 that a particular gesture detection model will not work based on one of the neuromuscular-signal-sensing components of the wrist-wearable device 102 not being validated. In some embodiments, a gesture detection mode is disabled (or not activated) in accordance with a neuromuscular-signal-sensing component not being validated. In some embodiments, the wearable device operates in a restricted (limited functionality) mode in accordance with a neuromuscular-signal-sensing component not being validated.

(A11) In some embodiments of A10, the method 500 further includes adjusting a machine-learning model based on a number and type of neuromuscular-signal-sensing components coupled to the controller component. For example, FIG. 2B indicates that a backup gesture model has been selected based on the unvalidated neuromuscular-signal-sensing component 204-b not being a particular model (e.g., Model A). In some embodiments, other types of sensors are used to determine the accuracy/precision of the neuromuscular-signal-sensing components. For example, the AR processing module 1845 shown in FIG. 8A may be used to determine a respective accuracy for which the wearable device is able to detect each of a predefined set of gestures associated with an interaction space provided by the wearable device. In some embodiments, the wearable device selects a machine-learning model that corresponds to a given number of neuromuscular-signal-sensing components with respective capabilities.

(A12) In some embodiments of any of A1-A11, the method 500 further includes, at the neuromuscular-signal-sensing component, receiving a secret, and storing the secret for use with subsequent encryption operations. For example, the secret may be based on the manufacturer and/or model (e.g., Model A and/or Manufacturer A; FIG. 1D) of the neuromuscular-signal-sensing component as discussed with respect to the key 314 shown in FIG. 3A. In some embodiments, the secret is embedded in electrode silicon of the neuromuscular-signal-sensing component. In some embodiments, the secret is stored in a secret storage module (e.g., the secret storage module 316) of the neuromuscular-signal-sensing component.

(A13) In some embodiments of any of A1-A12, the encrypted signal is transmitted in accordance with the neuromuscular-signal-sensing component being communicatively coupled to the controller component. For example, coupling the neuromuscular-signal-sensing component and the controller component for the first time causes an encrypted transmission to be sent from the neuromuscular-signal-sensing component for validation at the controller (e.g., FIGS. 1A-1C show a validation process being performed based on the user attaching the neuromuscular-signal-sensing component 104 to the wrist-wearable device 102 in FIG. 1A). In some embodiments, the encrypted signal is transmitted in accordance with power being provided to the neuromuscular-signal-sensing component. In some embodiments, the encrypted signal is transmitted in accordance with the controller component transitioning to a particular mode of operation.

(B1) In accordance with some embodiments, a system that includes one or more wrist-wearable devices and an artificial-reality headset, and the system is configured to perform operations corresponding to any of A1-A13. For example, the system 800 shown in FIG. 8A includes the head-wearable device 811, and the wrist-wearable device 888, and one or both of the head-wearable device 811 and the wrist-wearable device 888 may be configured to perform any of the operations described herein, either individually or in combination. Further, one or more operations described herein may be performed at an intermediary device (e.g., a portable computing unit) that is in electronic communication with both the head-wearable device 811 and the wrist-wearable device 888.

(C1) In accordance with some embodiments, a non-transitory computer-readable storage medium including instructions that, when executed by a computing device, cause the computer device to perform operations corresponding to any of A1-A13.

(D1) In accordance with some embodiments, a method of operating an artificial-reality device includes operations that correspond to any of A1-A13.

(E1) In accordance with some embodiments, a method of operating a wearable device includes operations that correspond to any of A1-A13.

(F1) In another aspect, means for performing each operation of any of A1-A13 are provided.

In some embodiments, other detachable components of the wearable device are configured to provide encrypted signals to the controller component, such that the respective detachable components can be validated for use with the wearable device. For example, sensor-receiving structures (e.g., the sensor-receiving structures 189-*a* and 189-*b* in FIG. 1A), which are configured to receive neuromuscular-signal-sensing components, can be configured to send an encrypted signal to the controller component. In some embodiments, a same biopotential signal is encrypted by a neuromuscular-signal-sensing component and a sensor-receiving structure, but the signal is encrypted using different respective keys corresponding to the neuromuscular-signal sensing component and the sensor-receiving structure, respectively.

The devices described above are further detailed below, including wrist-wearable devices, headset devices, systems, and haptic feedback devices. Specific operations described above may occur as a result of specific hardware; such hardware is described in further detail below. The devices described below are not limiting and features on these devices can be removed or additional features can be added to these devices.

Example Systems

Figure 6A:
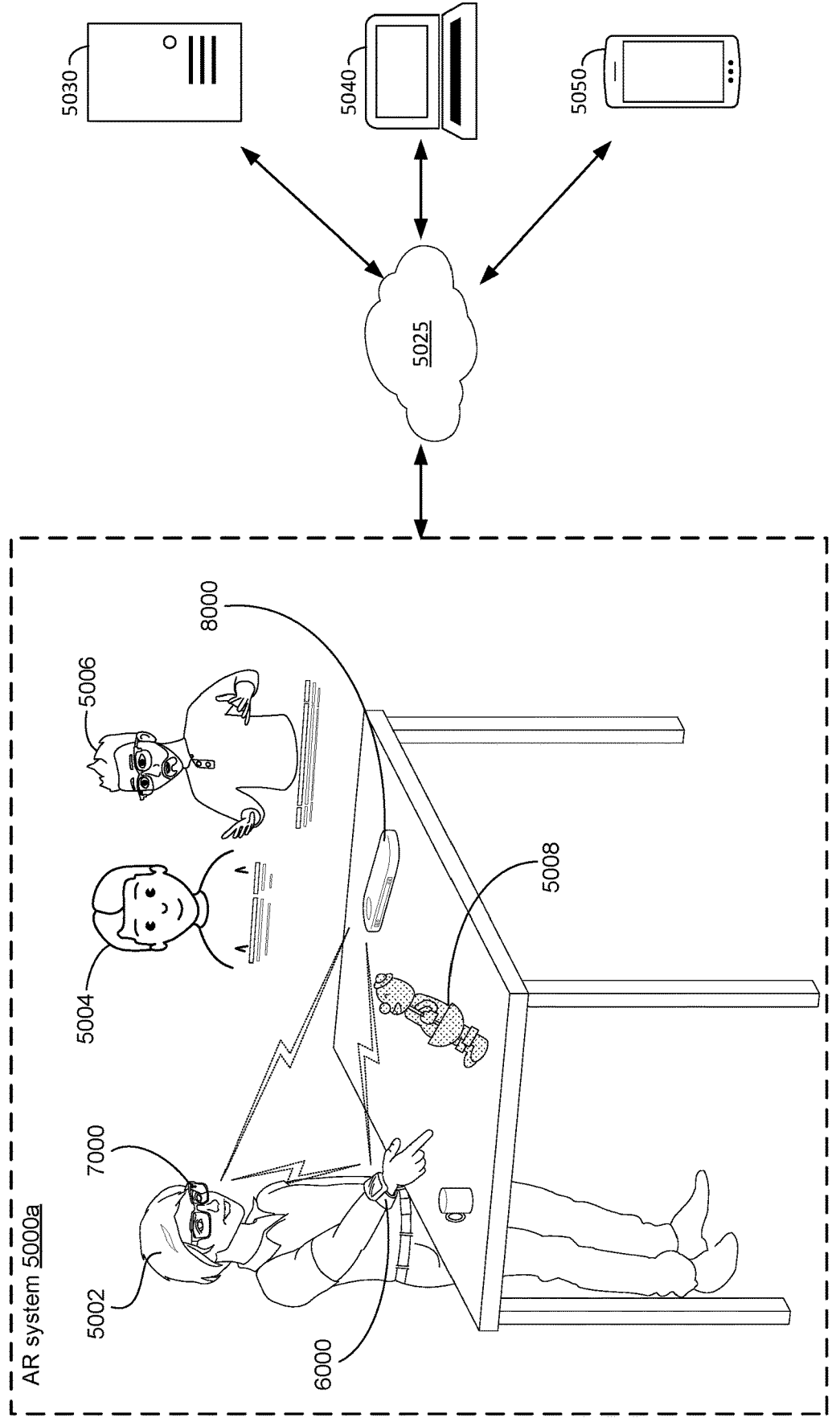
FIGS. 6A-6D illustrate example AR systems in accordance with some embodiments.
Figure 6B:
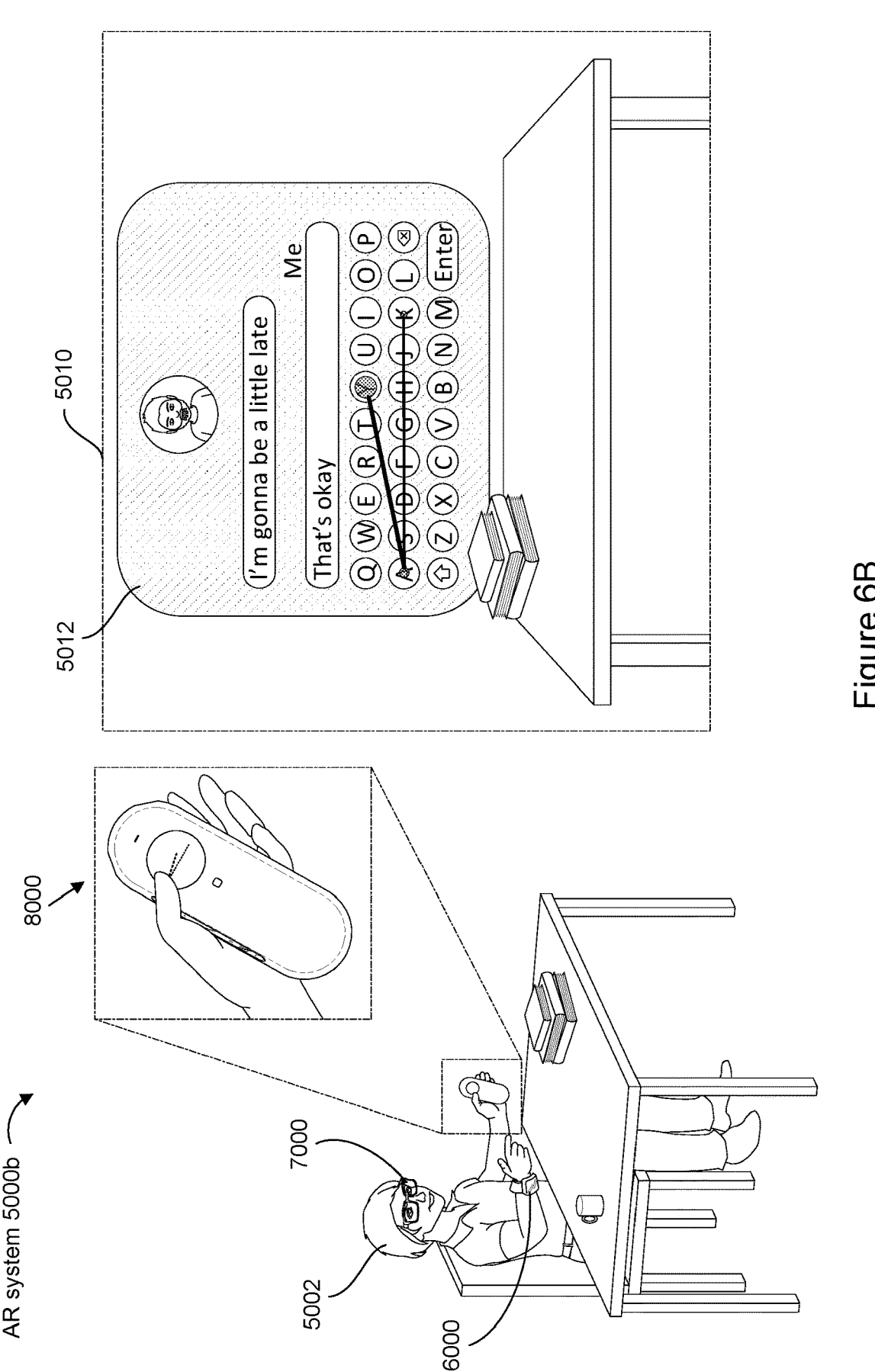
Figures 1, 6C:
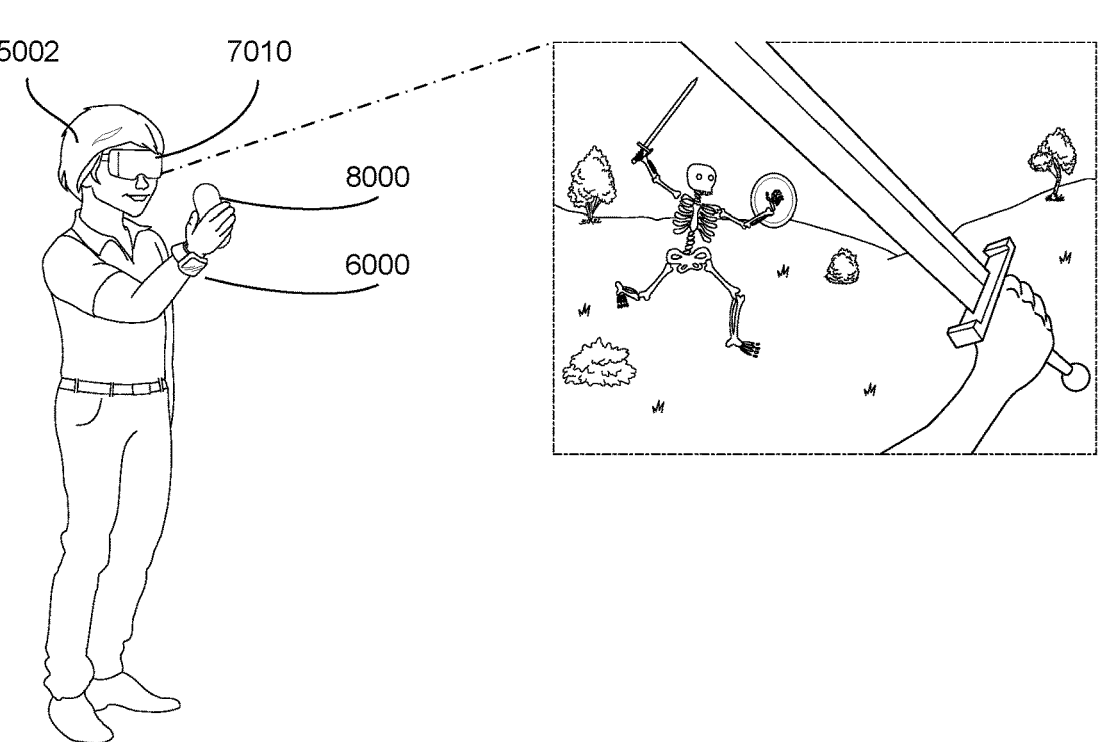
Figures 2, 6C:
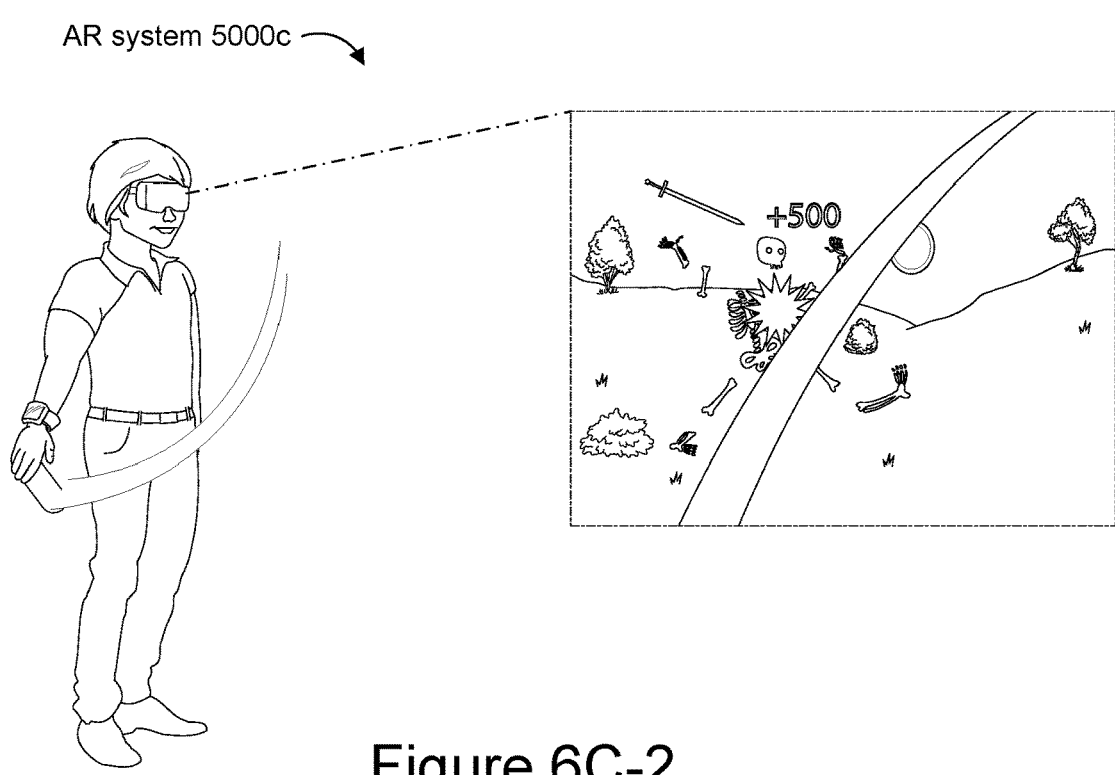
Figures 1, 6D:
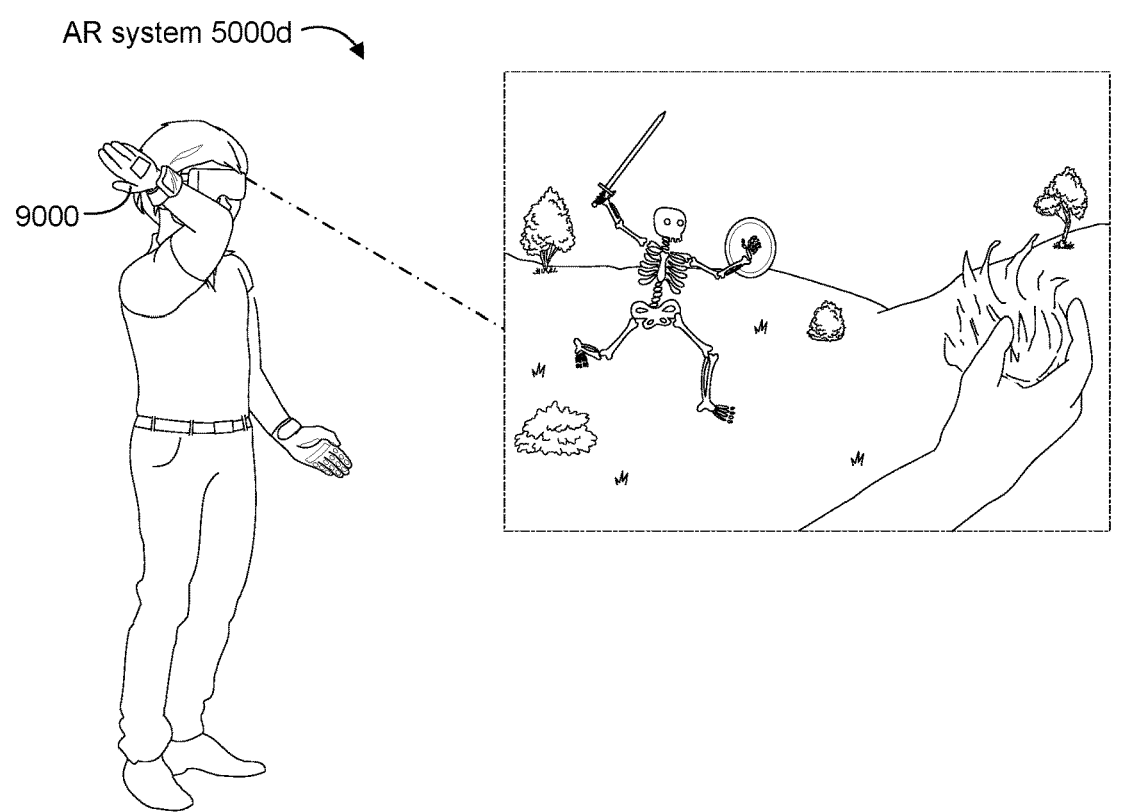
Figures 2, 6D:
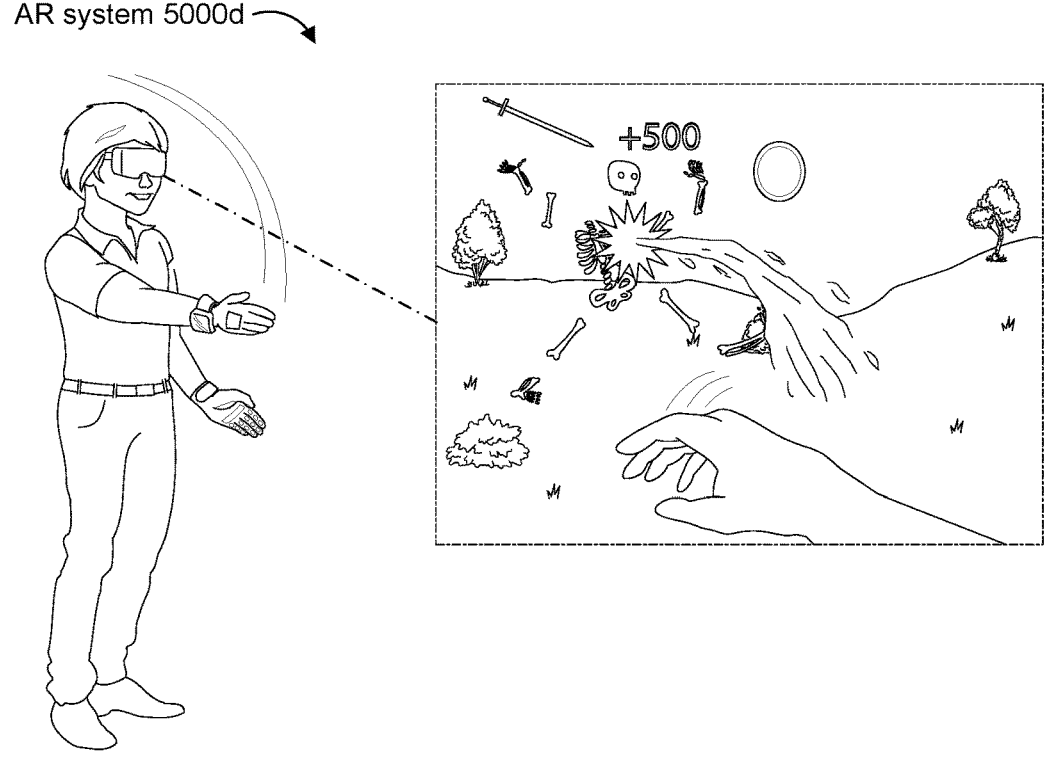

FIGS. 6A-6D illustrate example AR systems in accordance with some embodiments. FIG. 6A shows an AR system 5000*a* and first example user interactions using a wrist-wearable device 6000, a head-wearable device (e.g., AR system 7000), and/or a handheld intermediary processing device (HIPD) 8000. FIG. 6B shows an AR system 5000*b* and second example user interactions using the wrist-wearable device 6000, the AR system 7000, and/or an HIPD 8000. FIGS. 6C-1 and 6C-2 show an AR system 5000*c* and third example user interactions using a wrist-wearable device 6000, a head-wearable device (e.g., VR headset 7010), and/or an HIPD 8000. FIGS. 6D-1 and 6D-2 show a fourth AR system 5000*d* and fourth example user interactions using a wrist-wearable device 6000, VR headset 7010, and/or device 9000 (e.g., wearable haptic gloves). The above-example AR systems (described in detail below) can perform the various functions and/or operations described above with reference to FIGS. 1-5.

The wrist-wearable device 6000 and its components are described below in reference to FIGS. 7A-7B; the head-wearable devices and their components are described below in reference to FIGS. 8A-8D; and the HIPD 8000 and its components are described below in reference to FIGS. 14A-14B. Wearable gloves and their components are described below in reference to FIGS. 10A-10C. As shown in FIG. 6A, the wrist-wearable device 6000, the head-wearable devices, and/or the HIPD 8000 can communicatively couple via a network 5025 (e.g., cellular, near field, Wi-Fi, personal area network, or wireless LAN). Additionally, the wrist-wearable device 6000, the head-wearable devices, and/or the HIPD 8000 can also communicatively couple with one or more servers 5030, computers 5040 (e.g., laptops, computers, etc.), mobile devices 5050 (e.g., smartphones, tablets, etc.), and/or other electronic devices via the network 5025 (e.g., cellular, near field, Wi-Fi, personal area network, wireless LAN, etc.) Similarly, the device 9000 can also communicatively couple with the wrist-wearable device 6000, the head-wearable devices, the HIPD 8000, the one or more servers 5030, the computers 5040, the mobile devices 5050, and/or other electronic devices via the network 5025.

Turning to FIG. 6A, a user 5002 is shown wearing the wrist-wearable device 6000 and the AR system 7000 and having the HIPD 8000 on their desk. The wrist-wearable device 6000, the AR system 7000, and the HIPD 8000 facilitate user interaction with an AR environment. In particular, as shown by the AR system 5000a, the wrist-wearable device 6000, the AR system 7000, and/or the HIPD 8000 cause presentation of one or more avatars 5004, digital representations of contacts 5006, and virtual objects 5008. As discussed below, the user 5002 can interact with the one or more avatars 5004, digital representations of the contacts 5006, and virtual objects 5008 via the wrist-wearable device 6000, the AR system 7000, and/or the HIPD 8000.

The user 5002 can use any of the wrist-wearable device 6000, the AR system 7000, and/or the HIPD 8000 to provide user inputs. For example, the user 5002 can perform one or more hand gestures that are detected by the wrist-wearable device 6000 (e.g., using one or more EMG sensors and/or IMUs, described below in reference to FIGS. 7A-7B) and/or AR system 7000 (e.g., using one or more image sensor or camera, described below in reference to FIGS. 8A-8B) to provide a user input. Alternatively, or additionally, the user 5002 can provide a user input via one or more touch surfaces of the wrist-wearable device 6000, the AR system 7000, and/or the HIPD 8000, and/or voice commands captured by a microphone of the wrist-wearable device 6000, the AR system 7000, and/or the HIPD 8000. In some embodiments, the wrist-wearable device 6000, the AR system 7000, and/or the HIPD 8000 include a digital assistant to help the user in providing a user input (e.g., completing a sequence of operations, suggesting different operations or commands, providing reminders, or confirming a command). In some embodiments, the user 5002 provides a user input via one or more facial gestures and/or facial expressions. For example, cameras of the wrist-wearable device 6000, the AR system 7000, and/or the HIPD 8000 can track the user 5002's eyes for navigating a user interface.

The wrist-wearable device 6000, the AR system 7000, and/or the HIPD 8000 can operate alone or in conjunction to allow the user 5002 to interact with the AR environment. In some embodiments, the HIPD 8000 is configured to operate as a central hub or control center for the wrist-wearable device 6000, the AR system 7000, and/or another communicatively coupled device. For example, the user 5002 can provide an input to interact with the AR environment at any of the wrist-wearable device 6000, the AR system 7000, and/or the HIPD 8000, and the HIPD 8000 can identify one or more back-end and front-end tasks to cause the performance of the requested interaction and distribute instructions to cause the performance of the one or more back-end and front-end tasks at the wrist-wearable device 6000, the AR system 7000, and/or the HIPD 8000. In some embodiments, a back-end task is background processing task that is not perceptible by the user (e.g., rendering content, decompression, or compression), and a front-end task is a user-facing task that is perceptible to the user (e.g., presenting information to the user or providing feedback to the user). As described below in reference to FIGS. 14A-14B, the HIPD 8000 can perform the back-end tasks and provide the wrist-wearable device 6000 and/or the AR system 7000 operational data corresponding to the performed back-end tasks such that the wrist-wearable device 6000 and/or the AR system 7000 can perform the front-end tasks. In this way, the HIPD 8000, which can have more computational resources and greater thermal headroom than the wrist-wearable device 6000 and/or the AR system 7000, performs computationally intensive tasks and reduces the computer resource utilization and/or power usage of the wrist-wearable device 6000 and/or the AR system 7000.

In the example shown by the AR system 5000a, the HIPD 8000 identifies one or more back-end tasks and front-end tasks associated with a user request to initiate an AR video call with one or more other users (represented by the avatar 5004 and the digital representation of the contact 5006) and distributes instructions to cause the performance of the one or more back-end tasks and front-end tasks. In particular, the HIPD 8000 performs back-end tasks for processing and/or rendering image data (and other data) associated with the AR video call and provides operational data associated with the performed back-end tasks to the AR system 7000 such that the AR system 7000 perform front-end tasks for presenting the AR video call (e.g., presenting the avatar 5004 and the digital representation of the contact 5006).

In some embodiments, the HIPD 8000 operates as a focal or anchor point for causing the presentation of information. This allows the user 5002 to be generally aware of where information is presented. For example, as shown in the AR system 5000a, the avatar 5004 and the digital representation of the contact 5006 are presented above the HIPD 8000. In particular, the HIPD 8000 and the AR system 7000 operate in conjunction to determine a location for presenting the avatar 5004 and the digital representation of the contact 5006. In some embodiments, information can be presented a predetermined distance from the HIPD 8000 (e.g., within 5 meters). For example, as shown in the AR system 5000a, virtual object 5008 is presented on the desk some distance from the HIPD 8000. Similar to the above example, the HIPD 8000 and the AR system 7000 can operate in conjunction to determine a location for presenting the virtual object 5008. Alternatively, in some embodiments, presentation of information is not bound by the HIPD 8000. More specifically, the avatar 5004, the digital representation of the contact 5006, and the virtual object 5008 do not have to be presented within a predetermined distance of the HIPD 8000.

User inputs provided at the wrist-wearable device 6000, the AR system 7000, and/or the HIPD 8000 are coordinated such that the user can use any device to initiate, continue, and/or complete an operation. For example, the user 5002 can provide a user input to the AR system 7000 to cause the AR system 7000 to present the virtual object 5008 and, while the virtual object 5008 is presented by the AR system 7000, the user 5002 can provide one or more hand gestures via the wrist-wearable device 6000 to interact and/or manipulate the virtual object 5008.

FIG. 6B shows the user 5002 wearing the wrist-wearable device 6000 and the AR system 7000 and holding the HIPD 8000. In the AR system 5000b, the wrist-wearable device 6000, the AR system 7000, and/or the HIPD 8000 are used to receive and/or provide one or more messages to a contact of the user 5002. In particular, the wrist-wearable device 6000, the AR system 7000, and/or the HIPD 8000 detect and coordinate one or more user inputs to initiate a messaging application and prepare a response to a received message via the messaging application.

In some embodiments, the user 5002 initiates, via a user input, an application on the wrist-wearable device 6000, the AR system 7000, and/or the HIPD 8000 that causes the application to initiate on at least one device. For example, in the AR system 5000b the user 5002 performs a hand gesture associated with a command for initiating a messaging application (represented by messaging user interface 5012); the wrist-wearable device 6000 detects the hand gesture; and, based on a determination that the user 5002 is wearing AR system 7000, causes the AR system 7000 to present a messaging user interface 5012 of the messaging application. The AR system 7000 can present the messaging user interface 5012 to the user 5002 via its display (e.g., as shown by user 5002's field of view 5010). In some embodiments, the application is initiated and ran on the device (e.g., the wrist-wearable device 6000, the AR system 7000, and/or the HIPD 8000) that detects the user input to initiate the application, and the device provides another device operational data to cause the presentation of the messaging application. For example, the wrist-wearable device 6000 can detect the user input to initiate a messaging application; initiate and run the messaging application; and provide operational data to the AR system 7000 and/or the HIPD 8000 to cause presentation of the messaging application. Alternatively, the application can be initiated and ran at a device other than the device that detected the user input. For example, the wrist-wearable device 6000 can detect the hand gesture associated with initiating the messaging application and cause the HIPD 8000 to run the messaging application and coordinate the presentation of the messaging application.

Further, the user 5002 can provide a user input provided at the wrist-wearable device 6000, the AR system 7000, and/or the HIPD 8000 to continue and/or complete an operation initiated are at another device. For example, after initiating the messaging application via the wrist-wearable device 6000 and while the AR system 7000 present the messaging user interface 5012, the user 5002 can provide an input at the HIPD 8000 to prepare a response (e.g., shown by the swipe gesture performed on the HIPD 8000). The user 5002's gestures performed on the HIPD 8000 can be provided and/or displayed on another device. For example, the user 5002's swipe gestured performed on the HIPD 8000 are displayed on a virtual keyboard of the messaging user interface 5012 displayed by the AR system 7000.

In some embodiments, the wrist-wearable device 6000, the AR system 7000, the HIPD 8000, and/or other communicatively couple device presents one or more notifications to the user 5002. The notification can be an indication of a new message, an incoming call, an application update, or a status update. The user 5002 can select the notification via the wrist-wearable device 6000, the AR system 7000, the HIPD 8000, and cause presentation of an application or operation associated with the notification on at least one device. For example, the user 5002 can receive a notification that a message was received at the wrist-wearable device 6000, the AR system 7000, the HIPD 8000, and/or other communicatively couple device and provide a user input at the wrist-wearable device 6000, the AR system 7000, and/or the HIPD 8000 to review the notification, and the device detecting the user input can cause an application associated with the notification to be initiated and/or presented at the wrist-wearable device 6000, the AR system 7000, and/or the HIPD 8000.

While the above example describes coordinated inputs used to interact with a messaging application, the skilled artisan will appreciate upon reading the descriptions that user inputs can be coordinated to interact with any number of applications including, but not limited to, gaming applications, social media applications, camera applications, web-based applications, and financial applications. For example, the AR system 7000 can present to the user 5002 game application data and the HIPD 8000 can use a controller to provide inputs to the game. Similarly, the user 5002 can use the wrist-wearable device 6000 to initiate a camera of the AR system 7000, and the user can use the wrist-wearable device 6000, the AR system 7000, and/or the HIPD 8000 to manipulate the image capture (e.g., zoom in or out, apply filters, etc.) and capture image data.

Having discussed example AR systems, devices for interacting with such AR systems, and other computing systems more generally, will now be discussed in greater detail below. Some definitions of devices and components that can be included in some or all of the example devices discussed below are defined here for ease of reference. A skilled artisan will appreciate that certain types of the components described below may be more suitable for a particular set of devices, and less suitable for a different set of devices. But subsequent reference to the components defined here should be considered to be encompassed by the definitions provided.

In some embodiments discussed below example devices and systems, including electronic devices and systems, will be discussed. Such example devices and systems are not intended to be limiting, and one of skill in the art will understand that alternative devices and systems to the example devices and systems described herein may be used to perform the operations and construct the systems and device that are described herein.

As described herein, an electronic device is a device that uses electrical energy to perform one or more functions. It can be any physical object that contains electronic components such as transistors, resistors, capacitors, diodes, and integrated circuits. Examples of electronic devices include smartphones, laptops, digital cameras, televisions, gaming consoles, and music players, as well as the example electronic devices discussed herein. As described herein, an intermediary electronic device is a device that sits between two other electronic devices, and/or a subset of components of one or more electronic devices and facilitates communication, and/or data processing and/or data transfer between the respective electronic devices and/or electronic components.

As described herein, a processor (e.g., a central processing unit (CPU)), is an electronic component that is responsible for executing instructions and controlling the operation of an electronic device (e.g., a computer). There are various types of processors that may be used interchangeably, or may be specifically required, by embodiments described herein. For example, a processor may be: (i) a general processor designed to perform a wide range of tasks, such as running software applications, managing operating systems, and performing arithmetic and logical operations; (ii) a microcontroller designed for specific tasks such as controlling electronic devices, sensors, and motors; (iii) a graphics processing unit (GPU) designed to accelerate the creation and rendering of images, videos, and animations (e.g., virtual-reality animations, such as three-dimensional modeling); (iv) a field-programmable gate array (FPGA) that can be programmed and reconfigured after manufacturing, and/or can be customized to perform specific tasks, such as signal processing, cryptography, and machine learning; (v) a digital signal processor (DSP) designed to perform mathematical operations on signals such as audio, video, and radio waves. One of skill in the art will understand that one or more processors of one or more electronic devices may be used in various embodiments described herein.

As described herein, memory refers to electronic components in a computer or electronic device that store data and instructions for the processor to access and manipulate. Examples of memory can include: (i) random access memory (RAM) configured to store data and instructions temporarily; (ii) read-only memory (ROM) configured to store data and instructions permanently (e.g., one or more portions of system firmware, and/or boot loaders); (iii) flash memory, which can be configured to store data in electronic devices (e.g., USB drives, memory cards, and/or solid-state drives (SSDs); and (iv) cache memory configured to temporarily store frequently accessed data and instructions. Memory, as described herein, can include structured data (e.g., SQL databases, MongoDB databases, GraphQL data, and/or JSON data). Other examples of memory can include: (i) profile data, including user account data, user settings, and/or other user data stored by the user; (ii) sensor data detected and/or otherwise obtained by one or more sensors; (iii) media content data including stored image data, audio data, documents, and the like; (iv) application data, which can include data collected and/or otherwise obtained and stored during use of an application; and/or any other types of data described herein.

As described herein, controllers are electronic components that manage and coordinate the operation of other components within an electronic device (e.g., controlling inputs, processing data, and/or generating outputs). Examples of controllers can include: (i) microcontrollers, including small, low-power controllers that are commonly used in embedded systems and Internet of Things (IOT) devices; (ii) programmable logic controllers (PLCs) which may be configured to be used in industrial automation systems to control and monitor manufacturing processes; (iii) system-on-a-chip (SoC) controllers that integrate multiple components such as processors, memory, I/O interfaces, and other peripherals into a single chip; and/or DSPs.

As described herein, a power system of an electronic device is configured to convert incoming electrical power into a form that can be used to operate the device. A power system can include various components, including: (i) a power source, which can be an alternating current (AC) adapter or a direct current (DC) adapter power supply; (ii) a charger input, and can be configured to use a wired and/or wireless connection (which may be part of a peripheral interface, such as a USB, micro-USB interface, near-field magnetic coupling, magnetic inductive and magnetic resonance charging, and/or radio frequency (RF) charging); (iii) a power-management integrated circuit, configured to distribute power to various components of the device and to ensure that the device operates within safe limits (e.g., regulating voltage, controlling current flow, and/or managing heat dissipation); and/or (iv) a battery configured to store power to provide usable power to components of one or more electronic devices.

As described herein, peripheral interfaces are electronic components (e.g., of electronic devices) that allow electronic devices to communicate with other devices or peripherals, and can provide a means for input and output of data and signals. Examples of peripheral interfaces can include: (i) universal serial bus (USB) and/or micro-USB interfaces configured for connecting devices to an electronic device; (ii) Bluetooth interfaces configured to allow devices to communicate with each other, including Bluetooth low energy (BLE); (iii) near field communication (NFC) interfaces configured to be short-range wireless interface for operations such as access control; (iv) POGO pins, which may be small, spring-loaded pins configured to provide a charging interface; (v) wireless charging interfaces; (vi) GPS interfaces; (vii) Wi-Fi interfaces for providing a connection between a device and a wireless network; (viii) sensor interfaces.

As described herein, sensors are electronic components (e.g., in and/or otherwise in electronic communication with electronic devices, such as wearable devices) configured to detect physical and environmental changes and generate electrical signals. Examples of sensors can includer: (i) imaging sensors for collecting imaging data (e.g., including one or more cameras disposed on a respective electronic device); (ii) biopotential-signal sensors; (iii) inertial measurement unit (e.g., IMUs) for detecting, for example, angular rate, force, magnetic field, and/or changes in acceleration; (iv) heart rate sensors for measuring a user's heart rate; (v) SpO2 sensors for measuring blood oxygen saturation and/or other biometric data of a user; (vi) capacitive sensors for detecting changes in potential at a portion of a user's body (e.g., a sensor-skin interface); light sensors (e.g., time-of-flight sensors, infrared light sensors, visible light sensors, etc.); . . . . As described herein biopotential-signal-sensing components are devices used to measure electrical activity within the body (e.g., biopotential-signal sensors). Some types of biopotential-signal sensors include: (i) electroencephalography (EEG) sensors configured to measure electrical activity in the brain to diagnose neurological disorders; (ii) electrocardiogramhy (ECG or EKG) sensors configured to measure electrical activity of the heart to diagnose heart problems; (iii) electromyography (EMG) sensors configured to measure the electrical activity of muscles and to diagnose neuromuscular disorders; (iv) electrooculography (EOG) sensors configure to measure the electrical activity of eye muscles to detect eye movement and diagnose eye disorders.

As described herein, an application stored in memory of an electronic device (e.g., software) includes instructions stored in the memory. Examples of such applications include: (i) games; (ii) word processors; messaging applications; media-streaming applications; financial applications; calendars; clocks; communication interface modules for enabling wired and/or wireless connections between different respective electronic devices (e.g., IEEE 802.15.4, Wi-Fi, ZigBec, 6LoWPAN, Thread, Z-Wave, Bluetooth Smart, ISA100.11a, WirelessHART, or MiWi), custom or standard wired protocols (e.g., Ethernet or HomePlug), and/or any other suitable communication protocols);

As described herein, a communication interface is a mechanism that enables different systems or devices to exchange information and data with each other, including hardware, software, or a combination of both hardware and software. For example, a communication interface can refer to a physical connector and/or port on a device that enables communication with other devices (e.g., USB, Ethernet, HDMI, Bluetooth). In some embodiments, a communication interface can refer to a software layer that enables different software programs to communicate with each other (e.g., application programming interfaces (APIs) and/or protocols like HTTP and TCP/IP).

As described herein, a graphics module is a component or software module that is designed to handle graphical operations and/or processes, and can include a hardware module and/or a software module.

As described herein, non-transitory computer-readable storage media are physical devices or storage medium that can be used to store electronic data in a non-transitory form (e.g., such that the data is stored permanently until it is intentionally deleted or modified).

Example Wrist-Wearable Devices

Figure 7A:
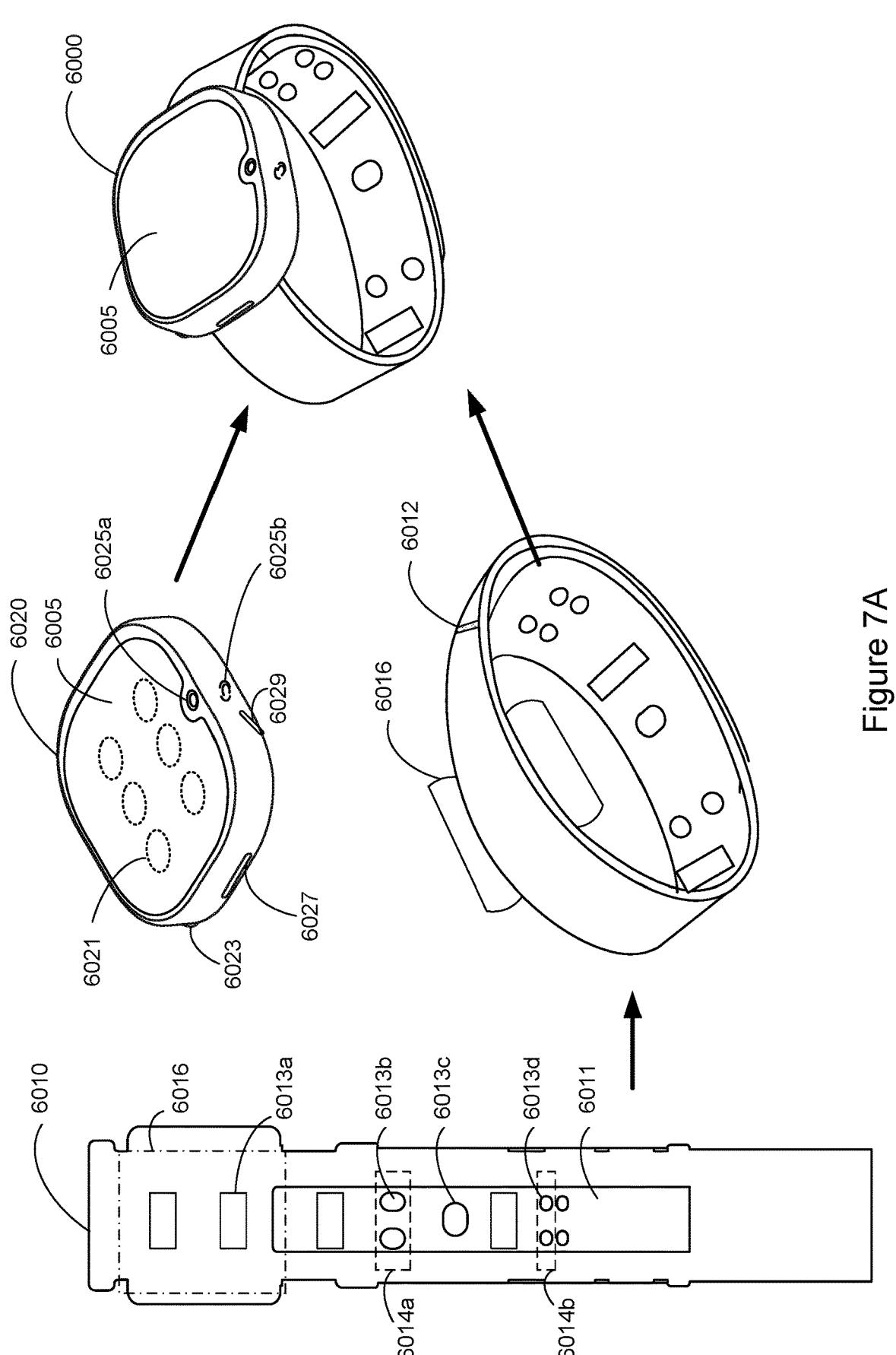
FIGS. 7A-7B illustrate an example wrist-wearable device in accordance with some embodiments.
Figure 7B:
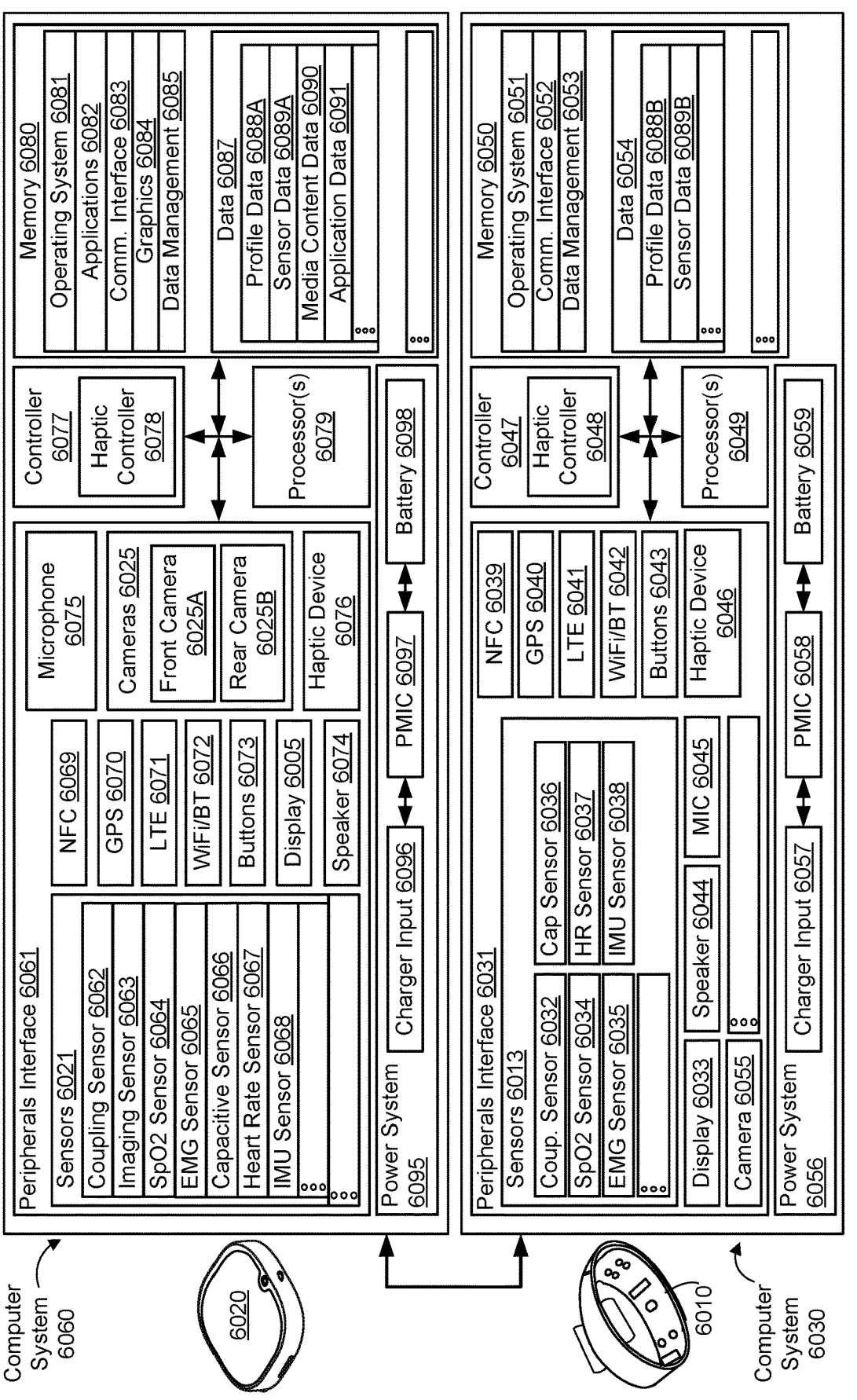

FIGS. 7A and 7B illustrate the wrist-wearable device 6000 in accordance with some embodiments. FIG. 7A illustrates components of the wrist-wearable device 6000, which can be used individually or in combination, including combinations that include other electronic devices and/or electronic components.

FIG. 7A shows a wearable band 6010 and a watch body 6020 (or capsule) being coupled, as discussed below, to form the wrist-wearable device 6000. The wrist-wearable device 6000 can perform various functions and/or operations associated with navigating through user interfaces and selectively opening applications, as well as the functions and/or operations described above with reference to FIGS. 1A-6.

As will be described in more detail below, operations executed by the wrist-wearable device 6000 can include: (i) presenting content to a user (e.g., displaying visual content via a display 6005); (ii) detecting (e.g., sensing) user input (e.g., sensing a touch on peripheral button 6023 and/or at a touch screen of the display 6005, a hand gesture detected by sensors (e.g., biopotential sensors); (iii) sensing biometric data via one or more sensors 6013 (e.g., neuromuscular signals, heart rate, temperature, and/or sleep); messaging (e.g., text, speech, and/or video); image capture via one or more imaging devices or cameras 6025; wireless communications (e.g., cellular, near field, Wi-Fi, and/or personal area network); location determination; financial transactions; providing haptic feedback; alarms; notifications; biometric authentication; health monitoring; sleep monitoring; etc.

The above-example functions can be executed independently in the watch body 6020, independently in the wearable band 6010, and/or via an electronic communication between the watch body 6020 and the wearable band 6010. In some embodiments, functions can be executed on the wrist-wearable device 6000 while an AR environment is being presented (e.g., via one of the AR systems 5000a to 5000d). As the skilled artisan will appreciate upon reading the descriptions provided herein, the novel wearable devices described herein can be used with other types of AR environments.

The wearable band 6010 can be configured to be worn by a user such that an inner surface of the wearable band 6010 is in contact with the user's skin. When worn by a user, sensors 6013 contact the user's skin. The sensors 6013 can sense biometric data such as a user's heart rate, saturated oxygen level, temperature, sweat level, neuromuscular signal sensors, or a combination thereof. The sensors 6013 can also sense data about a user's environment including a user's motion, altitude, location, orientation, gait, acceleration, position, or a combination thereof. In some embodiment, the sensors 6013 are configured to track a position and/or motion of the wearable band 6010. The one or more sensors 6013 can include any of the sensors defined above and/or discussed below with respect to FIG. 7B.

The one or more sensors 6013 can be distributed on an inside and/or an outside surface of the wearable band 6010. In some embodiments, the one or more sensors 6013 are uniformly spaced along the wearable band 6010. Alternatively, in some embodiments, the one or more sensors 6013 are positioned at distinct points along the wearable band 6010. As shown in FIG. 7A, the one or more sensors 6013 can be the same or distinct. For example, in some embodiments, the one or more sensors 6013 can be shaped as a pill (e.g., sensor 6013a), an oval, a circle a square, an oblong (e.g., sensor 6013c) and/or any other shape that maintains contact with the user's skin (e.g., such that neuromuscular signal and/or other biometric data can be accurately measured at the user's skin). In some embodiments, the one or more sensors 6013 are aligned to form pairs of sensors (e.g., for sensing neuromuscular signals based on differential sensing within each respective sensor). For example, sensor 6013b is aligned with an adjacent sensor to form sensor pair 6014a and sensor 6013d aligned with an adjacent sensor to form sensor pair 6014b. In some embodiments, the wearable band 6010 does not have a sensor pair. Alternatively, in some embodiments, the wearable band 6010 has a predetermined number of sensor pairs (e.g., one pair of sensors, three pairs of sensors, four pairs of sensors, six pairs of sensors, or sixteen pairs of sensors).

The wearable band 6010 can include any suitable number of sensors 6013. In some embodiments, the number and arrangement of sensors 6013 depends on the particular application for which the wearable band 6010 is used. For instance, a wearable band 6010 configured as an armband, wristband, or chest-band may include a plurality of sensors 6013 with different number of sensors 6013 and different arrangement for each use case, such as medical use cases as compared to gaming or general day-to-day use cases.

In accordance with some embodiments, the wearable band 6010 further includes an electrical ground electrode and a shielding electrode. The electrical ground and shielding electrodes, like the sensors 6013, can be distributed on the inside surface of the wearable band 6010 such that they contact a portion of the user's skin. For example, the electrical ground and shielding electrodes can be at an inside surface of coupling mechanism 6016 or an inside surface of a wearable structure 6011. The electrical ground and shielding electrodes can be formed and/or use the same components as the sensors 6013. In some embodiments, the wearable band 6010 includes more than one electrical ground electrode and more than one shielding electrode.

The sensors 6013 can be formed as part of the wearable structure 6011 of the wearable band 6010. In some embodiments, the sensors 6013 are flush or substantially flush with the wearable structure 6011 such that they do not extend beyond the surface of the wearable structure 6011. While flush with the wearable structure 6011, the sensors 6013 are still configured to contact the user's skin (e.g., via a skin-contacting surface). Alternatively, in some embodiments, the sensors 6013 extend beyond the wearable structure 6011 a predetermined distance (e.g., 0.1-2 mm) to make contact and depress into the user's skin. In some embodiment, the sensors 6013 are coupled to an actuator (not shown) configured to adjust an extension height (e.g., a distance from the surface of the wearable structure 6011) of the sensors 6013 such that the sensors 6013 make contact and depress into the user's skin. In some embodiments, the actuators adjust the extension height between 0.01 mm-1.2 mm. This allows the user to customize the positioning of the sensors 6013 to improve the overall comfort of the wearable band 6010 when worn while still allowing the sensors 6013 to contact the user's skin. In some embodiments, the sensors 6013 are indistinguishable from the wearable structure 6011 when worn by the user.

The wearable structure 6011 can be formed of an elastic material, elastomers, etc. configured to be stretched and fitted to be worn by the user. In some embodiments, the wearable structure 6011 is a textile or woven fabric. As described above, the sensors 6013 can be formed as part of a wearable structure 6011. For example, the sensors 6013 can be molded into the wearable structure 6011 or be integrated into a woven fabric (e.g., the sensors 6013 can be sewn into the fabric and mimic the pliability of fabric (e.g., the sensors 6013 can be constructed from a series woven strands of fabric)).

The wearable structure 6011 can include flexible electronic connectors that interconnect the sensors 6013, the electronic circuitry, and/or other electronic components (described below in reference to FIG. 7B) that are enclosed in the wearable band 6010. In some embodiments, the flexible electronic connectors are configured to interconnect the sensors 6013, the electronic circuitry, and/or other electronic components of the wearable band 6010 with respective sensors and/or other electronic components of another electronic device (e.g., watch body 6020). The flexible electronic connectors are configured to move with the wearable structure 6011 such that the user adjustment to the wearable structure 6011 (e.g., resizing, pulling, and/or folding) does not stress or strain the electrical coupling of components of the wearable band 6010.

As described above, the wearable band 6010 is configured to be worn by a user. In particular, the wearable band 6010 can be shaped or otherwise manipulated to be worn by a user. For example, the wearable band 6010 can be shaped to have a substantially circular shape such that it can be configured to be worn on the user's lower arm or wrist. Alternatively, the wearable band 6010 can be shaped to be worn on another body part of the user, such as the user's upper arm (e.g., around a bicep), forearm, chest, or legs. The wearable band 6010 can include a retaining mechanism 6012 (e.g., a buckle or a hook and loop fastener) for securing the wearable band 6010 to the user's wrist or other body part. While the wearable band 6010 is worn by the user, the sensors 6013 sense data (referred to as sensor data) from the user's skin. In particular, the sensors 6013 of the wearable band 6010 obtain (e.g., sense and record) neuromuscular signals.

The sensed data (e.g., sensed neuromuscular signals) can be used to detect and/or determine the user's intention to perform certain motor actions. In particular, the sensors 6013 sense and record neuromuscular signals from the user as the user performs muscular activations (e.g., movements and/or gestures). The detected and/or determined motor actions (e.g., phalange (or digits) movements, wrist movements, hand movements, and/or other muscle intentions) can be used to determine control commands or control information (instructions to perform certain commands after the data is sensed) for causing a computing device to perform one or more input commands. For example, the sensed neuromuscular signals can be used to control certain user interfaces displayed on the display 6005 of the wrist-wearable device 6000 and/or can be transmitted to a device responsible for rendering an artificial-reality environment (e.g., a head-mounted display) to perform an action in an associated artificial-reality environment, such as to control the motion of a virtual device displayed to the user. The muscular activations performed by the user can include static gestures, such as placing the user's hand palm down on a table; dynamic gestures, such as grasping a physical or virtual object; and covert gestures that are imperceptible to another person, such as slightly tensing a joint by co-contracting opposing muscles or using sub-muscular activations. The muscular activations performed by the user can include symbolic gestures (e.g., gestures mapped to other gestures, interactions, or commands, for example, based on a gesture vocabulary that specifies the mapping of gestures to commands).

The sensor data sensed by the sensors 6013 can be used to provide a user with an enhanced interaction with a physical object (e.g., devices communicatively coupled with the wearable band 6010) and/or a virtual object in an artificial-reality application generated by an artificial-reality system (e.g., user interface objects presented on the display 6005, or another computing device (e.g., a smartphone)).

In some embodiments, the wearable band 6010 includes one or more haptic devices 6046 (FIG. 7B, e.g., a vibratory haptic actuator) that are configured to provide haptic feedback (e.g., a cutaneous and/or kinesthetic sensation) to the user's skin. The sensors 6013, and/or the haptic devices 6046 can be configured to operate in conjunction with multiple applications including, without limitation, health monitoring, social media, games, and artificial reality (e.g., the applications associated with artificial reality).

The wearable band 6010 can also include coupling mechanism 6016 (e.g., a cradle or a shape of the coupling mechanism can correspond to shape of the watch body 6020 of the wrist-wearable device 6000) for detachably coupling a capsule (e.g., a computing unit) or watch body 6020 (via a coupling surface of the watch body 6020) to the wearable band 6010. In particular, the coupling mechanism 6016 can be configured to receive a coupling surface proximate to the bottom side of the watch body 6020 (e.g., a side opposite to a front side of the watch body 6020 where the display 6005 is located), such that a user can push the watch body 6020 downward into the coupling mechanism 6016 to attach the watch body 6020 to the coupling mechanism 6016. In some embodiments, the coupling mechanism 6016 can be configured to receive a top side of the watch body 6020 (e.g., a side proximate to the front side of the watch body 6020 where the display 6005 is located) that is pushed upward into the cradle, as opposed to being pushed downward into the coupling mechanism 6016. In some embodiments, the coupling mechanism 6016 is an integrated component of the wearable band 6010 such that the wearable band 6010 and the coupling mechanism 6016 are a single unitary structure. In some embodiments, the coupling mechanism 6016 is a type of frame or shell that allows the watch body 6020 coupling surface to be retained within or on the wearable band 6010 coupling mechanism 6016 (e.g., a cradle, a tracker band, a support base, or a clasp).

The coupling mechanism 6016 can allow for the watch body 6020 to be detachably coupled to the wearable band 6010 through a friction fit, magnetic coupling, a rotation-based connector, a shear-pin coupler, a retention spring, one or more magnets, a clip, a pin shaft, a hook and loop fastener, or a combination thereof. A user can perform any type of motion to couple the watch body 6020 to the wearable band 6010 and to decouple the watch body 6020 from the wearable band 6010. For example, a user can twist, slide, turn, push, pull, or rotate the watch body 6020 relative to the wearable band 6010, or a combination thereof, to attach the watch body 6020 to the wearable band 6010 and to detach the watch body 6020 from the wearable band 6010. Alternatively, as discussed below, in some embodiments, the watch body 6020 can be decoupled from the wearable band 6010 by actuation of the release mechanism 6029.

The wearable band 6010 can be coupled with a watch body 6020 to increase the functionality of the wearable band 6010 (e.g., converting the wearable band 6010 into a wrist-wearable device 6000, adding an additional computing unit and/or battery to increase computational resources and/or a battery life of the wearable band 6010, adding additional sensors to improve sensed data, etc.). As described above, the wearable band 6010 (and the coupling mechanism 6016) is configured to operate independently (e.g., execute functions independently) from watch body 6020. For example, the coupling mechanism 6016 can include one or more sensors 6013 that contact a user's skin when the wearable band 6010 is worn by the user and provide sensor data for determining control commands.

A user can detach the watch body 6020 (or capsule) from the wearable band 6010 in order to reduce the encumbrance of the wrist-wearable device 6000 to the user. For embodiments in which the watch body 6020 is removable, the watch body 6020 can be referred to as a removable structure, such that in these embodiments the wrist-wearable device 6000 includes a wearable portion (e.g., the wearable band 6010) and a removable structure (the watch body 6020).

Turning to the watch body 6020, the watch body 6020 can have a substantially rectangular or circular shape. The watch body 6020 is configured to be worn by the user on their wrist or on another body part. More specifically, the watch body 6020 is sized to be easily carried by the user, attached on a portion of the user's clothing, and/or coupled to the wearable band 6010 (forming the wrist-wearable device 6000). As described above, the watch body 6020 can have a shape corresponding to the coupling mechanism 6016 of the wearable band 6010. In some embodiments, the watch body 6020 includes a single release mechanism 6029 or multiple release mechanisms (e.g., two release mechanisms 6029 positioned on opposing sides of the watch body 6020, such as spring-loaded buttons) for decoupling the watch body 6020 and the wearable band 6010. The release mechanism 6029 can include, without limitation, a button, a knob, a plunger, a handle, a lever, a fastener, a clasp, a dial, a latch, or a combination thereof.

A user can actuate the release mechanism 6029 by pushing, turning, lifting, depressing, shifting, or performing other actions on the release mechanism 6029. Actuation of the release mechanism 6029 can release (e.g., decouple) the watch body 6020 from the coupling mechanism 6016 of the wearable band 6010, allowing the user to use the watch body 6020 independently from wearable band 6010, and vice versa. For example, decoupling the watch body 6020 from the wearable band 6010 can allow the user to capture images using rear-facing camera 6025B. Although the is shown positioned at a corner of watch body 6020, the release mechanism 6029 can be positioned anywhere on watch body 6020 that is convenient for the user to actuate. In addition, in some embodiments, the wearable band 6010 can also include a respective release mechanism for decoupling the watch body 6020 from the coupling mechanism 6016. In some embodiments, the release mechanism 6029 is optional and the watch body 6020 can be decoupled from the coupling mechanism 6016 as described above (e.g., via twisting or rotating).

The watch body 6020 can include one or more peripheral buttons 6023 and 6027 for performing various operations at the watch body 6020. For example, the peripheral buttons 6023 and 6027 can be used to turn on or wake (e.g., transition from a sleep state to an active state) the display 6005, unlock the watch body 6020, increase or decrease a volume, increase or decrease a brightness, interact with one or more applications, and/or interact with one or more user interfaces. Additionally, or alternatively, in some embodiments, the display 6005 operates as a touch screen and allows the user to provide one or more inputs for interacting with the watch body 6020.

In some embodiments, the watch body 6020 includes one or more sensors 6021. The sensors 6021 of the watch body 6020 can be the same or distinct from the sensors 6013 of the wearable band 6010. The sensors 6021 of the watch body 6020 can be distributed on an inside and/or an outside surface of the watch body 6020. In some embodiments, the sensors 6021 are configured to contact a user's skin when the watch body 6020 is worn by the user. For example, the sensors 6021 can be placed on the bottom side of the watch body 6020 and the coupling mechanism 6016 can be a cradle with an opening that allows the bottom side of the watch body 6020 to directly contact the user's skin. Alternatively, in some embodiments, the watch body 6020 does not include sensors that are configured to contact the user's skin (e.g., including sensors internal and/or external to the watch body

6020 that configured to sense data of the watch body 6020 and the watch body 6020's surrounding environment). In some embodiment, the sensors 6013 are configured to track a position and/or motion of the watch body 6020.

The watch body 6020 and the wearable band 6010 can share data using a wired communication method (e.g., a Universal Asynchronous Receiver/Transmitter (UART) or a USB transceiver) and/or a wireless communication method (e.g., near field communication or Bluetooth). For example, the watch body 6020 and the wearable band 6010 can share data sensed by the sensors 6013 and 6021, as well as application and device specific information (e.g., active and/or available applications, output devices (e.g., display and/or speakers), input devices (e.g., touch screen, microphone, and/or imaging sensors).

In some embodiments, the watch body 6020 can include, without limitation, a front-facing camera 6025A and/or a rear-facing camera 6025B, sensors 6021 (e.g., a biometric sensor, an IMU, a heart rate sensor, a saturated oxygen sensor, a neuromuscular signal sensor, an altimeter sensor, a temperature sensor, a bioimpedance sensor, a pedometer sensor, an optical sensor (e.g., imaging sensor 6063; FIG. 7B), a touch sensor, a sweat sensor, etc.). In some embodiments, the watch body 6020 can include one or more haptic devices 6076 (FIG. 7B; a vibratory haptic actuator) that is configured to provide haptic feedback (e.g., a cutaneous and/or kinesthetic sensation) to the user. The sensors 6021 and/or the haptic device 6076 can also be configured to operate in conjunction with multiple applications including, without limitation, health monitoring applications, social media applications, game applications, and artificial reality applications (e.g., the applications associated with artificial reality).

Figure 9B:
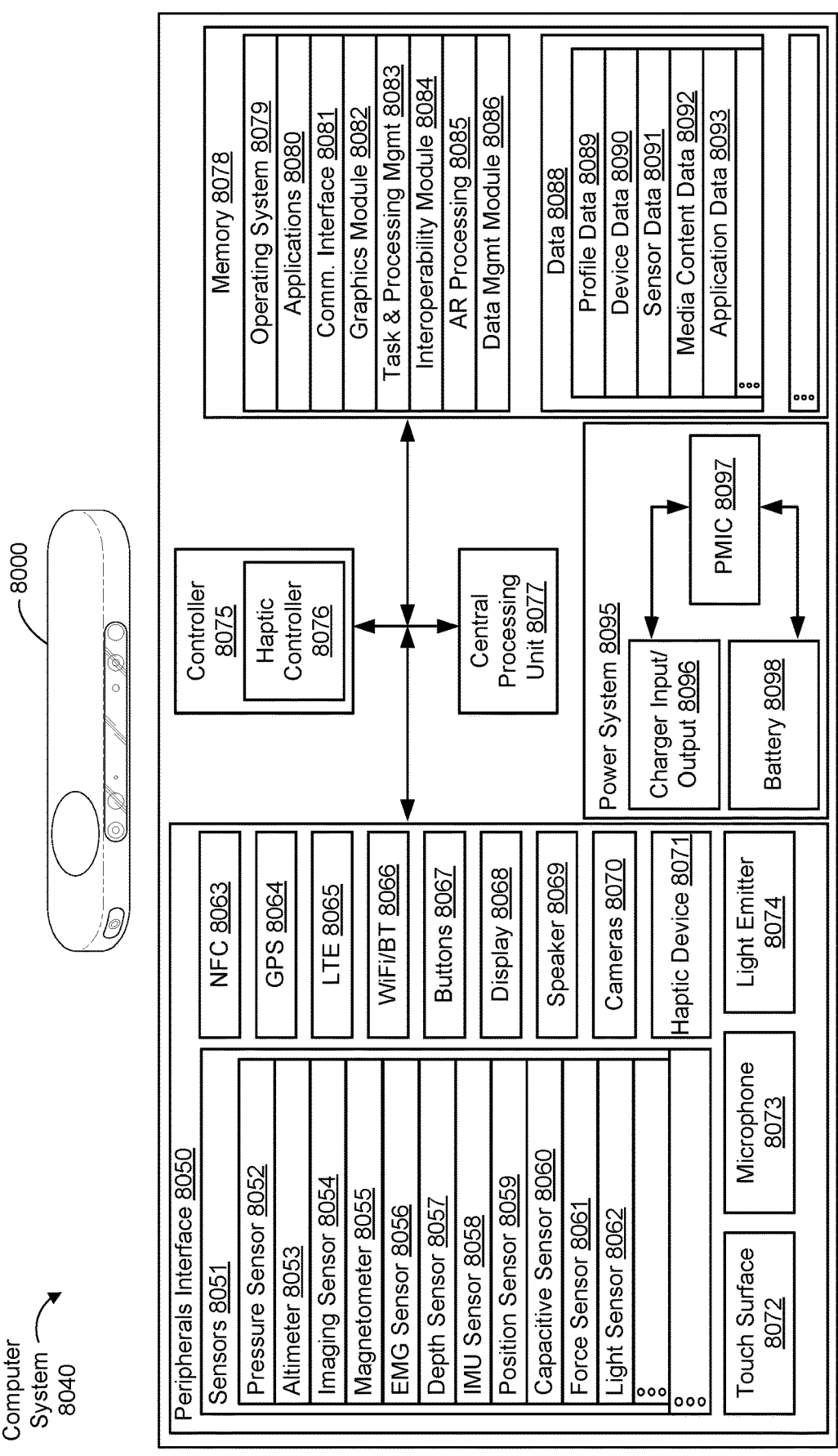

As described above, the watch body 6020 and the wearable band 6010, when coupled, can form the wrist-wearable device 6000. When coupled, the watch body 6020 and wearable band 6010 operate as a single device to execute functions (operations, detections, and/or communications) described herein. In some embodiments, each device is provided with particular instructions for performing the one or more operations of the wrist-wearable device 6000. For example, in accordance with a determination that the watch body 6020 does not include neuromuscular signal sensors, the wearable band 6010 can include alternative instructions for performing associated instructions (e.g., providing sensed neuromuscular signal data to the watch body 6020 via a different electronic device). Operations of the wrist-wearable device 6000 can be performed by the watch body 6020 alone or in conjunction with the wearable band 6010 (e.g., via respective processors and/or hardware components) and vice versa. In some embodiments, operations of the wrist-wearable device 6000, the watch body 6020, and/or the wearable band 6010 can be performed in conjunction with one or more processors and/or hardware components of another communicatively coupled device (e.g., the HIPD 8000; FIGS. 9A-9B).

As described below with reference to the block diagram of FIG. 7B, the wearable band 6010 and/or the watch body 6020 can each include independent resources required to independently execute functions. For example, the wearable band 6010 and/or the watch body 6020 can each include a power source (e.g., a battery), a memory, data storage, a processor (e.g., a central processing unit (CPU)), communications, a light source, and/or input/output devices.

FIG. 7B shows block diagrams of a computing system 6030 corresponding to the wearable band 6010, and a computing system 6060 corresponding to the watch body

6020, according to some embodiments. A computing system of the wrist-wearable device 6000 includes a combination of components of the wearable band computing system 6030 and the watch body computing system 6060, in accordance with some embodiments.

The watch body 6020 and/or the wearable band 6010 can include one or more components shown in watch body computing system 6060. In some embodiments, a single integrated circuit includes all or a substantial portion of the components of the watch body computing system 6060 are included in a single integrated circuit. Alternatively, in some embodiments, components of the watch body computing system 6060 are included in a plurality of integrated circuits that are communicatively coupled. In some embodiments, the watch body computing system 6060 is configured to couple (e.g., via a wired or wireless connection) with the wearable band computing system 6030, which allows the computing systems to share components, distribute tasks, and/or perform other operations described herein (individually or as a single device).

The watch body computing system 6060 can include one or more processors 6079, a controller 6077, a peripherals interface 6061, a power system 6095, and memory (e.g., a memory 6080), each of which are defined above and described in more detail below.

The power system 6095 can include a charger input 6057, a power-management integrated circuit (PMIC) 6097, and a battery 6096, each are which are defined above. In some embodiments, a watch body 6020 and a wearable band 6010 can have respective batteries (e.g., battery 6098 and 6059), and can share power with each other. The watch body 6020 and the wearable band 6010 can receive a charge using a variety of techniques. In some embodiments, the watch body 6020 and the wearable band 6010 can use a wired charging assembly (e.g., power cords) to receive the charge. Alternatively, or in addition, the watch body 6020 and/or the wearable band 6010 can be configured for wireless charging. For example, a portable charging device can be designed to mate with a portion of watch body 6020 and/or wearable band 6010 and wirelessly deliver usable power to a battery of watch body 6020 and/or wearable band 6010. The watch body 6020 and the wearable band 6010 can have independent power systems (e.g., power system 6095 and 6056) to enable each to operate independently. The watch body 6020 and wearable band 6010 can also share power (e.g., one can charge the other) via respective PMICs (e.g., PMICs 6097 and 6058) that can share power over power and ground conductors and/or over wireless charging antennas.

In some embodiments, the peripherals interface 6061 can include one or more sensors 6021, many of which listed below are defined above. The sensors 6021 can include one or more coupling sensor 6062 for detecting when the watch body 6020 is coupled with another electronic device (e.g., a wearable band 6010). The sensors 6021 can include imaging sensors 6063 (one or more of the cameras 6025, and/or separate imaging sensors 6063 (e.g., thermal-imaging sensors)). In some embodiments, the sensors 6021 include one or more SpO2 sensors 6064. In some embodiments, the sensors 6021 include one or more biopotential-signal sensors (e.g., EMG sensors 6065 and 6035, which may be disposed on a user-facing portion of the watch body 6020 and/or the wearable band 6010). In some embodiments, the sensors 6021 include one or more capacitive sensors 6066. In some embodiments, the sensors 6021 include one or more heart rate sensors 6067. In some embodiments, the sensors 6021 include one or more IMU sensors 6068. In some embodiments, one or more IMU sensors 6068 can be configured to detect movement of a user's hand or other location that the watch body 6020 is placed or held).

In some embodiments, the peripherals interface 6061 includes a near-field communication (NFC) component 6069, a global-position system (GPS) component 6070, a long-term evolution (LTE) component 6071, and/or a Wi-Fi and/or Bluetooth communication component 6072. In some embodiments, the peripherals interface 6061 includes one or more buttons 6073 (e.g., the peripheral buttons 6023 and 6027 in FIG. 7A), which, when selected by a user, cause operation to be performed at the watch body 6020. In some embodiments, the peripherals interface 6061 includes one or more indicators, such as a light emitting diode (LED), to provide a user with visual indicators (e.g., message received, low battery, active microphone and/or camera).

The watch body 6020 can include at least one display 6005, for displaying visual representations of information or data to the user, including user-interface elements and/or three-dimensional virtual objects. The display can also include a touch screen for inputting user inputs, such as touch gestures, swipe gestures, and the like. The watch body 6020 can include at least one speaker 6074 and at least one microphone 6075 for providing audio signals to the user and receiving audio input from the user. The user can provide user inputs through the microphone 6075 and can also receive audio output from the speaker 6074 as part of a haptic event provided by the haptic controller 6078. The watch body 6020 can include at least one camera 6025, including a front camera 6025A and a rear camera 6025B. The cameras 6025 can include ultra-wide-angle cameras, wide angle cameras, fish-eye cameras, spherical cameras, telephoto cameras, a depth-sensing cameras, or other types of cameras.

The watch body computing system 6060 can include one or more haptic controllers 6077 and associated componentry (e.g., haptic devices 6076) for providing haptic events at the watch body 6020 (e.g., a vibrating sensation or audio output in response to an event at the watch body 6020). The haptic controllers 6078 can communicate with one or more haptic devices 6076, such as electroacoustic devices, including a speaker of the one or more speakers 6074 and/or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). The haptic controller 6078 can provide haptic events to that are capable of being sensed by a user of the watch body 6020. In some embodiments, the one or more haptic controllers 6078 can receive input signals from an application of the applications 6082.

In some embodiments, the computing system 6030 and/or the computing system 6060 can include memory 6080, which can be controlled by a memory controller of the one or more controllers 6077. In some embodiments, software components stored in the memory 6080 include one or more applications 6082 configured to perform operations at the watch body 6020. In some embodiments, the one or more applications 6082 include games, word processors, messaging applications, calling applications, web browsers, social media applications, media streaming applications, financial applications, calendars, and/or clocks. In some embodiments, software components stored in the memory 6080 include one or more communication interface modules 6083 as defined above. In some embodiments, software components stored in the memory 6080 include one or more graphics modules 6084 for rendering, encoding, and/or decoding audio and/or visual data; and one or more data management modules 6085 for collecting, organizing, and/or providing access to the data 6087 stored in memory 6080. In some embodiments, one or more of applications 6082 and/or one or more modules can work in conjunction with one another to perform various tasks at the watch body 6020.

In some embodiments, software components stored in the memory 6080 can include one or more operating systems 6081 (e.g., a Linux-based operating system or an Android operating system). The memory 6080 can also include data 6087. The data 6087 can include profile data 6088A, sensor data 6089A, media content data 6090, and application data 6091.

It should be appreciated that the watch body computing system 6060 is an example of a computing system within the watch body 6020, and that the watch body 6020 can have more or fewer components than shown in the watch body computing system 6060, combine two or more components, and/or have a different configuration and/or arrangement of the components. The various components shown in watch body computing system 6060 are implemented in hardware, software, firmware, or a combination thereof, including one or more signal processing and/or application-specific integrated circuits.

Turning to the wearable band computing system 6030, one or more components that can be included in the wearable band 6010 are shown. The wearable band computing system 6030 can include more or fewer components than shown in the watch body computing system 6060, combine two or more components, and/or have a different configuration and/or arrangement of some or all of the components. In some embodiments, all, or a substantial portion of the components of the wearable band computing system 6030 are included in a single integrated circuit. Alternatively, in some embodiments, components of the wearable band computing system 6030 are included in a plurality of integrated circuits that are communicatively coupled. As described above, in some embodiments, the wearable band computing system 6030 is configured to couple (e.g., via a wired or wireless connection) with the watch body computing system 6060, which allows the computing systems to share components, distribute tasks, and/or perform other operations described herein (individually or as a single device).

The wearable band computing system 6030, similar to the watch body computing system 6060, can include one or more processors 6049, one or more controllers 6047 (including one or more haptics controller 6048), a peripherals interface 6031 that can includes one or more sensors 6013 and other peripheral devices, power source (e.g., a power system 6056), and memory (e.g., a memory 6050) that includes an operating system (e.g., an operating system 6051), data (e.g., data 6054 including profile data 6088B and/or sensor data 6089B), and one or more modules (e.g., a communications interface module 6052 and/or a data management module 6053).

The one or more sensors 6013 can be analogous to sensors 6021 of the computing system 6060 and in light of the definitions above. For example, sensors 6013 can include one or more coupling sensors 6032, one or more SpO2 sensor 6034, one or more EMG sensors 6035, one or more capacitive sensor 6036, one or more heart rate sensor 6037, and one or more IMU sensor 6038.

The peripherals interface 6031 can also include other components analogous to those included in the peripheral interface 6061 of the computing system 6060, including an NFC component 6039, a GPS component 6040, an LTE component 6041, a Wi-Fi and/or Bluetooth communication component 6042, and/or one or more haptic devices 6076 as described above in reference to peripherals interface 6061. In some embodiments, the peripherals interface 6061 includes one or more buttons 6043, a display 6033, a speaker 6044, a microphone 6045, and a camera 6055. In some embodiments, the peripherals interface 6061 includes one or more indicators, such as an LED.

It should be appreciated that the wearable band computing system 6030 is an example of a computing system within the wearable band 6010, and that the wearable band 6010 can have more or fewer components than shown in the wearable band computing system 6030, combine two or more components, and/or have a different configuration and/or arrangement of the components. The various components shown in wearable band computing system 6030 can be implemented in one or a combination of hardware, software, firmware, including one or more signal processing and/or application-specific integrated circuits.

The wrist-wearable device 6000 with respect to FIG. 7A is an example of the wearable band 6010 and the watch body 6020 coupled, so the wrist-wearable device 6000 will be understood to include the components shown and described for the wearable band computing system 6030 and the watch body computing system 6060. In some embodiments, wrist-wearable device 6000 has a split architecture (e.g., a split mechanical architecture, a split electrical architecture) between the watch body 6020 and the wearable band 6010. In other words, all of the components shown in the wearable band computing system 6030 and the watch body computing system 6060 can be housed or otherwise disposed in a combined watch device 6000, or within individual components of the watch body 6020, wearable band 6010, and/or portions thereof (e.g., a coupling mechanism 6016 of the wearable band 6010).

The techniques described above can be used with any device for sensing neuromuscular signals, including the arm-wearable devices of FIG. 7A-7B, but could also be used with other types of wearable devices for sensing neuromuscular signals (such as body-wearable or head-wearable devices that might have neuromuscular sensors closer to the brain or spinal column).

In some embodiments, a wrist-wearable device 6000 can be used in conjunction with a head-wearable device described below (e.g., AR system 7000 and VR headset 7010) and/or an HIPD 8000; and the wrist-wearable device 6000 can also be configured to be used to allow a user to control aspect of the artificial reality (e.g., by using EMG-based gestures to control user interface objects in the artificial reality and/or by allowing a user to interact with the touchscreen on the wrist-wearable device to also control aspects of the artificial reality). In some embodiments, a wrist-wearable device 6000 can also be used in conjunction with a wearable garment, such as the wearable gloves described below in reference to FIGS. 10A-10C. Having thus described example wrist-wearable device, attention will now be turned to example head-wearable devices, such AR system 7000 and VR headset 7010.

Example Head-Wearable Devices

Figure 8A:
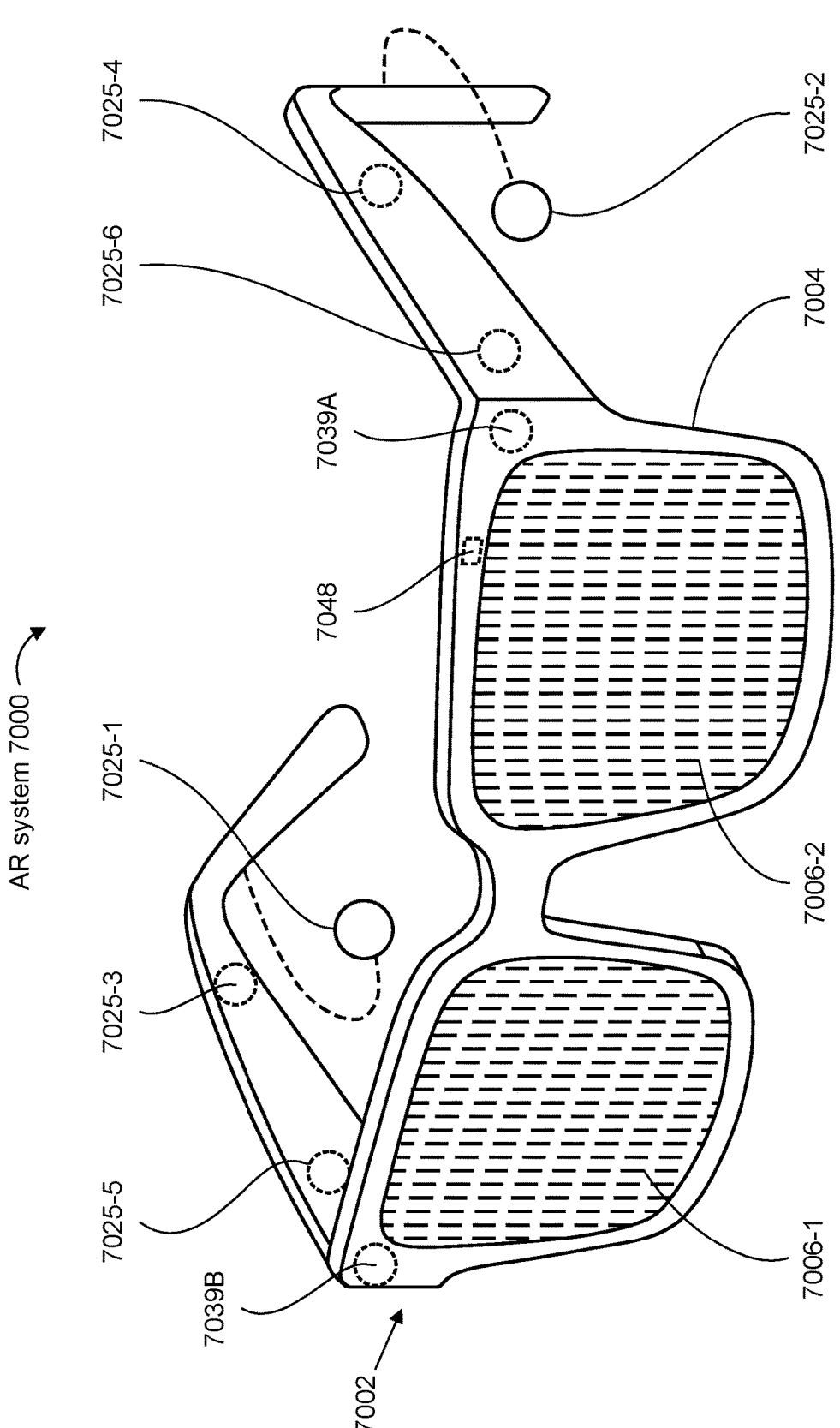
FIGS. 8A-8C illustrate example artificial-reality systems in accordance with some embodiments.
Figures 1, 8B:
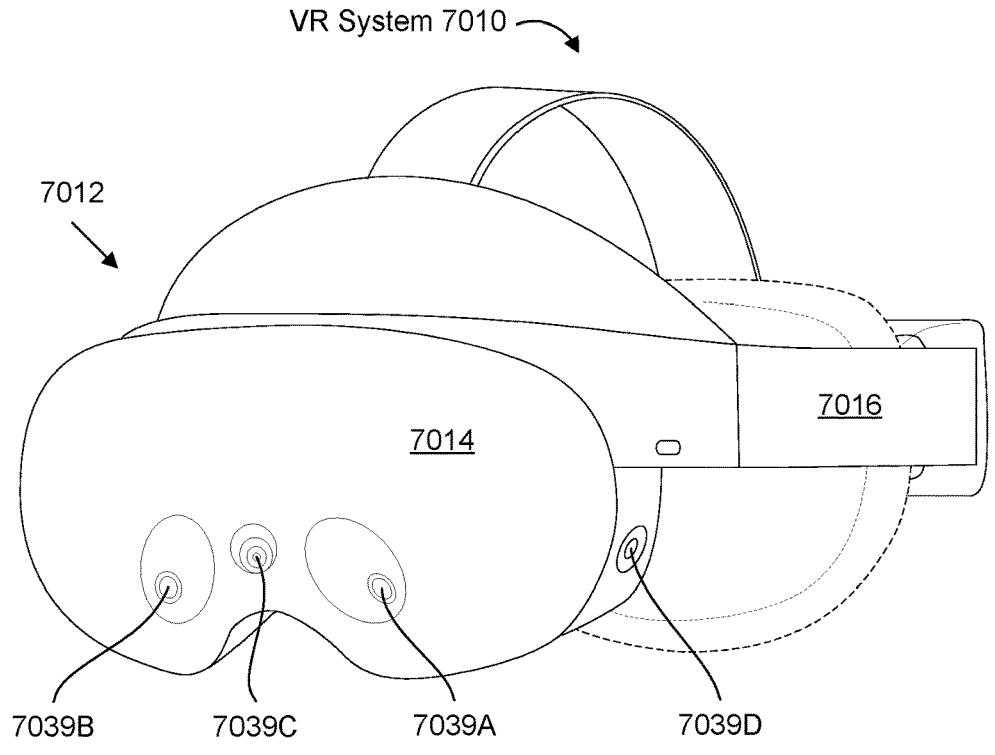
Figures 2, 8B:
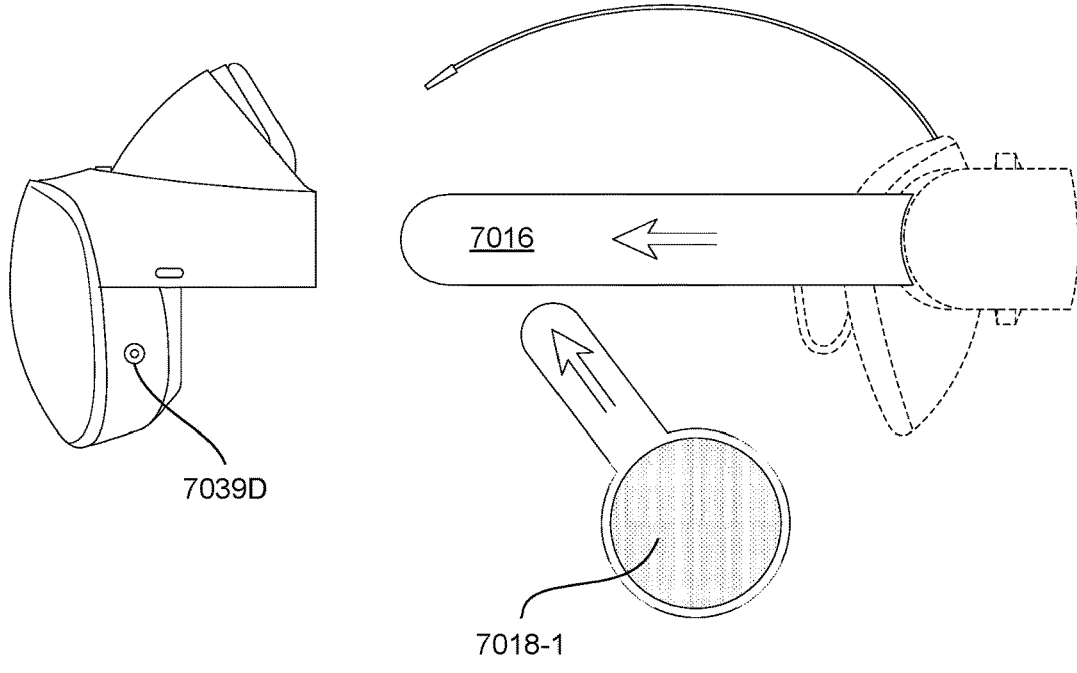
Figure 8C:
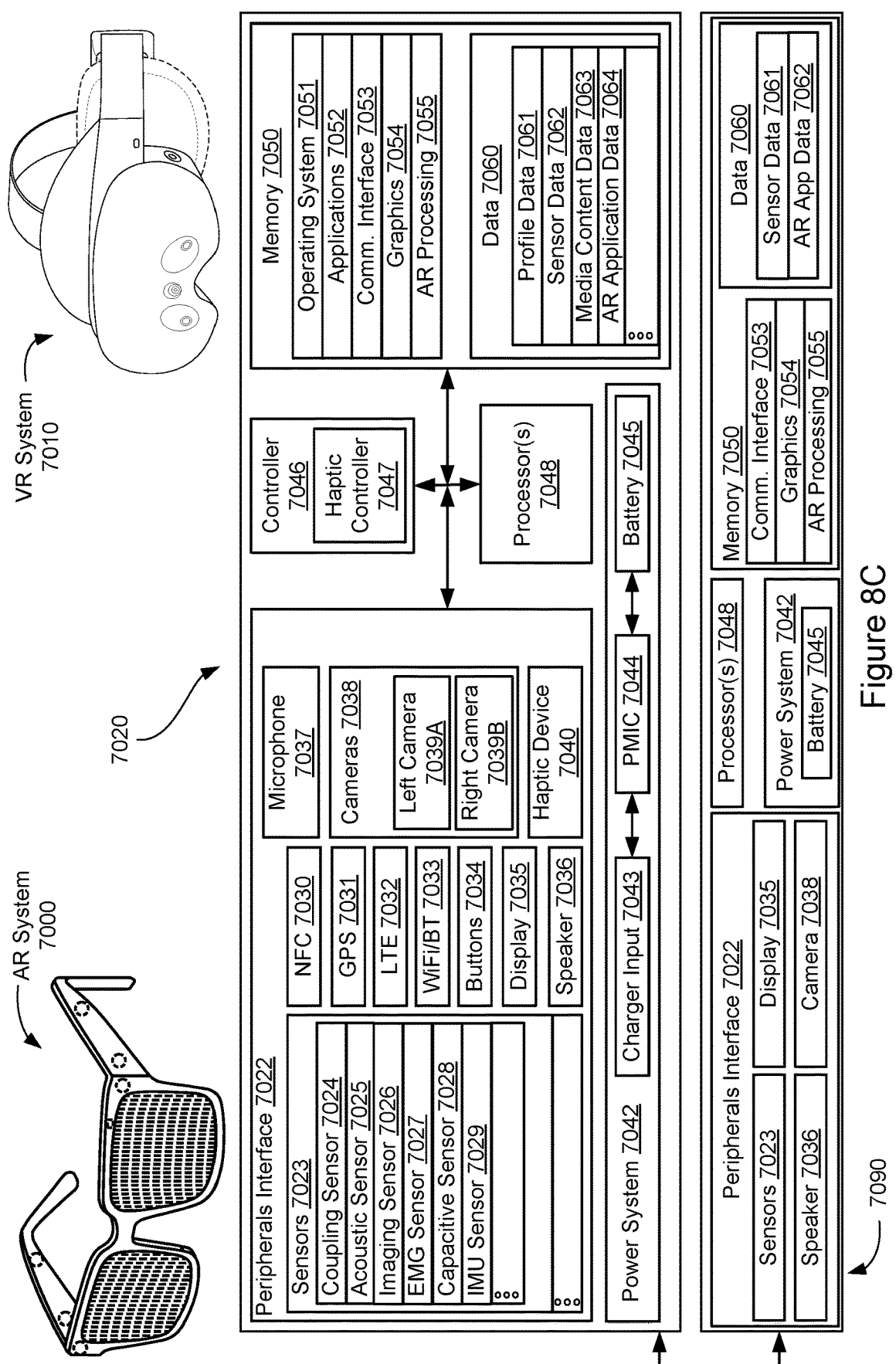

FIGS. 8A to 8C show example artificial-reality systems, including the AR system 7000. In some embodiments, the AR system 7000 is an eyewear device as shown in FIG. 8A. In some embodiments, the VR system 7010 includes a head-mounted display (HMD) 7012, as shown in FIGS. 8B-1 and 8B-2. In some embodiments, the AR system 7000 and the VR system 7010 include one or more analogous components (e.g., components for presenting interactive artificial-reality environments, such as processors, memory, and/or presentation devices, including one or more displays and/or one or more waveguides), some of which are described in more detail with respect to FIG. 8C. As described herein, a head-wearable device can include components of the eyewear device 7002, and/or the head-mounted display 7012. Some embodiments of head-wearable devices do not include any displays, including any of the displays described with respect to the AR system 7000 and/or the VR system 7010. While the example artificial-reality systems are respectively described herein as the AR system 7000 and the VR system 7010, either or both of the example AR systems described herein can be configured to present fully-immersive VR scenes presented in substantially all of a user's field of view, additionally or alternatively to, subtler augmented-reality scenes that are presented within a portion, less than all, of the user's field of view.

FIG. 8A show an example visual depiction of the AR system 7000 (which may also be described herein as augmented-reality glasses, and/or smart glasses). The AR system 7000 can include additional electronic components that are not shown in FIGS. 8A, such as a wearable accessory device and/or an intermediary processing device, in electronic communication or otherwise configured to be used in conjunction with the eyewear device. In some embodiments, the wearable accessory device and/or the intermediary processing device may be configured to couple with the eyewear device via a coupling mechanism in electronic communication with a coupling sensor 7024, where the coupling sensor 7024 can detect when an electronic device becomes physically or electronically coupled with the eyewear device. In some embodiments, the eyewear device is configured to couple to a housing 7090, which may include one or more additional coupling mechanisms configured to couple with additional accessory devices. The components shown in FIG. 8A can be implemented in hardware, software, firmware, or a combination thereof, including one or more signal-processing components and/or application-specific integrated circuits (ASICs).

The eyewear device includes mechanical glasses components, including a frame 7004 configured to hold one or more lenses (e.g., one or both lenses 7006-1 and 7006-2). One of ordinary skill in the art will appreciate that the eyewear device can include additional mechanical components, such as hinges configured to allow portions of the frame 7004 of the eyewear device 7002 to be folded and unfolded, a bridge configured to span the gap between the lenses 7006-1 and 7006-2 and rest on the user's nose, nose pads configured to rest on the bridge of the nose and provide support for the eyewear device, carpieces configured to rest on the user's ears and provide additional support for the eyewear device, temple arms configured to extend from the hinges to the carpieces of the eyewear device, and the like. One of ordinary skill in the art will further appreciate that some examples of the AR system 7000 can include none of the mechanical components described herein. For example, smart contact lenses configured to present artificial reality to users may not include any components of the eyewear device.

The eyewear device includes electronic components, many of which will be described in more detail below with respect to FIG. 8C. Some example electronic components are illustrated in FIG. 8A, including acoustic sensors 7025-1, 7025-2, 7025-3, 7025-4, 7025-5, and 7025-1, which can be distributed along a substantial portion of the frame 7004 of the eyewear device. The eyewear device also includes a left camera 7039A and a right camera 7039B, which are located on different sides of the frame 7004. And the eyewear device includes a processor 7048 (e.g., an integral microprocessor, such as an ASIC) that is embedded into a portion of the frame 7004.

FIGS. 8B-1 and 8B-2 show a VR system 7010 that includes a head-mounted display (HMD) 7012 (e.g., also referred to herein as an artificial-reality headset, a head-wearable device, or a VR headset), in accordance with some embodiments. As noted, some artificial-reality systems may (e.g., the AR system 7000), instead of blending an artificial reality with actual reality, substantially replace one or more of a user's sensory perceptions of the real world with a virtual experience (e.g., the AR systems 5000c and 5000d).

The HMD 7012 includes a front body 7014 and a frame 7016 (e.g., a strap or band) shaped to fit around a user's head. In some embodiments, the front body 7014 and/or the frame 7016 includes one or more electronic elements for facilitating presentation of and/or interactions with an AR and/or VR system (e.g., displays, IMUs, tracking emitter or detectors). In some embodiments, the HMD 7012 includes output audio transducers (e.g., an audio transducer 7018-1), as shown in FIG. 8B-2. In some embodiments, one or more components, such as the output audio transducer(s) 7018-1 and the frame 7016, can be configured to attach and detach (e.g., are detachably attachable) to the HMD 7012 (e.g., a portion or all of the frame 7016, and/or the audio transducer 7018-1), as shown in FIG. 8B-2. In some embodiments, coupling a detachable component to the HMD 7012 causes the detachable component to come into electronic communication with the HMD 7012.

FIG. 8B-1 to 8B-2 also show that the VR system 7010 one or more cameras, such as the left camera 7039A and the right camera 7039B, which can be analogous to the left and right cameras on the frame 7004 of the eyewear device 7002. In some embodiments, the VR system 7010 includes one or more additional cameras (e.g., cameras 7039C and 7039D), which can be configured to augment image data obtained by the cameras 7039A and 7039B by providing more information. For example, the camera 7039C can be used to supply color information that is not discerned by cameras 7039A and 7039B. In some embodiments, one or more of the cameras 7039A to 7039D can include an optional IR cut filter configured to remove IR light from being received at the respective camera sensors.

FIG. 8C illustrates a computing system 7020 and an optional housing 7090, each of which show components that can be included in the AR system 7000 and/or the VR system 7010. In some embodiments, more or less components can be included in the optional housing 7090 depending on practical restraints of the respective AR system being described.

In some embodiments, the computing system 7020 and/or the optional housing 7090 can include one or more peripheral interfaces 7022, one or more power systems 7042, one or more controllers 7046 (including one or more haptic controllers 7047), one or more processors 7048 (as defined above, including any of the examples provided), and memory 7050, which can all be in electronic communication with each other. For example, the one or more processors 7048 can be configured to execute instructions stored in the memory 7050, which can cause a controller of the one or more controllers 7046 to cause operations to be performed at one or more peripheral devices of the peripherals interface 7022. In some embodiments, each operation described can occur based on electrical power provided by the power system 7042.

In some embodiments, the peripherals interface 7022 can include one or more devices configured to be part of the computing system 7020, many of which have been defined above and/or described with respect to wrist-wearable devices shown in FIGS. 7A and 7B. For example, the peripherals interface can include one or more sensors 7023. Some example sensors include: one or more coupling sensors 7024, one or more acoustic sensors 7025, one or more imaging sensors 7026, one or more EMG sensors 7027, one or more capacitive sensors 7028, and/or one or more IMU sensors 7029; and/or any other types of sensors defined above or described with respect to any other embodiments discussed herein.

In some embodiments, the peripherals interface can include one or more additional peripheral devices, including one or more NFC devices 7030, one or more GPS devices 7031, one or more LTE devices 7032, one or more Wi-Fi and/or Bluetooth devices 7033, one or more buttons 7034 (e.g., including buttons that are slidable or otherwise adjustable), one or more displays 7035, one or more speakers 7036, one or more microphones 7037, one or more cameras 7038 (e.g., including the left camera 7039A and/or a right camera 7039B), and/or one or more haptic devices 7040; and/or any other types of peripheral devices defined above or described with respect to any other embodiments discussed herein.

AR systems can include a variety of types of visual feedback mechanisms (e.g., presentation devices). For example, display devices in the AR system 7000 and/or the VR system 7010 can include one or more liquid-crystal displays (LCDs), light emitting diode (LED) displays, organic LED (OLED) displays, and/or any other suitable types of display screens. Artificial-reality systems can include a single display screen (e.g., configured to be seen by both eyes), and/or can provide separate display screens for each eye, which can allow for additional flexibility for varifocal adjustments and/or for correcting a refractive error associated with the user's vision. Some embodiments of AR systems also include optical subsystems having one or more lenses (e.g., conventional concave or convex lenses, Fresnel lenses, or adjustable liquid lenses) through which a user can view a display screen.

For example, respective displays can be coupled to each of the lenses 7006-1 and 7006-2 of the AR system 7000. The displays coupled to each of the lenses 7006-1 and 7006-2 can act together or independently to present an image or series of images to a user. In some embodiments, the AR system 7000 includes a single display (e.g., a near-eye display) or more than two displays. In some embodiments, a first set of one or more displays can be used to present an augmented-reality environment, and a second set of one or more display devices can be used to present a virtual-reality environment. In some embodiments, one or more waveguides are used in conjunction with presenting artificial-reality content to the user of the AR system 7000 (e.g., as a means of delivering light from one or more displays to the user's eyes). In some embodiments, one or more waveguides are fully or partially integrated into the eyewear device 7002. Additionally, or alternatively to display screens, some artificial-reality systems include one or more projection systems. For example, display devices in the AR system 7000 and/or the virtual-reality system 7010 can include micro-LED projectors that project light (e.g., using a waveguide) into display devices, such as clear combiner lenses that allow ambient light to pass through. The display devices can refract the projected light toward a user's pupil and can enable a user to simultaneously view both artificial-reality content and the real world. Artificial-reality systems can also be configured with any other suitable type or form of image projection system. In some embodiments, one or more waveguides are provided additionally or alternatively to the one or more display(s).

The computing system 7020 and/or the optional housing 7090 of the AR system 7000 or the VR system 7010 can include some or all of the components of a power system 7042. The power system 7042 can include one or more charger inputs 7043, one or more PMICs 7044, and/or one or more batteries 7045.

The memory 7050 includes instructions and data, some or all of which may be stored as non-transitory computer-readable storage media within the memory 7050. For example, the memory 7050 can include one or more operating systems 7051; one or more applications 7052; one or more communication interface applications 7053; one or more graphics applications 7054; one or more AR processing applications 7055; and/or any other types of data defined above or described with respect to any other embodiments discussed herein.

The memory 7050 also includes data 7060 which can be used in conjunction with one or more of the applications discussed above. The data 7060 can include: profile data 7061; sensor data 7062; media content data 7063; AR application data 7064; and/or any other types of data defined above or described with respect to any other embodiments discussed herein.

In some embodiments, the controller 7046 of the eyewear device 7002 processes information generated by the sensors 7023 on the eyewear device 7002 and/or another electronic device within the AR system 7000. For example, the controller 7046 can process information from the acoustic sensors 7025-1 and 7025-2. For each detected sound, the controller 7046 can perform a direction of arrival (DOA) estimation to estimate a direction from which the detected sound arrived at the eyewear device 7002 of the AR system 7000. As one or more of the acoustic sensors 7025 detects sounds, the controller 7046 can populate an audio data set with the information (e.g., represented in FIG. 8C as sensor data 7062).

In some embodiments, a physical electronic connector can convey information between the eyewear device and another electronic device, and/or between one or more processors of the AR system 7000 or the VR system 7010 and the controller 7046. The information can be in the form of optical data, electrical data, wireless data, or any other transmittable data form. Moving the processing of information generated by the eyewear device to an intermediary processing device can reduce weight and heat in the eyewear device, making it more comfortable and safer for a user. In some embodiments, an optional wearable accessory device (e.g., an electronic neckband) is coupled to the eyewear device via one or more connectors. The connectors can be wired or wireless connectors and can include electrical and/or non-electrical (e.g., structural) components. In some embodiments, the eyewear device and the wearable accessory device can operate independently without any wired or wireless connection between them.

In some situations, pairing external devices, such as an intermediary processing device (e.g., the HIPD 8000) with the eyewear device 7002 (e.g., as part of the AR system 7000) enables the eyewear device 7002 to achieve a similar form factor of a pair of glasses while still providing sufficient battery and computation power for expanded capabilities. Some, or all, of the battery power, computational resources, and/or additional features of the AR system 7000 can be provided by a paired device or shared between a paired device and the eyewear device 7002, thus reducing the weight, heat profile, and form factor of the eyewear device 7002 overall while allowing the eyewear device 7002 to retain its desired functionality. For example, the wearable accessory device can allow components that would otherwise be included on an eyewear device 7002 to be included in the wearable accessory device and/or intermediary processing device, thereby shifting a weight load from the user's head and neck to one or more other portions of the user's body. In some embodiments, the intermediary processing device has a larger surface area over which to diffuse and disperse heat to the ambient environment. Thus, the intermediary processing device can allow for greater battery and computation capacity than might otherwise have been possible on the eyewear device 7002, standing alone. Because weight carried in the wearable accessory device can be less invasive to a user than weight carried in the eyewear device 7002, a user may tolerate wearing a lighter eyewear device and carrying or wearing the paired device for greater lengths of time than the user would tolerate wearing a heavier eyewear device standing alone, thereby enabling an artificial-reality environment to be incorporated more fully into a user's day-to-day activities.

AR systems can include various types of computer vision components and subsystems. For example, the AR system 7000 and/or the VR system 7010 can include one or more optical sensors such as two-dimensional (2D) or three-dimensional (3D) cameras, time-of-flight depth sensors, single-beam or sweeping laser rangefinders, 3D LiDAR sensors, and/or any other suitable type or form of optical sensor. An AR system can process data from one or more of these sensors to identify a location of a user and/or aspects of the use's real-world physical surroundings, including the locations of real-world objects within the real-world physical surroundings. In some embodiments, the methods described herein are used to map the real world, to provide a user with context about real-world surroundings, and/or to generate digital twins (e.g., interactable virtual objects), among a variety of other functions. For example, FIGS. 8B-1 and 8B-2 show the VR system 7010 having cameras 7039A to 7039D, which can be used to provide depth information for creating a voxel field and a two-dimensional mesh to provide object information to the user to avoid collisions.

In some embodiments, the AR system 7000 and/or the VR system 7010 can include haptic (tactile) feedback systems, which may be incorporated into headwear, gloves, body suits, handheld controllers, environmental devices (e.g., chairs or floormats), and/or any other type of device or system, such as the wearable devices discussed herein. The haptic feedback systems may provide various types of cutaneous feedback, including vibration, force, traction, shear, texture, and/or temperature. The haptic feedback systems may also provide various types of kinesthetic feedback, such as motion and compliance. The haptic feedback may be implemented using motors, piezoelectric actuators, fluidic systems, and/or a variety of other types of feedback mechanisms. The haptic feedback systems may be implemented independently of other artificial-reality devices, within other artificial-reality devices, and/or in conjunction with other artificial-reality devices (e.g., the haptic feedback system described with respect to FIGS. 10A to 10C).

In some embodiments of an AR system, such as the AR system 7000 and/or the VR system 7010, ambient light (e.g., a live feed of the surrounding environment that a user would normally see) can be passed through a display element of a respective head-wearable device presenting aspects of the AR system. In some embodiments, ambient light can be passed through a portion less than all, of an AR environment presented within a user's field of view (e.g., a portion of the AR environment co-located with a physical object in the user's real-world environment that is within a designated boundary (e.g., a guardian boundary) configured to be used by the user while they are interacting with the AR environment. For example, a visual user interface element (e.g., a notification user interface element) can be presented at the head-wearable device, and an amount of ambient light (e.g., 15-50% of the ambient light) can be passed through the user interface element, such that the user can distinguish at least a portion of the physical environment over which the user interface element is being displayed.

Example Handheld Intermediary Processing Devices

FIGS. 9A and 9B illustrate an example handheld intermediary processing device (HIPD) 8000, in accordance with some embodiments. The HIPD 8000 is an instance of the intermediary device described herein, such that the HIPD 8000 should be understood to have the features described with respect to any intermediary device defined above or otherwise described herein, and vice versa. FIG. 9A shows a top view 8005 and a side view 8025 of the HIPD 8000. The HIPD 8000 is configured to communicatively couple with one or more wearable devices (or other electronic devices) associated with a user. For example, the HIPD 8000 is configured to communicatively couple with a user's wrist-wearable device 6000 (or components thereof, such as the watch body 6020 and the wearable band 6010), AR system 7000, and/or VR headset 7010. The HIPD 8000 can be configured to be held by a user (e.g., as a handheld controller), carried on the user's person (e.g., in their pocket, in their bag, etc.), placed in proximity of the user (e.g., placed on their desk while seated at their desk, on a charging dock, etc.), and/or placed at or within a predetermined distance from a wearable device or other electronic device (e.g., where, in some embodiments, the predetermined distance is the maximum distance (e.g., 10 meters) at which the HIPD 8000 can successfully be communicatively coupled with an electronic device, such as a wearable device).

The HIPD 8000 can perform various functions independently and/or in conjunction with one or more wearable devices (e.g., wrist-wearable device 6000, AR system 7000, and/or VR headset 7010). The HIPD 8000 is configured to increase and/or improve the functionality of communicatively coupled devices, such as the wearable devices. The HIPD 8000 is configured to perform one or more functions or operations associated with interacting with user interfaces and applications of communicatively coupled devices, interacting with an AR environment, interacting with VR environment, and/or operating as a human-machine interface controller. Additionally, as will be described in more detail below, functionality and/or operations of the HIPD 8000 can include, without limitation, task offloading and/or handoffs; thermals offloading and/or handoffs; 6 degrees of freedom (6DoF) raycasting and/or gaming (e.g., using imaging devices or cameras 8014, which can be used for simultaneous localization and mapping (SLAM) and/or with other image processing techniques); portable charging; messaging; image capturing via one or more imaging devices or cameras 8022; sensing user input (e.g., sensing a touch on a touch input surface 8002); wireless communications and/or interlining (e.g., cellular, near field, Wi-Fi, personal area network, etc.); location determination; financial transactions; providing haptic feedback; alarms; notifications; biometric authentication; health monitoring; sleep monitoring; etc. The above-example functions can be executed independently in the HIPD 8000 and/or in communication between the HIPD 8000 and another wearable device described herein. In some embodiments, functions can be executed on the HIPD 8000 in conjunction with an AR environment. As the skilled artisan will appreciate upon reading the descriptions provided herein, the novel the HIPD 8000 described herein can be used with any type of suitable AR environment.

While the HIPD 8000 is communicatively coupled with a wearable device and/or other electronic device, the HIPD 8000 is configured to perform one or more operations initiated at the wearable device and/or the other electronic device. In particular, one or more operations of the wearable device and/or the other electronic device can be offloaded to the HIPD 8000 to be performed. The HIPD 8000 performs the one or more operations of the wearable device and/or the other electronic device and provides to data corresponded to the completed operations to the wearable device and/or the other electronic device. For example, a user can initiate a video stream using AR system 7000 and back-end tasks associated with performing the video stream (e.g., video rendering) can be offloaded to the HIPD 8000, which the HIPD 8000 performs and provides corresponding data to the AR system 7000 to perform remaining front-end tasks associated with the video stream (e.g., presenting the rendered video data via a display of the AR system 7000). In this way, the HIPD 8000, which has more computational resources and greater thermal headroom than a wearable device, can perform computationally intensive tasks for the wearable device improving performance of an operation performed by the wearable device.

The HIPD 8000 includes a multi-touch input surface 8002 on a first side (e.g., a front surface) that is configured to detect one or more user inputs. In particular, the multi-touch input surface 8002 can detect single tap inputs, multi-tap inputs, swipe gestures and/or inputs, force-based and/or pressure-based touch inputs, held taps, and the like. The multi-touch input surface 8002 is configured to detect capacitive touch inputs and/or force (and/or pressure) touch inputs. The multi-touch input surface 8002 includes a touch-input surface 8004 defined by a surface depression, and a touch-input surface 8006 defined by a substantially planar portion. The touch-input surface 8004 can be disposed adjacent to the touch-input surface 8006. In some embodiments, the touch-input surface 8004 and the touch-input surface 8006 can be different dimensions, shapes, and/or cover different portions of the multi-touch input surface 8002. For example, the touch-input surface 8004 can be substantially circular and the touch-input surface 8006 is substantially rectangular. In some embodiments, the surface depression of the multi-touch input surface 8002 is configured to guide user handling of the HIPD 8000. In particular, the surface depression is configured such that the user holds the HIPD 8000 upright when held in a single hand (e.g., such that the using imaging devices or cameras 8014A and 8014B are pointed toward a ceiling or the sky). Additionally, the surface depression is configured such that the user's thumb rests within the touch-input surface 8004.

In some embodiments, the different touch-input surfaces include a plurality of touch-input zones. For example, the touch-input surface 8006 includes at least a touch-input zone 8008 within a touch-input zone 8006 and a touch-input zone 8010 within the touch-input zone 8008. In some embodiments, one or more of the touch-input zones are optional and/or user defined (e.g., a user can specific a touch-input zone based on their preferences). In some embodiments, each touch-input surface and/or touch-input zone is associated with a predetermined set of commands. For example, a user input detected within the touch-input zone 8008 causes the HIPD 8000 to perform a first command and a user input detected within the touch-input zone 8006 causes the HIPD 8000 to perform a second command, distinct from the first. In some embodiments, different touch-input surfaces and/or touch-input zones are configured to detect one or more types of user inputs. The different touch-input surfaces and/or touch-input zones can be configured to detect the same or distinct types of user inputs. For example, the touch-input zone 8008 can be configured to detect force touch inputs (e.g., a magnitude at which the user presses down) and capacitive touch inputs, and the touch-input zone 8006 can be configured to detect capacitive touch inputs.

The HIPD 8000 includes one or more sensors 8051 for sensing data used in the performance of one or more operations and/or functions. For example, the HIPD 8000 can include an IMU sensor that is used in conjunction with cameras 8014 for 3-dimensional object manipulation (e.g., enlarging, moving, or destroying an object) in an AR or VR environment. Non-limiting examples of the sensors 8051 included in the HIPD 8000 include a light sensor, a magnetometer, a depth sensor, a pressure sensor, and a force sensor. Additional examples of the sensors 8051 are provided below in reference to FIG. 9B.

The HIPD 8000 can include one or more light indicators 8012 to provide one or more notifications to the user. In some embodiments, the light indicators are LEDs or other types of illumination devices. The light indicators 8012 can operate as a privacy light to notify the user and/or others near the user that an imaging device and/or microphone are active. In some embodiments, a light indicator is positioned adjacent to one or more touch-input surfaces. For example, a light indicator can be positioned around the touch-input surface 8004. The light indicators can be illuminated in different colors and/or patterns to provide the user with one or more notifications and/or information about the device. For example, a light indicator positioned around the touch-input surface 8004 can flash when the user receives a notification (e.g., a message), change red when the HIPD 8000 is out of power, operate as a progress bar (e.g., a light ring that is closed when a task is completed (e.g., 0% to 100%)), operates as a volume indicator, etc.).

In some embodiments, the HIPD 8000 includes one or more additional sensors on another surface. For example, as shown FIG. 9A, HIPD 8000 includes a set of one or more sensors (e.g., sensor set 8020) on an edge of the HIPD 8000. The sensor set 8020, when positioned on an edge of the of the HIPD 8000, can be pe positioned at a predetermined tilt angle (e.g., 26 degrees), which allows the sensor set 8020 to be angled toward the user when placed on a desk or other flat surface. Alternatively, in some embodiments, the sensor set 8020 is positioned on a surface opposite the multi-touch input surface 8002 (e.g., a back surface). The one or more sensors of the sensor set 8020 are discussed in detail below.

The side view 8025 of the of the HIPD 8000 shows the sensor set 8020 and camera 8014B. The sensor set 8020 includes one or more cameras 8022A and 8022B, a depth projector 8024, an ambient light sensor 8028, and a depth receiver 8030. In some embodiments, the sensor set 8020 includes a light indicator 8026. The light indicator 8026 can operate as a privacy indicator to let the user and/or those around them know that a camera and/or microphone is active. The sensor set 8020 is configured to capture a user's facial expression such that the user can puppet a custom avatar (e.g., showing emotions, such as smiles and/or laughter on the avatar or a digital representation of the user). The sensor set 8020 can be configured as a side stereo RGB system, a rear indirect Time-of-Flight (iToF) system, or a rear stereo RGB system. As the skilled artisan will appreciate upon reading the descriptions provided herein, the HIPD 8000 described herein can use different sensor set 8020 configurations and/or sensor set 8020 placements.

In some embodiments, the HIPD 8000 includes one or more haptic devices 8071 (e.g., a vibratory haptic actuator) that are configured to provide haptic feedback (e.g., kinesthetic sensation). The sensors 8051, and/or the haptic devices 8071 can be configured to operate in conjunction with multiple applications and/or communicatively coupled devices including, without limitation, wearable devices, health monitoring applications, social media applications, game applications, and artificial reality applications (e.g., the applications associated with artificial reality).

The HIPD 8000 is configured to operate without a display. However, in optional embodiments, the HIPD 8000 can include a display 8068 (FIG. 9B). The HIPD 8000 can also income one or more optional peripheral buttons 8067 (FIG. 9B). For example, the peripheral buttons 8067 can be used to turn on or turn off the HIPD 8000. Further, the HIPD 8000 housing can be formed of polymers and/or elastomer elastomers. The HIPD 8000 can be configured to have a non-slip surface to allow the HIPD 8000 to be placed on a surface without requiring a user to watch over the HIPD 8000. In other words, the HIPD 8000 is designed such that it would not easily slide off surfaces. In some embodiments, the HIPD 8000 include one or magnets to couple the HIPD 8000 to another surface. This allows the user to mount the HIPD 8000 to different surfaces and provide the user with greater flexibility in use of the HIPD 8000.

As described above, the HIPD 8000 can distribute and/or provide instructions for performing the one or more tasks at the HIPD 8000 and/or a communicatively coupled device. For example, the HIPD 8000 can identify one or more back-end tasks to be performed by the HIPD 8000 and one or more front-end tasks to be performed by a communicatively coupled device. While the HIPD 8000 is configured to offload and/or handoff tasks of a communicatively coupled device, the HIPD 8000 can perform both back-end and front-end tasks (e.g., via one or more processors, such as CPU 8077; FIG. 9B). The HIPD 8000 can, without limitation, can be used to perform augmenting calling (e.g., receiving and/or sending 3D or 2.5D live volumetric calls, live digital human representation calls, and/or avatar calls), discreet messaging, 6DoF portrait/landscape gaming, AR/VR object manipulation, AR/VR content display (e.g., presenting content via a virtual display), and/or other AR/VR interactions. The HIPD 8000 can perform the above operations alone or in conjunction with a wearable device (or other communicatively coupled electronic device).

FIG. 9B shows block diagrams of a computing system 8040 of the HIPD 8000, in accordance with some embodiments. The HIPD 8000, described in detail above, can include one or more components shown in HIPD computing system 8040. The HIPD 8000 will be understood to include the components shown and described below for the HIPD computing system 8040. In some embodiments, all, or a substantial portion of the components of the HIPD computing system 8040 are included in a single integrated circuit. Alternatively, in some embodiments, components of the HIPD computing system 8040 are included in a plurality of integrated circuits that are communicatively coupled.

The HIPD computing system 8040 can include a processor (e.g., a CPU 8077, a GPU, and/or a CPU with integrated graphics), a controller 8075, a peripherals interface 8050 that includes one or more sensors 8051 and other peripheral devices, a power source (e.g., a power system 8095), and memory (e.g., a memory 8078) that includes an operating system (e.g., an operating system 8079), data (e.g., data 8088), one or more applications (e.g., applications 8080), and one or more modules (e.g., a communications interface module 8081, a graphics module 8082, a task and processing management module 8083, an interoperability module 8084, an AR processing module 8085, and/or a data management module 8086). The HIPD computing system 8040 further includes a power system 8095 that includes a charger input and output 8096, a PMIC 8097, and a battery 8098, all of which are defined above.

In some embodiments, the peripherals interface 8050 can include one or more sensors 8051. The sensors 8051 can include analogous sensors to those described above in reference to FIG. 7B. For example, the sensors 8051 can include imaging sensors 8054, (optional) EMG sensors 8056, IMU sensors 8058, and capacitive sensors 8060. In some embodiments, the sensors 8051 can include one or more pressure sensor 8052 for sensing pressure data, an altimeter 8053 for sensing an altitude of the HIPD 8000, a magnetometer 8055 for sensing a magnetic field, a depth sensor 8057 (or a time-of flight sensor) for determining a difference between the camera and the subject of an image, a position sensor 8059 (e.g., a flexible position sensor) for sensing a relative displacement or position change of a portion of the HIPD 8000, a force sensor 8061 for sensing a force applied to a portion of the HIPD 8000, and a light sensor 8062 (e.g., an ambient light sensor) for detecting an amount of lighting. The sensors 8051 can include one or more sensors not shown in FIG. 17B.

Analogous to the peripherals described above in reference to FIGS. 7B, the peripherals interface 8050 can also include an NFC component 8063, a GPS component 8064, an LTE component 8065, a Wi-Fi and/or Bluetooth communication component 8066, a speaker 8069, a haptic device 8071, and a microphone 8073. As described above in reference to FIG. 17A, the HIPD 8000 can optionally include a display 8068 and/or one or more buttons 8067. The peripherals interface 8050 can further include one or more cameras 8070, touch surfaces 8072, and/or one or more light emitters 8074. The multi-touch input surface 8002 described above in reference to FIG. 17A is an example of touch surface 8072. The light emitters 8074 can be one or more LEDs, lasers, etcetera, and can be used to project or present information to a user. For example, the light emitters 8074 can include light indicators 8012 and 8026 described above in reference to FIG. 17A. The cameras 8070 (e.g., cameras 8014 and 8022 described above in FIG. 17A) can include one or more wide angle cameras, fish-eye cameras, spherical cameras, compound eye cameras (e.g., stereo and multi cameras), depth cameras, RGB cameras, ToF cameras, RGB-D cameras (depth and ToF cameras), and/or other available cameras. Cameras 8070 can be used for SLAM; 6 DoF ray casting, gaming, object manipulation, and/or other rendering; facial recognition and facial expression recognition, etc.

Similar to the watch body computing system 6060 and the watch band computing system 6030 described above in reference to FIG. 7B, the HIPD computing system 8040 can include one or more haptic controllers 8076 and associated componentry (e.g., haptic devices 8071) for providing haptic events at the HIPD 8000.

Memory 8078 can include high-speed random-access memory and/or non-volatile memory, such as one or more magnetic disk storage devices, flash memory devices, or other non-volatile solid-state memory devices. Access to the memory 8078 by other components of the HIPD 8000, such as the one or more processors and the peripherals interface 8050, can be controlled by a memory controller of the controllers 8075.

In some embodiments, software components stored in the memory 8078 include one or more operating systems 8079, one or more applications 8080, one or more communication interface modules 8081, one or more graphics modules 8082, one or more data management modules 8086, which are analogous to the software components described above in reference to FIG. 7B.

In some embodiments, software components stored in the memory 8078 include a task and processing management module 8083 for identifying one or more front-end and back-end tasks associated with an operation performed by the user, performing one or more front-end and/or back-end tasks, and/or providing instructions to one or more communicatively coupled devices that cause performance of the one or more front-end and/or back-end tasks. In some embodiments, the task and processing management module 8083 uses data 8088 (e.g., device data 8090) to distribute the one or more front-end and/or back-end tasks based on communicatively coupled devices' computing resources, available power, thermal headroom, ongoing operations, and/or other factors. For example, the task and processing management module 8083 can cause the performance of one or more back-end tasks (of an operation performed at communicatively coupled AR system 7000) at the HIPD 8000 in accordance with a determination that the operation is utilizing a predetermined amount (e.g., at least 70%) of computing resources available at the AR system 7000.

In some embodiments, software components stored in the memory 8078 include an interoperability module 8084 for exchanging and utilizing information received and/or provided to distinct communicatively coupled devices. The interoperability module 8084 allows for different systems, devices, and/or applications to connect and communicate in a coordinated way without user input. In some embodiments, software components stored in the memory 8078 include an AR module 8085 that is configured to process signals based at least on sensor data for use in an AR and/or VR environment. For example, the AR module 8085 can be used for 3D object manipulation, gesture recognition, facial and facial expression, and/or recognition.

The memory 8078 can also include data 8088, including structured data. In some embodiments, the data 8088 includes profile data 8089, device data 8090 (including device data of one or more devices communicatively coupled with the HIPD 8000, such as device type, hardware, software, and/or configurations), sensor data 8091, media content data 8092, and application data 8093.

It should be appreciated that the HIPD computing system 8040 is an example of a computing system within the HIPD 8000, and that the HIPD 8000 can have more or fewer components than shown in the HIPD computing system 8040, combine two or more components, and/or have a different configuration and/or arrangement of the components. The various components shown in HIPD computing system 8040 are implemented in hardware, software, firmware, or a combination thereof, including one or more signal processing and/or application-specific integrated circuits.

The techniques described above in FIG. 17A-17B can be used with any device used as a human-machine interface controller. In some embodiments, an HIPD 8000 can be used in conjunction with one or more wearable device such as a head-wearable device (e.g., AR system 7000 and VR system 7010) and/or a wrist-wearable device 6000 (or components thereof). In some embodiments, an HIPD 8000 is used in conjunction with a wearable garment, such as the wearable gloves of FIGS. 10A-10C. Having thus described example HIPD 8000, attention will now be turned to example feedback devices, such as device 9000.

Example Feedback Devices

FIGS. 10A and 10B show example haptic feedback systems (e.g., hand-wearable devices) for providing feedback to a user regarding the user's interactions with a computing system (e.g., an artificial-reality environment presented by the AR system 7000 or the VR system 7010). In some embodiments, a computing system (e.g., the AR system 5000d) may also provide feedback to one or more users based on an action that was performed within the computing system and/or an interaction provided by the AR system (e.g., which may be based on instructions that are executed in conjunction with performing operations of an application of the computing system). Such feedback may include visual and/or audio feedback and may also include haptic feedback provided by a haptic assembly, such as one or more haptic assemblies 9062 of the device 9000 (e.g., haptic assemblies 9062-1, 9062-2, and 9062-3). For example, the haptic feedback may prevent (or, at a minimum, hinder/resist movement of) one or more fingers of a user from bending past a certain point to simulate the sensation of touching a solid coffee mug. In actuating such haptic effects, the device 9000 can change (either directly or indirectly) a pressurized state of one or more of the haptic assemblies 9062.

Each of the haptic assemblies 9062 includes a mechanism that, at a minimum, provides resistance when the respective haptic assembly 9062 is transitioned from a first pressurized state (e.g., atmospheric pressure or deflated) to a second pressurized state (e.g., inflated to a threshold pressure). Structures of haptic assemblies 9062 can be integrated into various devices configured to be in contact or proximity to a user's skin, including, but not limited to devices such as glove worn devices, body worn clothing device, and headset devices.

As noted above, the haptic assemblies 9062 described herein can be configured to transition between a first pressurized state and a second pressurized state to provide haptic feedback to the user. Due to the ever-changing nature of artificial reality, the haptic assemblies 9062 may be required to transition between the two states hundreds, or perhaps thousands of times, during a single use. Thus, the haptic assemblies 9062 described herein are durable and designed to quickly transition from state to state. To provide some context, in the first pressurized state, the haptic assemblies 9062 do not impede free movement of a portion of the wearer's body. For example, one or more haptic assemblies 9062 incorporated into a glove are made from flexible materials that do not impede free movement of the wearer's hand and fingers (e.g., an electrostatic-zipping actuator). The haptic assemblies 9062 are configured to conform to a shape of the portion of the wearer's body when in the first pressurized state. However, once in the second pressurized state, the haptic assemblies 9062 can be configured to restrict and/or impede free movement of the portion of the wearer's body (e.g., appendages of the user's hand). For example, the respective haptic assembly 9062 (or multiple respective haptic assemblies) can restrict movement of a wearer's finger (e.g., prevent the finger from curling or extending) when the haptic assembly 9062 is in the second pressurized state. Moreover, once in the second pressurized state, the haptic assemblies 9062 may take different shapes, with some haptic assemblies 9062 configured to take a planar, rigid shape (e.g., flat and rigid), while some other haptic assemblies 9062 are configured to curve or bend, at least partially.

As a non-limiting example, the device 9000 includes a plurality of haptic devices (e.g., a pair of haptic gloves, and a haptics component of a wrist-wearable device (e.g., any of the wrist-wearable devices described with respect to FIGS. 7A-7B. Each of which can include a garment component (e.g., a garment 9004) and one or more haptic assemblies coupled (e.g., physically coupled) to the garment component. For example, each of the haptic assemblies 9062-1, 9062-2, 9062-3, . . . 9062-N are physically coupled to the garment 9004 are configured to contact respective phalanges of a user's thumb and fingers. As explained above, the haptic assemblies 9062 are configured to provide haptic simulations to a wearer of the device 9000. The garment 9004 of each device 9000 can be one of various articles of clothing (e.g., gloves, socks, shirts, or pants). Thus, a user may wear multiple devices 9000 that are each configured to provide haptic stimulations to respective parts of the body where the devices 9000 are being worn.

Figure 10C:
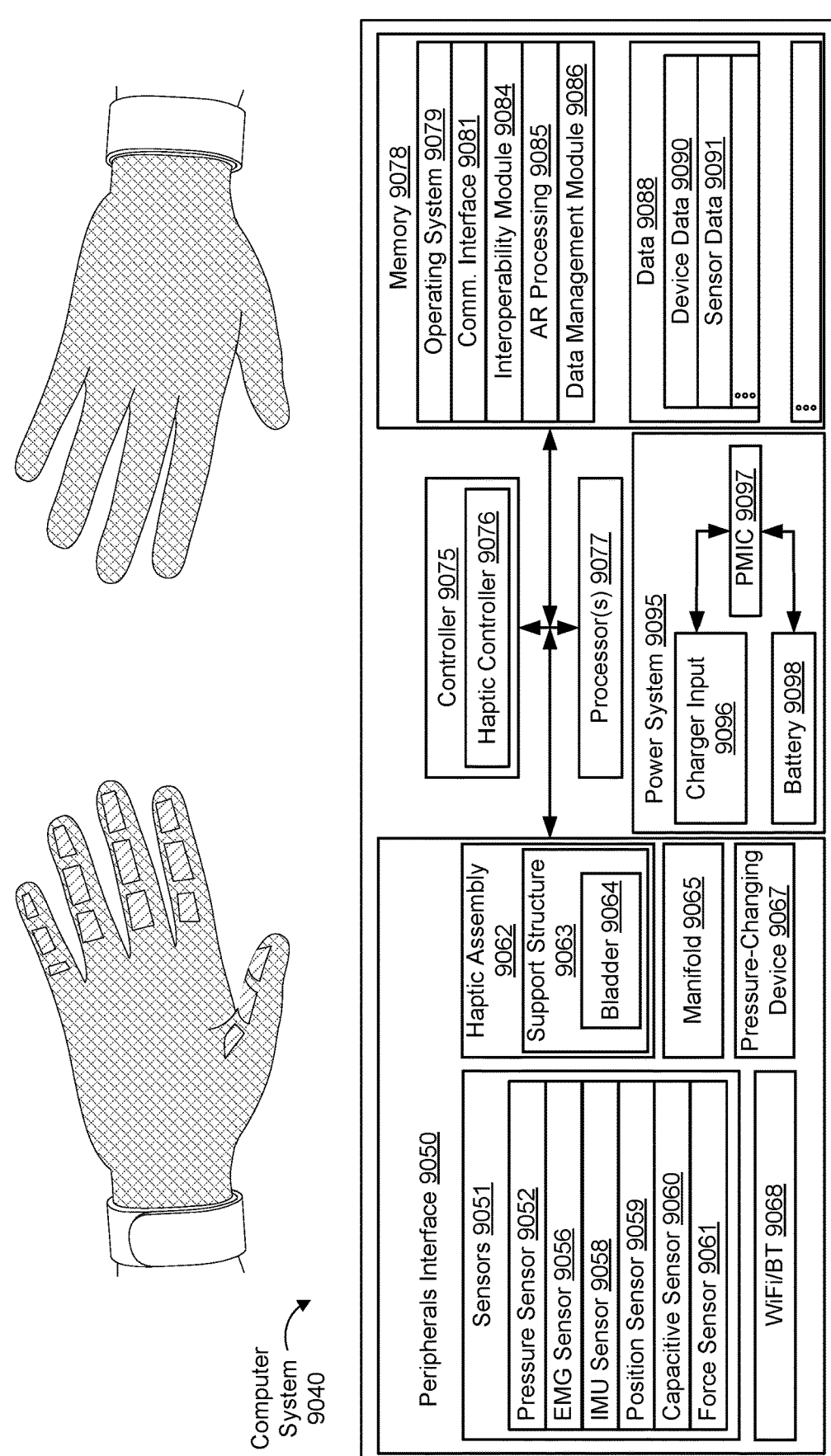

FIG. 10C shows block diagrams of a computing system 9040 of the device 9000, in accordance with some embodiments. The computing system 9040 can include one or more peripheral interfaces 9050, one or more power systems 9095, one or more controllers 9075 (including one or more haptic controllers 9076), one or more processors 9077 (as defined above, including any of the examples provided), and memory 9078, which can all be in electronic communication with each other. For example, the one or more processors 9077 can be configured to execute instructions stored in the memory 9078, which can cause a controller of the one or more controllers 9075 to cause operations to be performed at one or more peripheral devices of the peripherals interface 9050. In some embodiments, each operation described can occur based on electrical power provided by the power system 9095. The power system 9095 includes a charger input 9096, a PMIC 9097, and a battery 9098.

In some embodiments, the peripherals interface 9050 can include one or more devices configured to be part of the computing system 9040, many of which have been defined above and/or described with respect to wrist-wearable devices shown in FIGS. 7A and 7B. For example, the peripherals interface 9050 can include one or more sensors 9051. Some example sensors include: one or more pressure sensors 9052, one or more EMG sensors 9056, one or more IMU sensors 9058, one or more position sensors 9059, one or more capacitive sensors 9060, one or more force sensors 9061; and/or any other types of sensors defined above or described with respect to any other embodiments discussed herein.

In some embodiments, the peripherals interface can include one or more additional peripheral devices, including one or more Wi-Fi and/or Bluetooth devices 9068; one or more haptic assemblies 9062; one or more support structures 9063 (which can include one or more bladders 9064; one or more manifolds 9065; one or more pressure-changing devices 9067; and/or any other types of peripheral devices defined above or described with respect to any other embodiments discussed herein.

In some embodiments, each haptic assembly 9062 includes a support structure 9063, and at least one bladder 9064. The bladder 9064 (e.g., a membrane) is a sealed, inflatable pocket made from a durable and puncture resistance material, such as thermoplastic polyurethane (TPU), a flexible polymer, or the like. The bladder 9064 contains a medium (e.g., a fluid such as air, inert gas, or even a liquid)

that can be added to or removed from the bladder 9064 to change a pressure (e.g., fluid pressure) inside the bladder 9064. The support structure 9063 is made from a material that is stronger and stiffer than the material of the bladder 9064. A respective support structure 9063 coupled to a respective bladder 9064 is configured to reinforce the respective bladder 9064 as the respective bladder changes shape and size due to changes in pressure (e.g., fluid pressure) inside the bladder.

The device 9000 also includes a haptic controller 9076 and a pressure-changing device 9067. In some embodiments, the haptic controller 9076 is part of the computer system 9040 (e.g., in electronic communication with one or more processors 9077 of the computer system 9040). The haptic controller 9076 is configured to control operation of the pressure-changing device 9067, and in turn operation of the device 9000. For example, the controller 9076 sends one or more signals to the pressure-changing device 9067 to activate the pressure-changing device 9067 (e.g., turn it on and off). The one or more signals may specify a desired pressure (e.g., pounds-per-square inch) to be output by the pressure-changing device 9067. Generation of the one or more signals, and in turn the pressure output by the pressure-changing device 9067, may be based on information collected by the sensors in FIGS. 6A and 6B. For example, the one or more signals may cause the pressure-changing device 9067 to increase the pressure (e.g., fluid pressure) inside a haptic assembly 9062 at a first time, based on the information collected by the sensors in FIGS. 6A and 6B (e.g., the user makes contact with an artificial coffee mug). Then, the controller may send one or more additional signals to the pressure-changing device 9067 that cause the pressure-changing device 9067 to further increase the pressure inside the haptic assembly 9062 at a second time after the first time, based on additional information collected by the sensors 9051. Further, the one or more signals may cause the pressure-changing device 9067 to inflate one or more bladders 9064 in a device 9000-A, while one or more bladders 9064 in a device 9000-B remain unchanged. Additionally, the one or more signals may cause the pressure-changing device 9067 to inflate one or more bladders 9064 in a device 9000-A to a first pressure and inflate one or more other bladders 9064 in the device 9000-A to a second pressure different from the first pressure. Depending on the number of devices 9000 serviced by the pressure-changing device 9067, and the number of bladders therein, many different inflation configurations can be achieved through the one or more signals and the examples above are not meant to be limiting.

The device 9000 may include an optional manifold 9065 between the pressure-changing device 9067 and the devices 9000. The manifold 9065 may include one or more valves (not shown) that pneumatically couple each of the haptic assemblies 9062 with the pressure-changing device 9067 via tubing. In some embodiments, the manifold 9065 is in communication with the controller 9075, and the controller 9075 controls the one or more valves of the manifold 9065 (e.g., the controller generates one or more control signals). The manifold 9065 is configured to switchably couple the pressure-changing device 9067 with one or more haptic assemblies 9062 of the same or different devices 9000 based on one or more control signals from the controller 9075. In some embodiments, instead of using the manifold 9065 to pneumatically couple the pressure-changing device 9067 with the haptic assemblies 9062, the device 9000 may include multiple pressure-changing devices 9067, where each pressure-changing device 9067 is pneumatically coupled directly with a single (or multiple) haptic assembly 9062. In some embodiments, the pressure-changing device 9067 and the optional manifold 9065 are configured as part of one or more of the devices 9000 (not illustrated) while, in other embodiments, the pressure-changing device 9067 and the optional manifold 9065 are configured as external to the device 9000. A single pressure-changing device 9067 may be shared by multiple devices 9000.

In some embodiments, the pressure-changing device 9067 is a pneumatic device, hydraulic device, a pneudraulic device, or some other device capable of adding and removing a medium (e.g., fluid, liquid, gas) from the one or more haptic assemblies 9062.

The devices shown in FIGS. 10A to 10C may be coupled via a wired connection (e.g., via busing). Alternatively, one or more of the devices shown in FIGS. 10A to 10C may be wirelessly connected (e.g., via short-range communication signals).

The memory 9078 includes instructions and data, some or all of which may be stored as non-transitory computer-readable storage media within the memory 9078. For example, the memory 9078 can include one or more operating systems 9079; one or more communication interface applications 9081; one or more interoperability modules 9084; one or more AR processing applications 9085; one or more data management modules 9086; and/or any other types of data defined above or described with respect to any other embodiments discussed herein.

The memory 9078 also includes data 9088 which can be used in conjunction with one or more of the applications discussed above. The data 9088 can include: device data 9090; sensor data 9091; and/or any other types of data defined above or described with respect to any other embodiments discussed herein.

Any data collection performed by the devices described herein and/or any devices configured to perform or cause the performance of the different embodiments described above in reference to any of the Figures, hereinafter the "devices," is done with user consent and in a manner that is consistent with all applicable privacy laws. Users are given options to allow the devices to collect data, as well as the option to limit or deny collection of data by the devices. A user is able to opt-in or opt-out of any data collection at any time. Further, users are given the option to request the removal of any collected data.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method of providing data integrity, the method comprising:
   at a neuromuscular-signal-sensing component of a wearable device:
       detecting a neuromuscular signal via one or more electrodes;
       generating a digital signal by converting the neuromuscular signal;
       generating an encrypted signal by encrypting the digital signal;
       transmitting the encrypted signal to a controller component of the wearable device, the controller component being distinct from the neuromuscular-signal-sensing component; and
       in accordance with the neuromuscular-signal-sensing component being validated, adjusting performance of the wearable device based on one or more capabilities of the neuromuscular-signal-sensing component.

2. The method of claim 1, wherein the neuromuscular-signal-sensing component and the controller component are arranged on a wrist-wearable device.

3. The method of claim 1, wherein:
   the wearable device comprises one or more additional neuromuscular-signal-sensing components; and
   each additional neuromuscular-signal-sensing component comprising a respective encryption component.

4. The method of claim 1, wherein the neuromuscular-signal-sensing component comprises the one or more electrodes, an analog frontend (AFE), an analog-to-digital converter (ADC), and encryption logic.

5. The method of claim 4, wherein:
   the analog frontend, the analog-to-digital converter, and the encryption logic are arranged on electrode silicon coupled to the one or more electrodes; and
   the electrode silicon is enclosed in a housing.

6. The method of claim 1, further comprising, at the controller component:
   receiving the encrypted signal from the neuromuscular-signal-sensing component;
   generating a decrypted signal by decrypting the encrypted signal; and
   validating the neuromuscular-signal-sensing component based on the decrypted signal.

7. The method of claim 6, wherein validating the neuro-muscular-signal-sensing component comprises identifying one or more capabilities of the neuromuscular-signal-sensing component.

8. The method of claim 6, further comprising, in accordance with the neuromuscular-signal-sensing component not being validated, generating a notification for a user of the wearable device.

9. The method of claim 6, further comprising, at the controller component:

receiving a signal from an additional neuromuscular-signal-sensing component;

validating the additional neuromuscular-signal-sensing component based on the received signal;

in accordance with the additional neuromuscular-signal-sensing component being validated, activating an operating mode of the wearable device; and in accordance with the additional neuromuscular-signal-sensing component not being validated, forgoing activating the operating mode of the wearable device.

10. The method of claim 9, further comprising adjusting a machine-learning model based on a number and type of neuromuscular-signal-sensing components coupled to the controller component.

11. The method of claim 1, wherein adjusting performance of the wearable device includes adjusting a machine-learning model based on one or more capabilities of the neuromuscular-signal-sensing component.

12. The method of claim 1, further comprising, at the neuromuscular-signal-sensing component:

receiving a secret; and storing the secret for use with subsequent encryption operations.

13. A wearable device, comprising:

one or more processors; and memory, comprising instructions, which, when executed by the one or more processors, cause operations at the wearable device for:

at a neuromuscular-signal-sensing component of a wearable device:

detecting a neuromuscular signal via one or more electrodes;

generating a digital signal by converting the neuromuscular signal;

generating an encrypted signal by encrypting the digital signal;

transmitting the encrypted signal to a controller component of the wearable device, the controller component being distinct from the neuromuscular-signal-sensing component; and in accordance with the neuromuscular-signal-sensing component being validated, adjusting performance of the wearable device based on one or more capabilities of the neuromuscular-signal-sensing component.

14. The wearable device of claim 13, wherein the neuromuscular-signal-sensing component and the controller component are arranged on a wrist-wearable device.

15. The wearable device of claim 13, further comprising:

one or more additional neuromuscular-signal-sensing components, each additional neuromuscular-signal-sensing component comprising a respective encryption component.

16. The wearable device of claim 13, wherein:

the neuromuscular-signal-sensing component comprises the one or more electrodes, an analog frontend (AFE), an analog-to-digital converter (ADC), and encryption logic.

17. The wearable device of claim 16, wherein:

the analog frontend, the analog-to-digital converter, and the encryption logic are arranged on electrode silicon coupled to the one or more electrodes; and the electrode silicon is enclosed in a housing.

18. The wearable device of claim 13, wherein the memory further comprises instructions for:

at the controller component:

receiving the encrypted signal from the neuromuscular-signal-sensing component;

generating a decrypted signal by decrypting the encrypted signal; and validating the neuromuscular-signal-sensing component based on the decrypted signal.

19. The wearable device of claim 18, wherein validating the neuromuscular-signal-sensing component comprises identifying one or more capabilities of the neuromuscular-signal-sensing component.

20. A non-transitory computer-readable storage medium, comprising instructions, which, when executed by one or more processors of an electronic device, cause performance of operations for:

at a neuromuscular-signal-sensing component of a wearable device:

detecting a neuromuscular signal via one or more electrodes;

generating a digital signal by converting the neuromuscular signal;

generating an encrypted signal by encrypting the digital signal;

transmitting the encrypted signal to a controller component of the wearable device, the controller component being distinct from the neuromuscular-signal-sensing component; and in accordance with the neuromuscular-signal-sensing component being validated, adjusting performance of the wearable device based on one or more capabilities of the neuromuscular-signal-sensing component.

\* \* \* \* \*